(12) United States Patent
Canales et al.

(10) Patent No.: US 10,167,480 B2
(45) Date of Patent: Jan. 1, 2019

(54) STRONG ACTIVATION DOMAIN

(71) Applicant: Mendel Biotechnology, Inc., Hayward, CA (US)

(72) Inventors: Roger Canales, San Diego, CA (US); Shiv Tiwari, San Jose, CA (US); T. Lynne Reuber, San Mateo, CA (US); Karen S. Century, Chapel Hill, NC (US); Oliver J. Ratcliffe, Oakland, CA (US)

(73) Assignee: Mendel Biotechnology, Inc., Hayward, CA (US)

( * ) Notice: Subject to any disclaimer, the term of this patent is extended or adjusted under 35 U.S.C. 154(b) by 786 days.

(21) Appl. No.: 14/076,550

(22) Filed: Nov. 11, 2013

(65) Prior Publication Data

US 2014/0068821 A1 Mar. 6, 2014

Related U.S. Application Data

(63) Continuation of application No. 13/000,488, filed as application No. PCT/US2009/048814 on Jun. 26, (Continued)

(51) Int. Cl.
*C12N 15/82* (2006.01)
*C07K 14/415* (2006.01)

(52) U.S. Cl.
CPC ........ *C12N 15/8216* (2013.01); *C07K 14/415* (2013.01); *C12N 15/8251* (2013.01);
(Continued)

(58) Field of Classification Search
None
See application file for complete search history.

(56) References Cited

U.S. PATENT DOCUMENTS

| 7,663,025 B2 | 2/2010 | Heard et al. |
| 7,888,558 B2 | 2/2011 | Gutterson et al. |
| | (Continued) | |

FOREIGN PATENT DOCUMENTS

| CA | 2575597 A1 | 3/2006 |
| CA | 2575597 | 4/2012 |
| | (Continued) | |

OTHER PUBLICATIONS

Kummerfeld et al. DBD: a transcription factor prediction database. Nucleic Acids Research. 2006. 34: D74-D81.*
(Continued)

*Primary Examiner* — Ashley K Buran
(74) *Attorney, Agent, or Firm* — Dentons US LLP

(57) ABSTRACT

A new and strong transcriptional activation domain was identified from the *Arabidopsis* protein Ethylene Response Factor 98 (AtERF98). This domain has been designated as the "EDLL domain" and has a number of highly conserved amino acid residues that are found throughout the members of the AtERF98 family from plants, including in monocot and eudicot orthologs. The EDLL domain was shown to be highly active when it was fused to transcription factors from plant and yeast, and was also shown to have activation potential comparable to the widely-used VP16 activation domain derived from Herpes simplex. The EDLL domain was also active when it was targeted to a gene promoter by a sequence-specific DNA binding protein or by protein-protein interactions. Unlike other known activation domains such as VP16 and GAL4, the EDLL domain is relatively small in size, and being of plant origin, it is favored as a strong transcriptional activation tool for application in transgenic food crops.

31 Claims, 6 Drawing Sheets

Figure 2:
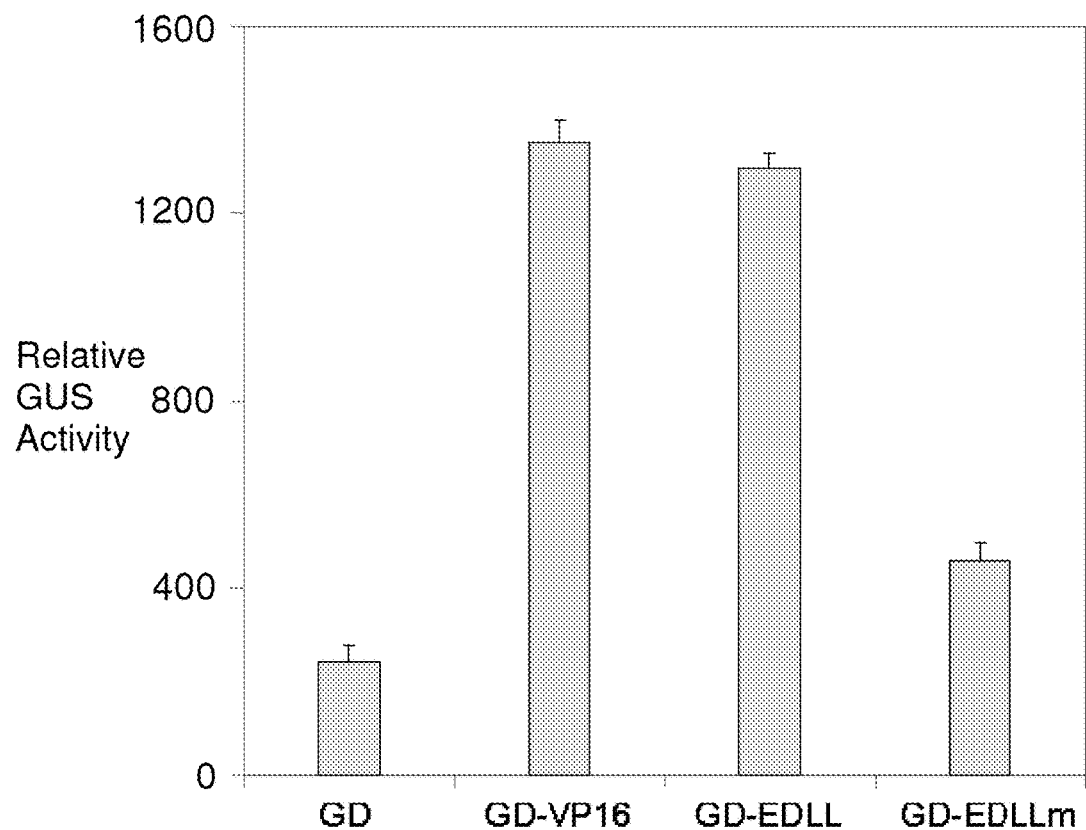

Specification includes a Sequence Listing.

Related U.S. Application Data 2009, now abandoned, application No. 14/076,550, which is a continuation-in-part of application No. 12/705,845, filed on Feb. 15, 2010, now Pat. No. 8,686,226, which is a continuation-in-part of application No. 10/714,887, filed on Nov. 13, 2003, now abandoned, and a continuation-in-part of application No. 11/981,576, filed on Oct. 30, 2007, now Pat. No. 7,888,558, and a continuation-in-part of application No. PCT/US2004/037584, filed on Nov. 12, 2004, application No. 14/076,550, which is a continuation-in-part of application No. 10/903,236, filed on Jul. 30, 2004, now Pat. No. 8,912,394, and a continuation-in-part of application No. 12/064,961, filed as application No. PCT/US2006/034615 on Aug. 31, 2006, now abandoned.

(60) Provisional application No. 61/076,534, filed on Jun. 27, 2008.

(52) U.S. Cl.
CPC ...... *C12N 15/8261* (2013.01); *C07K 2319/00* (2013.01); *Y02A 40/146* (2018.01)

(56) References Cited

U.S. PATENT DOCUMENTS

| | | | |
|---|---|---|---|
| 8,030,546 B2 | 10/2011 | Reuber et al. | |
| 2003/0121070 A1* | 6/2003 | Adam | C12N 15/8261 800/278 |
| 2005/0155117 A1* | 7/2005 | Century | C12N 15/8282 800/301 |

FOREIGN PATENT DOCUMENTS

| | | |
|---|---|---|
| CA | 2575597 | 5/2013 |
| EP | 05818216.3 | 3/2008 |
| EP | 05818216.3 | 12/2008 |
| EP | 05818216.3 | 12/2009 |
| EP | 05818216.3 | 8/2010 |
| WO | 2006/033708 A2 | 3/2006 |
| WO | 2006/033708 A3 | 3/2006 |
| WO | PCT/US2005/027151 | 3/2007 |
| WO | PCT/US2009/048814 | 10/2009 |
| WO | 2009/158591 A1 | 12/2009 |
| WO | PCT/US2009/048814 | 1/2011 |

OTHER PUBLICATIONS

Aoyama et al. A glucocorticoid-mediated transcriptional induction system in transgenic plants. The Plant Journal. 1997. 11(3): 605-612.*

DeYoung et al. Plant NBS-LRR proteins in pathogen sensing and host defense. Nature Immunology. 2006. 7(12): 1243-1249.*

Park et al. Overexpression of the tobacco Tsi1 gene encoding an EREBP/AP2-type transcription factor enhances resistance against pathogen attack and osmotic stress in tobacco. The Plant cell. 2001. 13: 1035-1046.*

Tiwari, S. B., et al.; "The EDLL motif: a potent plant transcriptional activation domain from AP2/ERF transcription factors"; The Plant Journal (2012) 70:855-865.

NCBI Accession No. AB025608 (gi: 4589414); (Apr. 2, 1999); Sato, S., et al.; *Arabidopsis thaliana* genomic DNA chromosome 3, TAC clone:K14B15; *Arabidopsis thaliana*.

NCBI Accession No. BAA95736.1 (gi:7939533); (Apr. 2, 1999); Nakamura, Y.; Nicotiana EREBP-3-like protein [*Arabidopsis thaliana*]; *Arabidopsis thaliana*.

Office Action for U.S. Appl. No. 11/435,388 dated Apr. 16, 2008.
Office Action for U.S. Appl. No. 10/903,236 dated Dec. 13, 2013.
Office Action for U.S. Appl. No. 10/903,236 dated Jul. 30, 2013.
Office Action for U.S. Appl. No. 10/903,236 dated May 22, 2009.
Office Action for U.S. Appl. No. 10/903,236 dated Jul. 10, 2008.
Office Action for U.S. Appl. No. 10/903,236 dated May 14, 2007.
Office Action for U.S. Appl. No. 10/903,236 dated Jul. 6, 2006.
Office Action for U.S. Appl. No. 11/981,576 dated Oct. 23, 2009.
Office Action for U.S. Appl. No. 12/077,535 dated Feb. 5, 2010.
Office Action for U.S. Appl. No. 12/077,535 dated Aug. 27, 2009.
Office Action for U.S. Appl. No. 12/077,535 dated Jul. 19, 2010.

* cited by examiner

| Name (SEQ ID NO.) | | | | | | | | | | | | |
|---|---|---|---|---|---|---|---|---|---|---|---|---|
| G1752_At (64) | L | V | V | F | E | D | L | G | A | E | Y | L | E | Q | L | L |
| G1791_At (40) | V | I | E | F | E | Y | L | D | D | S | L | L | E | E | L | L |
| G1795_At (38) | V | F | E | F | E | Y | L | D | D | S | V | L | E | E | L | L |
| G30_At (39) | V | F | E | F | E | Y | L | D | D | S | V | L | D | E | L | L |
| G3380_Os (52) | V | I | E | L | E | C | L | D | D | Q | V | L | Q | E | M | L |
| G3794_Zm (53) | V | I | E | L | E | C | L | D | D | Q | V | L | Q | E | M | L |
| G3736_Ta (47) | V | I | E | F | E | Y | L | D | D | D | V | L | Q | S | M | L |
| G3381_Os (48) | P | I | E | F | E | Y | L | D | D | H | V | L | Q | E | M | L |
| G3517_Zm (44) | V | I | E | F | E | Y | L | D | D | E | V | L | Q | F | M | L |
| G3739_Zm (46) | V | I | E | L | E | Y | L | D | D | E | V | L | Q | E | M | L |
| G3520_Gm (41) | V | I | E | F | E | C | L | D | D | K | L | L | E | D | L | L |
| G3383_Os (43) | K | I | E | F | E | Y | L | D | D | K | V | L | D | D | L | L |
| G3737_Os (49) | K | V | E | L | V | Y | L | D | D | K | V | L | D | E | L | L |
| G3515_Os (50) | K | V | E | L | E | C | L | D | D | K | V | L | E | D | L | L |
| G3516_Zm (51) | K | V | E | L | E | C | L | D | D | R | V | L | E | E | L | L |
| G1792_At (37) | V | F | E | F | E | Y | L | D | D | K | V | L | E | F | L | L |
| G3518_Gm (45) | T | F | E | L | E | Y | F | D | N | K | L | L | E | E | L | L |
| G3519_Gm (42) | T | F | E | L | E | Y | L | D | N | K | L | L | E | E | L | L |
| G3735_Mt (54) | - | - | E | L | E | F | L | D | N | K | L | L | Q | E | L | L |
| G26_At (65) | S | S | S | S | S | S | L | N | H | Q | G | L | R | P | N | L |
| G22_At (66) | E | L | D | F | T | V | D | Q | F | Y | F | D | G | S | L | L |
| G1006_At (67) | K | C | E | V | - | G | D | E | T | R | V | D | - | E | L | L |
| G28_At (68) | T | V | K | C | E | V | V | E | V | A | R | G | - | R | L | L |
| G1751_At (69) | C | N | M | E | E | W | M | N | M | M | M | M | D | F | L | G |
| G45_At (70) | L | F | E | F | E | D | L | G | S | D | Y | L | E | T | L | L |
| G1266_At (71) | V | V | V | F | E | D | L | G | E | Q | Y | L | E | E | L | L |
| G2512_At (72) | L | V | V | L | E | D | L | G | A | E | Y | L | E | E | L | - |

Sequence Logo (95)

FIG. 1

SEQUENCE LISTING

<160> NUMBER OF SEQ ID NOS: 139

<210> SEQ ID NO 1
<211> LENGTH: 696
<212> TYPE: DNA
<213> ORGANISM: Arabidopsis thaliana
<220> FEATURE:
<223> OTHER INFORMATION: AtERF98 (G1792)

<400> SEQUENCE: 1

```
aatccataga tctcttatta ataacagtg ctgaccaagc tcttacaaag caaaccaatc        60
tagaacacca aagttaatgg agagctcaaa caggagcagc aacaaccaat cacaagatga       120
caagcaagct cgtttccggg gagttcgaag aaggccttgg ggaaagtttg cagcagagat       180
tcgagacccg tcgagaaacg gtgcccgtct ttggctcggg acatttgaga ccgctgagga       240
ggcagcaagg gcttatgacc gagcagcctt taaccttagg ggtcatctcg ctatactcaa       300
cttccctaat gagtattatc cacgtatgga cgactactcg cttcgccctc cttatgcttc       360
ttcttcttcg tcgtcgtcat cgggttcaac ttctactaat gtgagtcgac aaaaccaaag       420
agaagttttc gagtttgagt atttggacga taaggttctt gaagaacttc ttgattcaga       480
agaaaggaag agataatcac gattagtttt gttttgatat tttatgtggc actgttgtgg       540
ctacctacgt gcattatgtg catgtatagg tcgcttgatt agtactttat aacatgcatg       600
ccacgaccat aaattgtaag agaagacgta ctttgcgttt tcatgaaata tgaatgttag       660
atggtttgag tacaaaaaaa aaaaaaaaaa aaaaaa                                 696
```

<210> SEQ ID NO 2
<211> LENGTH: 139
<212> TYPE: PRT
<213> ORGANISM: Arabidopsis thaliana
<220> FEATURE:
<223> OTHER INFORMATION: AtERF98 (G1792) polypeptide

<400> SEQUENCE: 2

```
Met Glu Ser Ser Asn Arg Ser Ser Asn Asn Gln Ser Gln Asp Asp Lys
1               5                   10                  15

Gln Ala Arg Phe Arg Gly Val Arg Arg Arg Pro Trp Gly Lys Phe Ala
            20                  25                  30

Ala Glu Ile Arg Asp Pro Ser Arg Asn Gly Ala Arg Leu Trp Leu Gly
        35                  40                  45

Thr Phe Glu Thr Ala Glu Glu Ala Ala Arg Ala Tyr Asp Arg Ala Ala
    50                  55                  60

Phe Asn Leu Arg Gly His Leu Ala Ile Leu Asn Phe Pro Asn Glu Tyr
65                  70                  75                  80

Tyr Pro Arg Met Asp Asp Tyr Ser Leu Arg Pro Pro Tyr Ala Ser Ser
                85                  90                  95

Ser Ser Ser Ser Ser Ser Gly Ser Thr Ser Thr Asn Val Ser Arg Gln
            100                 105                 110
```

Asn Gln Arg Glu Val Phe Glu Phe Glu Tyr Leu Asp Asp Lys Val Leu
    115                 120                 125

Glu Glu Leu Leu Asp Ser Glu Glu Arg Lys Arg
    130                 135

<210> SEQ ID NO 3
<211> LENGTH: 450
<212> TYPE: DNA
<213> ORGANISM: Arabidopsis thaliana
<220> FEATURE:
<223> OTHER INFORMATION: G1795

<400> SEQUENCE: 3
acaaacacgc aaaaagtcat taatatatgg atcaaggagg tcgaggtgtc ggtgccgagc      60
atggaaagta ccggggagtt cggagacgac cttggggaaa atatgcagca gagatacgag     120
attcgaggaa gcacggtgaa cgtgtgtggc ttggaacgtt cgatacggca gaggaagcgg     180
ctagagccta tgaccaagct gcttactcca tgagaggcca agcagcaatc cttaacttcc     240
ctcatgagta taacatgggg agtggtgtct cttcttccac cgccatggct ggatcttcct     300
ccgcctccgc tccgcttcct tcttcttcta ggcaagtttt tgaatttgag tacttggatg     360
atagtgtttt ggaggagctc cttgaggaag gagagaaacc taacaagggc aagaagaaat     420
gagcgagata taattcatga ttatttctaa                                       450

<210> SEQ ID NO 4
<211> LENGTH: 131
<212> TYPE: PRT
<213> ORGANISM: Arabidopsis thaliana
<220> FEATURE:
<223> OTHER INFORMATION: G1795 polypeptide

<400> SEQUENCE: 4

Met Asp Gln Gly Gly Arg Gly Val Gly Ala Glu His Gly Lys Tyr Arg
1               5                   10                  15

Gly Val Arg Arg Arg Pro Trp Gly Lys Tyr Ala Ala Glu Ile Arg Asp
            20                  25                  30

Ser Arg Lys His Gly Glu Arg Val Trp Leu Gly Thr Phe Asp Thr Ala
        35                  40                  45

Glu Glu Ala Ala Arg Ala Tyr Asp Gln Ala Ala Tyr Ser Met Arg Gly
    50                  55                  60

Gln Ala Ala Ile Leu Asn Phe Pro His Glu Tyr Asn Met Gly Ser Gly
65                  70                  75                  80

Val Ser Ser Ser Thr Ala Met Ala Gly Ser Ser Ala Ser Ala Ser
                85                  90                  95

Ala Ser Ser Ser Arg Gln Val Phe Glu Phe Glu Tyr Leu Asp Asp
            100                 105                 110

Ser Val Leu Glu Glu Leu Leu Glu Glu Gly Glu Lys Pro Asn Lys Gly
        115                 120                 125

Lys Lys Lys
    130

<210> SEQ ID NO 5
<211> LENGTH: 553
<212> TYPE: DNA
<213> ORGANISM: Arabidopsis thaliana
<220> FEATURE:
<223> OTHER INFORMATION: G30

<400> SEQUENCE: 5

```
ctcttctgac gcacaacagt atatacacat acacagatat atggatcaag gaggtcgtag     60
cagtggtagt ggaggaggag gagccgagca agggaagtac cgtggagtaa ggagacgacc    120
ttggggtaaa tacgccgcgg aaataagaga ttcgaggaag cacggagagc gtgtgtggct    180
agggacattc gacactgcgg aagacgcggc tcgagcctat gaccgagccg cctattcaat    240
gagaggcaaa gctgccattc tcaacttccc tcacgagtat aacatgggaa ccggatcctc    300
atccactgcg gctaattctt cttcctcgtc gcagcaagtt tttgagtttg agtacttgga    360
cgatagcgtt ttggatgaac ttcttgaata tggagagaac tataacaaga ctcataatat    420
caacatgggc aagaggcaat aagggaata caatcggtat taactgaaag ttatgtgaaa    480
gaccattttc agttataaca aataaaataa atcccaagc gtacaaagct gtttctaaaa    540
aaaaaaaaaa aaa                                                       553

<210> SEQ ID NO 6
<211> LENGTH: 133
<212> TYPE: PRT
<213> ORGANISM: Arabidopsis thaliana
<220> FEATURE:
<223> OTHER INFORMATION: G30 polypeptide

<400> SEQUENCE: 6

Met Asp Gln Gly Gly Arg Ser Ser Gly Ser Gly Gly Gly Gly Ala Glu
1               5                   10                  15

Gln Gly Lys Tyr Arg Gly Val Arg Arg Pro Trp Gly Lys Tyr Ala
            20                  25                  30

Ala Glu Ile Arg Asp Ser Arg Lys His Gly Glu Arg Val Trp Leu Gly
        35                  40                  45

Thr Phe Asp Thr Ala Glu Asp Ala Ala Arg Ala Tyr Asp Arg Ala Ala
    50                  55                  60

Tyr Ser Met Arg Gly Lys Ala Ala Ile Leu Asn Phe Pro His Glu Tyr
65                  70                  75                  80

Asn Met Gly Thr Gly Ser Ser Thr Ala Ala Asn Ser Ser Ser Ser
                85                  90                  95

Ser Gln Gln Val Phe Glu Phe Glu Tyr Leu Asp Asp Ser Val Leu Asp
            100                 105                 110

Glu Leu Leu Glu Tyr Gly Glu Asn Tyr Asn Lys Thr His Asn Ile Asn
        115                 120                 125

Met Gly Lys Arg Gln
    130

<210> SEQ ID NO 7
<211> LENGTH: 549
<212> TYPE: DNA
<213> ORGANISM: Arabidopsis thaliana
<220> FEATURE:
<223> OTHER INFORMATION: G1791

<400> SEQUENCE: 7
atgtacatgc aaaacaaaa accttaaaag ctttcatgga acgtatagag tcttataaca     60
cgaatgagat gaaatacaga ggcgtacgaa agcgtccatg ggaaaatat gcggcggaga    120 ttcgcgactc agctagacac ggtgctcgtg tttggcttgg acgttttaac acagcggaag    180
acgcggctcg ggcttatgat agagcagctt tcggcatgag aggccaaagg gccattctca    240
attttcctca cgagtatcaa atgatgaagg acgtccaaa tggcagccac gagaatgcag    300
tggcttcctc gtcgtcggga tatagaggag gaggtggtgg tgatgatggg agggaagtta    360
```

```
ttgagttcga gtatttggat gatagtttat tggaggagct tttagattat ggtgagagat      420
ctaaccaaga caattgtaac gacgcaaacc gctagatcat cactacttac ttacagtgta      480 atgttttttgg agtaaagagt aataatcaat ataatatact ttagtttagg aaaaaaaaaa     540
aaaaaaaaa                                                              549
```

<210> SEQ ID NO 8
<211> LENGTH: 139
<212> TYPE: PRT
<213> ORGANISM: Arabidopsis thaliana
<220> FEATURE:
<223> OTHER INFORMATION: G1791 polypeptide

<400> SEQUENCE: 8

```
Met Glu Arg Ile Glu Ser Tyr Asn Thr Asn Glu Met Lys Tyr Arg Gly
1               5                   10                  15

Val Arg Lys Arg Pro Trp Gly Lys Tyr Ala Ala Glu Ile Arg Asp Ser
            20                  25                  30

Ala Arg His Gly Ala Arg Val Trp Leu Gly Thr Phe Asn Thr Ala Glu
        35                  40                  45

Asp Ala Ala Arg Ala Tyr Asp Arg Ala Ala Phe Gly Met Arg Gly Gln
    50                  55                  60

Arg Ala Ile Leu Asn Phe Pro His Glu Tyr Gln Met Met Lys Asp Gly
65                  70                  75                  80

Pro Asn Gly Ser His Glu Asn Ala Val Ala Ser Ser Ser Gly Tyr
                85                  90                  95

Arg Gly Gly Gly Gly Asp Asp Gly Arg Glu Val Ile Glu Phe Glu
            100                 105                 110

Tyr Leu Asp Asp Ser Leu Leu Glu Glu Leu Leu Asp Tyr Gly Glu Arg
        115                 120                 125

Ser Asn Gln Asp Asn Cys Asn Asp Ala Asn Arg
    130                 135
```

<210> SEQ ID NO 9
<211> LENGTH: 440
<212> TYPE: DNA
<213> ORGANISM: Glycine max
<220> FEATURE:
<223> OTHER INFORMATION: G3520

<400> SEQUENCE: 9

```
aaggcacaca atggaagagg agtcaaagga gaaaagaag gacactaagg aggaaccacg       60
ttatagagga gtgcggcggc ggccgtgggg gaagttcgcg gccgagattc gggacccggc      120
ccggcacggt gcccgagtgt ggctgggac atttctcacg gcggaggagg ctgctagggc      180
ttatgaccga gctgcctatg agatgagggg cgctttagcc gttctcaatt ttccaaatga     240
gtatccttca tgctcttcta tgaactcatc ttcaacatta gcaccttcat cttcttcttc     300
aaattcaatg cttaaaagtg atcatggtaa acaagttatt gagttcgagt gcttggatga     360
caaattgtta gaggaccttc ttgattgtga tgactatgcc tacgagaaag acttgcctaa     420
gaactgaacg gtttgatcaa                                                 440
```

<210> SEQ ID NO 10
<211> LENGTH: 138
<212> TYPE: PRT
<213> ORGANISM: Glycine max
<220> FEATURE:
<223> OTHER INFORMATION: G3520 polypeptide

<400> SEQUENCE: 10

Met Glu Glu Glu Ser Lys Glu Lys Lys Asp Thr Lys Glu Pro
1               5                   10                  15

Arg Tyr Arg Gly Val Arg Arg Pro Trp Gly Lys Phe Ala Ala Glu
            20                  25                  30

Ile Arg Asp Pro Ala Arg His Gly Ala Arg Val Trp Leu Gly Thr Phe
                35                  40                  45

Leu Thr Ala Glu Glu Ala Ala Arg Ala Tyr Asp Arg Ala Ala Tyr Glu
        50                  55                  60

Met Arg Gly Ala Leu Ala Val Leu Asn Phe Pro Asn Glu Tyr Pro Ser
65                  70                  75                  80

Cys Ser Ser Met Asn Ser Ser Thr Leu Ala Pro Ser Ser Ser
                85                  90                  95

Ser Asn Ser Met Leu Lys Ser Asp His Gly Lys Gln Val Ile Glu Phe
                100                 105                 110

Glu Cys Leu Asp Asp Lys Leu Leu Glu Asp Leu Leu Asp Cys Asp Asp
            115                 120                 125

Tyr Ala Tyr Glu Lys Asp Leu Pro Lys Asn
        130                 135

<210> SEQ ID NO 11
<211> LENGTH: 609
<212> TYPE: DNA
<213> ORGANISM: Glycine max
<220> FEATURE:
<223> OTHER INFORMATION: G3519

<400> SEQUENCE: 11
tttctttctt tctatacttt ttgtggttct gattattaag ttctaagaga ataacaatgg     60
agggtggaag atcatctgtt tcaaatggga attgtgaggt tcggtataga gggattagaa    120
gaaggccatg gggcaagttt gcagcagaga ttcgtgaccc tacgaggaaa gggacaagga    180
tatggcttgg aacatttgac actgcggaac aagctgctcg agcttatgat gctgctgctt    240
ttcattttcg tggtcataga gcaattctca acttcccaaa tgagtaccaa tctcataatc    300
caaactcttc tttgcctatg cctctaattg tgcctcctcc ttcttattct tcttctttca    360
cttctaatta ttctgctgat gataataacc accttgtgag acctggagaa ataatgcaag    420
gtggtgatct tgatgacact tttgagttgg agtacttgga taataagttg ctcgaggaac    480
tccttcagat gcaagataac agacacttct aaaagtaaaa tataacacaa gccagctatg    540
ttgtgttagt cactggcatg aaataaaatg caaagaaata ttgttgattt tatttaatat    600
attttgttt                                                            609

<210> SEQ ID NO 12
<211> LENGTH: 151
<212> TYPE: PRT
<213> ORGANISM: Glycine max
<220> FEATURE:
<223> OTHER INFORMATION: G3519 polypeptide

<400> SEQUENCE: 12

Met Glu Gly Gly Arg Ser Ser Val Ser Asn Gly Asn Cys Glu Val Arg
1               5                   10                  15

Tyr Arg Gly Ile Arg Arg Arg Pro Trp Gly Lys Phe Ala Ala Glu Ile
            20                  25                  30

Arg Asp Pro Thr Arg Lys Gly Thr Arg Ile Trp Leu Gly Thr Phe Asp
        35                  40                  45

```
Thr Ala Glu Gln Ala Ala Arg Ala Tyr Asp Ala Ala Phe His Phe
    50                  55                  60

Arg Gly His Arg Ala Ile Leu Asn Phe Pro Asn Glu Tyr Gln Ser His
 65                  70                  75                  80

Asn Pro Asn Ser Ser Leu Pro Met Pro Leu Ile Val Pro Pro Ser
                85                  90                  95

Tyr Ser Ser Ser Phe Thr Ser Asn Tyr Ser Ala Asp Asp Asn His
            100                 105                 110

Leu Val Arg Pro Gly Glu Ile Met Gln Gly Gly Asp Leu Asp Thr
        115                 120                 125

Phe Glu Leu Glu Tyr Leu Asp Asn Lys Leu Leu Glu Glu Leu Leu Gln
    130                 135                 140

Met Gln Asp Asn Arg His Phe
145                 150

<210> SEQ ID NO 13
<211> LENGTH: 375
<212> TYPE: DNA
<213> ORGANISM: Oryza sativa
<220> FEATURE:
<223> OTHER INFORMATION: G3383

<400> SEQUENCE: 13
atggaggaca accggagcaa ggacacggcg accaagtacc gcggcgtgag gaggcggccg      60
tggggcaagt tcgcggcgga gatccgcgac ccggagcgcg gcgggcgcg cgtctggctc     120 ggcaccttcg acaccgccga ggaggcggcg cgtgcctacg accgcgcggc ctacgcccag    180
cgcggcgccg ccgccgtgct caacttcccg gccgccgccg ccgccggcag gggtggagga    240
gccggcggcg ccgcttccgg gtcgtcgtcg tcgtcgtccg cgcagcgcgg caggggcgac    300
aagatcgagt tcgagtacct cgacgacaag gtgctcgacg atctcctcga cgacgagaag    360
taccgtggta aatga                                                     375

<210> SEQ ID NO 14
<211> LENGTH: 124
<212> TYPE: PRT
<213> ORGANISM: Oryza sativa
<220> FEATURE:
<223> OTHER INFORMATION: G3383 polypeptide

<400> SEQUENCE: 14

Met Glu Asp Asn Arg Ser Lys Asp Thr Ala Thr Lys Tyr Arg Gly Val
 1               5                  10                  15

Arg Arg Arg Pro Trp Gly Lys Phe Ala Ala Glu Ile Arg Asp Pro Glu
                20                  25                  30

Arg Gly Gly Ala Arg Val Trp Leu Gly Thr Phe Asp Thr Ala Glu Glu
            35                  40                  45

Ala Ala Arg Ala Tyr Asp Arg Ala Ala Tyr Ala Gln Arg Gly Ala Ala
        50                  55                  60

Ala Val Leu Asn Phe Pro Ala Ala Ala Ala Gly Arg Gly Gly
 65                  70                  75                  80

Ala Gly Gly Ala Ala Ser Gly Ser Ser Ser Ser Ser Ala Gln Arg
                85                  90                  95

Gly Arg Gly Asp Lys Ile Glu Phe Glu Tyr Leu Asp Asp Lys Val Leu
            100                 105                 110

Asp Asp Leu Leu Asp Asp Glu Lys Tyr Arg Gly Lys
        115                 120
```

<210> SEQ ID NO 15
<211> LENGTH: 477
<212> TYPE: DNA
<213> ORGANISM: Zea mays
<220> FEATURE:
<223> OTHER INFORMATION: G3517

<400> SEQUENCE: 15

```
tacgtccgat ccacagccat catcgccacc cgcgcgctta tggatggcga gtggtccaag      60
gacggcggag gcggcgagcc gaccaagtac cgcggcgtgc ggcgtcggcc ctggggcaag     120
tacgcggcgg agatccgcga ctcgagccgg cacggcgtcc gcatctggct cggcacgttc     180
gacaccgccg aggaggccgc cagggcgtac gaccgctccg ccaactccat gcgcggcgcc     240
aacgccgtgc tcaacttccc ggaggacgcg cccgcctacg ccgccgccgc ctcccgtggc     300
tccgccggcg gatcctcgtc cagaccggcg ggctccggcc gggacgtgat cgagtttgag     360
tacctcgacg acgaggtgct gcaggagatg ctcaggagcc aggagccgtc ggcggcggcg     420
gcgcagaaga agaagtagcg cgagcgccac aggtggcgaa acggccgctt ttccaaa       477
```

<210> SEQ ID NO 16
<211> LENGTH: 132
<212> TYPE: PRT
<213> ORGANISM: Zea mays
<220> FEATURE:
<223> OTHER INFORMATION: G3517 polypeptide

<400> SEQUENCE: 16

```
Met Asp Gly Glu Trp Ser Lys Asp Gly Gly Gly Glu Pro Thr Lys
1               5                   10                  15
Tyr Arg Gly Val Arg Arg Arg Pro Trp Gly Lys Tyr Ala Ala Glu Ile
            20                  25                  30
Arg Asp Ser Ser Arg His Gly Val Arg Ile Trp Leu Gly Thr Phe Asp
        35                  40                  45
Thr Ala Glu Glu Ala Ala Arg Ala Tyr Asp Arg Ser Ala Asn Ser Met
    50                  55                  60
Arg Gly Ala Asn Ala Val Leu Asn Phe Pro Glu Asp Ala Pro Ala Tyr
65                  70                  75                  80
Ala Ala Ala Ala Ser Arg Gly Ser Ala Gly Gly Ser Ser Arg Pro
                85                  90                  95
Ala Gly Ser Gly Arg Asp Val Ile Glu Phe Glu Tyr Leu Asp Asp Glu
            100                 105                 110
Val Leu Gln Glu Met Leu Arg Ser Gln Glu Pro Ser Ala Ala Ala Ala
        115                 120                 125
Gln Lys Lys Lys
    130
```

<210> SEQ ID NO 17
<211> LENGTH: 717
<212> TYPE: DNA
<213> ORGANISM: Glycine max
<220> FEATURE:
<223> OTHER INFORMATION: G3518

<400> SEQUENCE: 17

```
ctaacacaca taacaataac ttagcaacat tttttccttc cttctttctt tctttctata      60
cttttttgttg ttaattctaa gttctaagag aagaaaaatg gagggtggaa gatcatcagt     120
ttcaaatggg aatgttgagg ttcgttatag agggattaga agaaggccat ggggaaagtt     180
```

```
tgcagcagag attcgtgacc ctacaaggaa aggaacaagg atatggcttg gaacatttga      240
cactgctgaa caagctgcac gagcttatga tgctgctgct tttcattttc gtggccacag      300
agcaattctc aacttcccaa atgagtatca atctcataat ccaaactctt ctttgcctat      360
gcctctagct gtgtcagctc ctccttctta ttcttcttct tcttccactt ctaattattc      420
cggtgatgat aataataacc accttgtgag accagctttt tctggagaaa taatgcaagg      480
tggtgatcat gatgatgata cttttgagtt ggagtacttc gataataagt tgctcgagga      540
actccttcag atgcaagata acagacactt ctaaaagtaa aatataacac aagccagcta      600
tgttgtgtta gtcactggca tgaaataaaa tgcaagaaaa tattgttgat tttatttaat      660
atattttgtt tgattttttt ttttttttt gtagctgatc aaagttcttc gaaatga          717

<210> SEQ ID NO 18
<211> LENGTH: 158
<212> TYPE: PRT
<213> ORGANISM: Glycine max
<220> FEATURE:
<223> OTHER INFORMATION: G3518 polypeptide

<400> SEQUENCE: 18

Met Glu Gly Gly Arg Ser Ser Val Ser Asn Gly Asn Val Glu Val Arg
1               5                   10                  15

Tyr Arg Gly Ile Arg Arg Arg Pro Trp Gly Lys Phe Ala Ala Glu Ile
            20                  25                  30

Arg Asp Pro Thr Arg Lys Gly Thr Arg Ile Trp Leu Gly Thr Phe Asp
        35                  40                  45

Thr Ala Glu Gln Ala Ala Arg Ala Tyr Asp Ala Ala Ala Phe His Phe
    50                  55                  60

Arg Gly His Arg Ala Ile Leu Asn Phe Pro Asn Glu Tyr Gln Ser His
65                  70                  75                  80

Asn Pro Asn Ser Ser Leu Pro Met Pro Leu Ala Val Ser Ala Pro Pro
                85                  90                  95

Ser Tyr Ser Ser Ser Ser Thr Ser Asn Tyr Ser Gly Asp Asp Asn
            100                 105                 110

Asn Asn His Leu Val Arg Pro Ala Phe Ser Gly Glu Ile Met Gln Gly
        115                 120                 125

Gly Asp His Asp Asp Asp Thr Phe Glu Leu Glu Tyr Phe Asp Asn Lys
    130                 135                 140

Leu Leu Glu Glu Leu Leu Gln Met Gln Asp Asn Arg His Phe
145                 150                 155

<210> SEQ ID NO 19
<211> LENGTH: 899
<212> TYPE: DNA
<213> ORGANISM: Zea mays
<220> FEATURE:
<223> OTHER INFORMATION: G3739

<400> SEQUENCE: 19
cgatataatt cactcctctc aacgctcgct gcacacacac accagtgaac ctagccagcc      60
atttgccgca tcgatcatca gtcgctgtca cgcgcgccaa accaaaccaa agcccaaacc     120
cagctgcaag tgctactgac agcagctagc aaacacacac ccgtcgccat cgctatggac     180
ggcgactggt ccaaggacgg cggaggtgga gagccgacca aatatcgcgg cgtgcggcgg     240
cggccctggg gcaagtacgc ggccgagatc cgcgactcga gccgccacgg cgtccgcatc     300
```

```
tggctgggca ccttcgacac cgccgaggag gccgccaggg cgtacgaccg gagcgcctac    360
tccatgcgcg cgccaacgc cgtcctcaac ttcccggagg acgcgcacgc ctacgccgcc    420
gcctgccgcg gctccggatc ctcctcatcc tcgtccaggc ataggcagca gcagcagcag    480
ggctccggca gggacgtgat cgagctcgag tacctcgacg acgaggtgct gcaggagatg    540
ctcaggaacc acgagccgtc gtcgtctgcg aggaagaaga tgtaatgcaa gacgactggt    600
acacgtggcg aatgcacgtt gcacatcaga atgccatgta tgcgtggggg gttacgttca    660
attgtatgca tgcagtgcag tgactaccgg ccggctctcc tggatatgtc ggccatctct    720
ctctatatat tattaaaatg tcagctccct tctctaattt ggcgggagtt acatcagtgg    780
tactatgcag agttgcatac ttgcatatat atgcacatta ttaattaata actcgatctc    840
tcgtggacgg tggaacagtg ataatcatct cattgtcaat taattttgat caaagaaat     899
```

<210> SEQ ID NO 20
<211> LENGTH: 136
<212> TYPE: PRT
<213> ORGANISM: Zea mays
<220> FEATURE:
<223> OTHER INFORMATION: G3739 polypeptide

<400> SEQUENCE: 20

```
Met Asp Gly Asp Trp Ser Lys Asp Gly Gly Gly Glu Pro Thr Lys
1               5                   10                  15

Tyr Arg Gly Val Arg Arg Arg Pro Trp Gly Lys Tyr Ala Ala Glu Ile
            20                  25                  30

Arg Asp Ser Ser Arg His Gly Val Arg Ile Trp Leu Gly Thr Phe Asp
        35                  40                  45

Thr Ala Glu Glu Ala Ala Arg Ala Tyr Asp Arg Ser Ala Tyr Ser Met
    50                  55                  60

Arg Gly Ala Asn Ala Val Leu Asn Phe Pro Glu Asp Ala His Ala Tyr
65                  70                  75                  80

Ala Ala Ala Cys Arg Gly Ser Gly Ser Ser Ser Ser Ser Arg His
                85                  90                  95

Arg Gln Gln Gln Gln Gly Ser Gly Arg Asp Val Ile Glu Leu Glu
            100                 105                 110

Tyr Leu Asp Asp Glu Val Leu Gln Glu Met Leu Arg Asn His Glu Pro
        115                 120                 125

Ser Ser Ser Ala Arg Lys Lys Met
    130                 135
```

<210> SEQ ID NO 21
<211> LENGTH: 859
<212> TYPE: DNA
<213> ORGANISM: Triticum aestivum
<220> FEATURE:
<223> OTHER INFORMATION: G3736

<400> SEQUENCE: 21

```
gcacgaggct tcattctccc tcgttccatc caagctccac catccatcac tgatttgcac     60
ttacctagct actccgcaac ccccacttcc ggcttcttca tttctcacta ctagtacgta    120
gttgagatta tggagggcgg agaaggatcc ggtggcggcg gcgagccgac caagtaccgc    180
ggggtgcgcc gcaggccgtg gggcaagttc gccgcggaga tcgggactc gagccggcac    240 ggcgtgcgca tgtggctcgg caccttcgac accgccgagg aggccgcggc cgcctacgac    300
cgctccgcct actccatgcg cggccgcaac gccgtgctca acttccccga ccgggcgcac    360
```

```
gtctacgagg ccgaggccag gcgccagggc cagggctctt cgtcgtcggc gaggcagcag        420
aatcagcagc agcagcaggg gcagagcggg gtgatcgagt tcgagtacct ggacgacgac        480
gtgctgcagt ccatgctcca cgaccacgac aaatccaaca agtagatcga tggatcatcc        540
atccatccat ccatggatcg atccataata cctactgtat catcccggcc cggccggcaa        600
catcgacctg cgtgcatgcg cgggcgcgga tgcaatctac actacctacc tatgcattcc        660
ggccatatat taggtacgta gattatatgt gtacgagagc ctacgagctc gatgaagatc        720
gtacgtggtg cattctgatg catgaggatt ccatcgacac gaccctctac catatatttg        780
atgggtcgat cgagtaattt gcagccagta atccaatcga tgatatgggg ttttcaaaaa        840
aaaaaaaaaa aaaaaaaa                                                      859
```

<210> SEQ ID NO 22
<211> LENGTH: 131
<212> TYPE: PRT
<213> ORGANISM: Triticum aestivum
<220> FEATURE:
<223> OTHER INFORMATION: G3736 polypeptide

<400> SEQUENCE: 22

```
Met Glu Gly Gly Glu Gly Ser Gly Gly Gly Glu Pro Thr Lys Tyr
1               5                   10                  15

Arg Gly Val Arg Arg Arg Pro Trp Gly Lys Phe Ala Ala Glu Ile Arg
            20                  25                  30

Asp Ser Ser Arg His Gly Val Arg Met Trp Leu Gly Thr Phe Asp Thr
        35                  40                  45

Ala Glu Ala Ala Ala Ala Tyr Asp Arg Ser Ala Tyr Ser Met Arg
    50                  55                  60

Gly Arg Asn Ala Val Leu Asn Phe Pro Asp Arg Ala His Val Tyr Glu
65                  70                  75                  80

Ala Glu Ala Arg Arg Gln Gly Gln Gly Ser Ser Ser Ala Arg Gln
            85                  90                  95

Gln Asn Gln Gln Gln Gln Gly Gln Ser Gly Val Ile Glu Phe Glu
        100                 105                 110

Tyr Leu Asp Asp Asp Val Leu Gln Ser Met Leu His Asp His Asp Lys
    115                 120                 125

Ser Asn Lys
    130
```

<210> SEQ ID NO 23
<211> LENGTH: 514
<212> TYPE: DNA
<213> ORGANISM: Oryza sativa
<220> FEATURE:
<223> OTHER INFORMATION: G3381

<400> SEQUENCE: 23

```
atcgatcatc tgctacgaac tcaccctata tatatatact ccatcttagg agctgcttga         60
tcgatcgaca tatatataac taatggatca tcatcatcag cagcagcagc aggagggtga       120
gctggtggcc aagtacaggg gcgtgcggcg gcggccgtgg ggcaaattcg cggcagagat       180
ccgcgactcg agccggcacg gcgtccgcgt gtggctggga ccttcgaca cagccgagga        240 ggccgctcgc gcctacgacc gctccgccta ctccatgcgc ggcgccaacg ccgtcctcaa       300
cttccccgcc gacgcccaca tctacgcccg tcaactacac aataataacg ccgctgctgg       360
ctcttcatct tcctcttccg ccgccgccgc agcagccagg ccgccgccga tcgagttcga       420
```

```
gtacctcgat gaccacgtcc tgcaggagat gctccgagac cacaccacca acaagtagct    480
tactactcca ctatatatgc tgcctgctgc ttgt                                514
```

<210> SEQ ID NO 24
<211> LENGTH: 131
<212> TYPE: PRT
<213> ORGANISM: Oryza sativa
<220> FEATURE:
<223> OTHER INFORMATION: G3381 polypeptide

<400> SEQUENCE: 24

```
Met Asp His His His Gln Gln Gln Gln Glu Gly Glu Leu Val Ala
1               5                   10                  15

Lys Tyr Arg Gly Val Arg Arg Pro Trp Gly Lys Phe Ala Ala Glu
            20                  25                  30

Ile Arg Asp Ser Ser Arg His Gly Val Arg Val Trp Leu Gly Thr Phe
            35                  40                  45

Asp Thr Ala Glu Glu Ala Ala Arg Ala Tyr Asp Arg Ser Ala Tyr Ser
        50                  55                  60

Met Arg Gly Ala Asn Ala Val Leu Asn Phe Pro Ala Asp Ala His Ile
65                  70                  75                  80

Tyr Ala Arg Gln Leu His Asn Asn Asn Ala Ala Gly Ser Ser Ser
                85                  90                  95

Ser Ser Ser Ala Ala Ala Ala Ala Arg Pro Pro Ile Glu Phe
            100                 105                 110

Glu Tyr Leu Asp Asp His Val Leu Gln Glu Met Leu Arg Asp His Thr
        115                 120                 125

Thr Asn Lys
    130
```

<210> SEQ ID NO 25
<211> LENGTH: 882
<212> TYPE: DNA
<213> ORGANISM: Oryza sativa
<220> FEATURE:
<223> OTHER INFORMATION: G3737

<400> SEQUENCE: 25

```
acacatgcat cgatcattca tggatgccga attgccgcga tccgggcatt atttcgcgcc    60
aggagaccca agatcatcgt gtcgcccacg ctataaatag ctagctagct tgcctttatg   120
ttgcatatgc caactgctac atgcaggacg tctgaaacta tcattagtga cctgcagcgc   180
ctgcagtata tatatacaag tagtagtgag catggaggac gacaagaagg aggcggcgag   240
caagtaccgc ggcgtacgga ggcggccgtg gggcaaattc gcggcggaga tccgcgaccc   300
ggagcgcggc ggctcacgcg tctggcttgg cacgttcgac accgccgagg aggccgcgcg   360
agcgtacgac cgcgccgcat tcgccatgaa gggcgctatg ccgtgctca acttcccagg   420 caggacgagc agcaccggct cttcgtcgtc atcgtcatcc acgccgccag ctccggtgac   480
gacgagccgc cactgcgccg acacgacgga gaaggtggag cttgtgtacc ttgacgacaa   540
ggtgctcgac gagctccttg cggaggacta cagctaccgc aacaacaaca actactgatc   600
cggccgtcga tgaactgaga cggatcgaca tggggccggt cgtcggtacg ctcgctgaaa   660
cgagacccgg attgctatca ataagcaagc agaagaaaac cgtctcctat atatagcttc   720
ttctgttggc acaagcatat atgggcatgc atgacacatg ctactgtgaa ttgacgggtg   780
tgtgctgtgt gcagactact aaaccacgct tgcaagttgc acgtacgacg tggttgtcaa   840
```
gagcatgcag tccacgaagc agagaaaaac acctggttta tc                          882

<210> SEQ ID NO 26
<211> LENGTH: 128
<212> TYPE: PRT
<213> ORGANISM: Oryza sativa
<220> FEATURE:
<223> OTHER INFORMATION: G3737 polypeptide

<400> SEQUENCE: 26

Met Glu Asp Asp Lys Lys Glu Ala Ala Ser Lys Tyr Arg Gly Val Arg
1               5                   10                  15

Arg Arg Pro Trp Gly Lys Phe Ala Ala Glu Ile Arg Asp Pro Glu Arg
            20                  25                  30

Gly Gly Ser Arg Val Trp Leu Gly Thr Phe Asp Thr Ala Glu Glu Ala
        35                  40                  45

Ala Arg Ala Tyr Asp Arg Ala Ala Phe Ala Met Lys Gly Ala Met Ala
    50                  55                  60

Val Leu Asn Phe Pro Gly Arg Thr Ser Ser Thr Gly Ser Ser Ser Ser
65                  70                  75                  80

Ser Ser Ser Thr Pro Pro Ala Pro Val Thr Thr Ser Arg His Cys Ala
                85                  90                  95

Asp Thr Thr Glu Lys Val Glu Leu Val Tyr Leu Asp Asp Lys Val Leu
            100                 105                 110

Asp Glu Leu Leu Ala Glu Asp Tyr Ser Tyr Arg Asn Asn Asn Asn Tyr
        115                 120                 125

<210> SEQ ID NO 27
<211> LENGTH: 466
<212> TYPE: DNA
<213> ORGANISM: Oryza sativa
<220> FEATURE:
<223> OTHER INFORMATION: G3515

<400> SEQUENCE: 27
gtgtgcgagc ggttgcgtcc gcatggagga cgacaagagt aaggagggga atcgtcgtc        60
gtcgtaccgc ggcgtgcgga agcggccgtg gggcaagttc gcggcggaga tccgcgaccc      120
ggagcgcggg ggagcccgcg tgtggctcgg cacgttcgac accgcggagg aggccgcgcg      180
ggcgtacgac cgcgccgcat tcgccatgaa gggcgccacg gccatgctca acttcccggg      240
agatcatcat cacggcgccg caagcaggat gaccagcacc ggctcttctt cgtcctcctt      300
caccacgcct cctccggcga actcctccgc ggcggcgggc cgcggcggct ccgatcggac      360
gacggacaag gtggagctgg agtgcctcga cgacaaggtc ctggaggacc tcctcgcgga      420
gaccaactat cgtgataaga actactagct agctagctac tatggc                    466

<210> SEQ ID NO 28
<211> LENGTH: 141
<212> TYPE: PRT
<213> ORGANISM: Oryza sativa
<220> FEATURE:
<223> OTHER INFORMATION: G3515 polypeptide

<400> SEQUENCE: 28

Met Glu Asp Asp Lys Ser Lys Glu Gly Lys Ser Ser Ser Tyr Arg
1               5                   10                  15

Gly Val Arg Lys Arg Pro Trp Gly Lys Phe Ala Ala Glu Ile Arg Asp
            20                  25                  30

Pro Glu Arg Gly Gly Ala Arg Val Trp Leu Gly Thr Phe Asp Thr Ala

```
                  35                  40                  45

Glu Glu Ala Ala Arg Ala Tyr Asp Arg Ala Ala Phe Ala Met Lys Gly
 50                  55                  60

Ala Thr Ala Met Leu Asn Phe Pro Gly Asp His His His Gly Ala Ala
 65                  70                  75                  80

Ser Arg Met Thr Ser Thr Gly Ser Ser Ser Ser Phe Thr Thr Pro
                 85                  90                  95

Pro Pro Ala Asn Ser Ser Ala Ala Ala Gly Arg Gly Gly Ser Asp Arg
                100                 105                 110

Thr Thr Asp Lys Val Glu Leu Glu Cys Leu Asp Asp Lys Val Leu Glu
                115                 120                 125

Asp Leu Leu Ala Glu Thr Asn Tyr Arg Asp Lys Asn Tyr
                130                 135                 140

<210> SEQ ID NO 29
<211> LENGTH: 393
<212> TYPE: DNA
<213> ORGANISM: Zea mays
<220> FEATURE:
<223> OTHER INFORMATION: G3516

<400> SEQUENCE: 29
atggaggacg acaagaagga gggcaagtac cgcggcgtgc ggaagcggcc gtggggcaag    60
ttcgccgcgg agatccggga cccggagcgc ggcggctccc gcgtctggct cggcaccttc   120
gacaccgccg aggaggccgc cagggcctac gaccgcgccg cattcgccat gaagggcgcc   180
acggccgtgc tcaacttccc cgccagcgga ggatcgtcag ctggcgcggc tcccggcggc   240
cggaccagcg gcggctcctc ctcgtccacc acgtcggctc cggccagcag ggggagggcc   300
cgtgttcccg actcggagaa ggtggagctg gagtgcctcg acgacagggt cttggaagag   360
ctgctcgcgg aagacaagta caacaagaac taa                                393

<210> SEQ ID NO 30
<211> LENGTH: 130
<212> TYPE: PRT
<213> ORGANISM: Zea mays
<220> FEATURE:
<223> OTHER INFORMATION: G3516 polypeptide

<400> SEQUENCE: 30

Met Glu Asp Asp Lys Lys Glu Gly Lys Tyr Arg Gly Val Arg Lys Arg
 1               5                  10                  15

Pro Trp Gly Lys Phe Ala Ala Glu Ile Arg Asp Pro Glu Arg Gly Gly
                 20                  25                  30

Ser Arg Val Trp Leu Gly Thr Phe Asp Thr Ala Glu Glu Ala Ala Arg
             35                  40                  45

Ala Tyr Asp Arg Ala Ala Phe Ala Met Lys Gly Ala Thr Ala Val Leu
 50                  55                  60

Asn Phe Pro Ala Ser Gly Gly Ser Ala Gly Ala Ala Pro Gly Gly
 65                  70                  75                  80

Arg Thr Ser Gly Gly Ser Ser Ser Thr Thr Ser Ala Pro Ala Ser
             85                  90                  95

Arg Gly Arg Ala Arg Val Pro Asp Ser Glu Lys Val Glu Leu Glu Cys
                100                 105                 110

Leu Asp Asp Arg Val Leu Glu Glu Leu Leu Ala Glu Asp Lys Tyr Asn
                115                 120                 125

Lys Asn
```

<210> SEQ ID NO 31
<211> LENGTH: 579
<212> TYPE: DNA
<213> ORGANISM: Oryza sativa
<220> FEATURE:
<223> OTHER INFORMATION: G3380

<400> SEQUENCE: 31

```
ggtccgatcc gtaacagtag tagctagtta atttgattat tgtccgtccg cggccggtca      60
gtggtcgcaa tcgatcgatc gatatcatgg acggcgacgg cggcggcgga tgggacgatc     120
agggcaacgg cggcggcgag acgaccaagt accgtggcgt gcgtcgccgg ccttctggca     180
agttcgcggc ggagatccgt gactccagca ggcagagcgt ccgcgtctgg ctgggaacct     240
tcgacaccgc cgaggaggct gcgcgggctt acgaccgcgc cgcctacgcc atgcgcggcc     300
acctcgccgt cctcaacttc cctgctgagg cgcgcaacta cgtgcgggga tcaggctcgt     360
cgtcctcgtc ccgacagcat cagcagcggc aggtgatcga gctggagtgc ctagacgacc     420
aagtgctgca agagatgctc aagggtggcg acgatcagta caggtcagca gctgggagca     480
agaggaataa ctactagcta tatatgctgc taacctactt acaatcgcga tacatatcga     540
ggtttgggga ttttcttctc acctgtgtgc agaggctgc                            579
```

<210> SEQ ID NO 32
<211> LENGTH: 136
<212> TYPE: PRT
<213> ORGANISM: Oryza sativa
<220> FEATURE:
<223> OTHER INFORMATION: G3380 polypeptide

<400> SEQUENCE: 32

```
Met Asp Gly Asp Gly Gly Gly Gly Trp Asp Asp Gln Gly Asn Gly Gly
  1               5                  10                  15

Gly Glu Thr Thr Lys Tyr Arg Gly Val Arg Arg Pro Ser Gly Lys
                 20                  25                  30

Phe Ala Ala Glu Ile Arg Asp Ser Ser Arg Gln Ser Val Arg Val Trp
             35                  40                  45

Leu Gly Thr Phe Asp Thr Ala Glu Glu Ala Arg Ala Tyr Asp Arg
         50                  55                  60

Ala Ala Tyr Ala Met Arg Gly His Leu Ala Val Leu Asn Phe Pro Ala
 65                  70                  75                  80

Glu Ala Arg Asn Tyr Val Arg Gly Ser Gly Ser Ser Ser Ser Arg
                 85                  90                  95

Gln His Gln Gln Arg Gln Val Ile Glu Leu Glu Cys Leu Asp Asp Gln
            100                 105                 110

Val Leu Gln Glu Met Leu Lys Gly Gly Asp Asp Gln Tyr Arg Ser Ala
        115                 120                 125

Ala Gly Ser Lys Arg Asn Asn Tyr
    130                 135
```

<210> SEQ ID NO 33
<211> LENGTH: 918
<212> TYPE: DNA
<213> ORGANISM: Zea mays
<220> FEATURE:
<223> OTHER INFORMATION: G3794

<400> SEQUENCE: 33

```
attacttgtg cacttgggtg cagtgcctgc agtataatca agttagggtt taaaagaacc    60
tcgaccgcga tcgtatatag atccagatta tcattagtta ttagaccact gtgatatcga   120
tggacgacgg cggcgagcca accaagtacc gcggcgtgcg gcgccggccg tcggggaagt   180
tcgccgccga gatccgcgac tccagccggc agagcgtgcg catgtggctg ggcaccttcg   240
acacggccga ggaggccgca agggcgtacg accgcgcggc ctacgccatg cgcggccaaa   300
tcgccgtgct caacttcccc gccgaggcgc gcaactacgt gcgcgcgggg tcgtcgtcgt   360
cccgccagca gcagcaggga ggaggaggag gaggaggaag tggcggcggc gccggtcagc   420
aggtgatcga gctggagtgc ctggacgatc aggtgctgca ggagatgctc aagggcggcg   480
acgggaaaaa atagttgtta gcgtatctga tcacaggtgc acgtgttgaa actgattatg   540
accaggcgat cgatcccatc ttgtgcatgc ggcctgccaa agttgctggg tcttctcatc   600
gacctatata tatgcttc tcgatccata tatatcat aaatgcatgc agggtgcatg   660
catgtaccaa gtttggaatt ataatgctct tggtgctgaa ttgaagtata ctagtatata   720
tagtgtgatc catgtattga aaaggttgtt ttgcttaatc gcgtcatgat tgcacacgtg   780
cttgtttctg cttaaacaac ccatatatat agccggctct ggcctttgtc aagtctgcaa   840
tccttataca tcgttggtaa ttcatgcatg agttctatgt aactgcaatt tagataaatt   900
gtagctaata taatagtc                                                918

<210> SEQ ID NO 34
<211> LENGTH: 124
<212> TYPE: PRT
<213> ORGANISM: Zea mays
<220> FEATURE:
<223> OTHER INFORMATION: G3794 polypeptide

<400> SEQUENCE: 34

Met Asp Asp Gly Gly Glu Pro Thr Lys Tyr Arg Gly Val Arg Arg Arg
1               5                   10                  15

Pro Ser Gly Lys Phe Ala Ala Glu Ile Arg Asp Ser Ser Arg Gln Ser
            20                  25                  30

Val Arg Met Trp Leu Gly Thr Phe Asp Thr Ala Glu Glu Ala Ala Arg
        35                  40                  45

Ala Tyr Asp Arg Ala Ala Tyr Ala Met Arg Gly Gln Ile Ala Val Leu
    50                  55                  60

Asn Phe Pro Ala Glu Ala Arg Asn Tyr Val Arg Gly Gly Ser Ser Ser
65                  70                  75                  80

Ser Arg Gln Gln Gln Gln Gly Gly Gly Gly Gly Gly Ser Gly Gly
            85                  90                  95

Gly Ala Gly Gln Gln Val Ile Glu Leu Glu Cys Leu Asp Asp Gln Val
            100                 105                 110

Leu Gln Glu Met Leu Lys Gly Gly Asp Gly Lys Lys
        115                 120

<210> SEQ ID NO 35
<211> LENGTH: 653
<212> TYPE: DNA
<213> ORGANISM: Medicago truncatula
<220> FEATURE:
<221> NAME/KEY: misc_feature
<222> LOCATION: (605)..(605)
<223> OTHER INFORMATION: n is a, c, g, or t
<220> FEATURE:
<221> NAME/KEY: misc_feature
<222> LOCATION: (610)..(610)
<223> OTHER INFORMATION: n is a, c, g, or t
```

```
<220> FEATURE:
<221> NAME/KEY: misc_feature
<222> LOCATION: (615)..(615)
<223> OTHER INFORMATION: n is a, c, g, or t
<220> FEATURE:
<221> NAME/KEY: misc_feature
<222> LOCATION: (625)..(625)
<223> OTHER INFORMATION: n is a, c, g, or t
<220> FEATURE:
<221> NAME/KEY: misc_feature
<222> LOCATION: (647)..(647)
<223> OTHER INFORMATION: n is a, c, g, or t
<220> FEATURE:
<221> NAME/KEY: misc_feature
<222> LOCATION: (652)..(652)
<223> OTHER INFORMATION: n is a, c, g, or t
<220> FEATURE:
<223> OTHER INFORMATION: G3735

<400> SEQUENCE: 35
ctaatccttc atactaaaga aaacatagac ttataacaaa atatattatta tttacttcgt    60 atattttgt gtttcaaatt aatggaggga gatcataaat tagtttcaaa ttcaacaaat    120
ggaaatggaa atggaaatgg aaattcagat caaataaagt atagaggaat tcgtagaaga    180
ccatggggaa aatttgcagc agaaattcgt gacccaacaa ggaaagggac aagaatatgg    240
cttggaacat tgatactgc tgaacaagct gcaagagctt atgatgctgc tgcttttcat    300
tttcgtggtc atagagctat tctcaatttc cctaatgaat atcaagctcc taattcatct    360
tcttcattac ctatgcctct tactatgcct ccaccacctt cttctaatcc acctccttct    420
tcttcttctt cttcctcttt ttcttcttac accgttgatg atggttttga tgagcttgaa    480
ttcttggata ataagttgct tcaagaactt cttcaagatg aacacaata gttaactatt    540 gaagatcaag tggcatgaaa tgtattggtg tcattaat tttctcttca ttaatttatt    600
ttggnttggn tatgnatctc atttntatga ataaatgaga atggggnatt ana           653

<210> SEQ ID NO 36
<211> LENGTH: 149
<212> TYPE: PRT
<213> ORGANISM: Medicago truncatula
<220> FEATURE:
<223> OTHER INFORMATION: G3735 polypeptide

<400> SEQUENCE: 36

Met Glu Gly Asp His Lys Leu Val Ser Asn Ser Thr Asn Gly Asn Gly
1               5                   10                  15

Asn Gly Asn Gly Asn Ser Asp Gln Ile Lys Tyr Arg Gly Ile Arg Arg
            20                  25                  30

Arg Pro Trp Gly Lys Phe Ala Ala Glu Ile Arg Asp Pro Thr Arg Lys
        35                  40                  45

Gly Thr Arg Ile Trp Leu Gly Thr Phe Asp Thr Ala Glu Gln Ala Ala
    50                  55                  60

Arg Ala Tyr Asp Ala Ala Ala Phe His Phe Arg Gly His Arg Ala Ile
65                  70                  75                  80

Leu Asn Phe Pro Asn Glu Tyr Gln Ala Pro Asn Ser Ser Ser Leu
                85                  90                  95

Pro Met Pro Leu Thr Met Pro Pro Pro Ser Ser Asn Pro Pro
            100                 105                 110

Ser Ser Ser Ser Ser Ser Ser Phe Ser Ser Tyr Thr Val Asp Asp Gly
        115                 120                 125

Phe Asp Glu Leu Glu Phe Leu Asp Asn Lys Leu Leu Gln Glu Leu Leu
    130                 135                 140
```

Gln Asp Gly Thr Gln
145

<210> SEQ ID NO 37
<211> LENGTH: 16
<212> TYPE: PRT
<213> ORGANISM: Arabidopsis thaliana
<220> FEATURE:
<223> OTHER INFORMATION: AtERF98 (G1792) EDLL domain

<400> SEQUENCE: 37

Val Phe Glu Phe Glu Tyr Leu Asp Asp Lys Val Leu Glu Glu Leu Leu
1               5                   10                  15

<210> SEQ ID NO 38
<211> LENGTH: 16
<212> TYPE: PRT
<213> ORGANISM: Arabidopsis thaliana
<220> FEATURE:
<223> OTHER INFORMATION: G1795 EDLL domain

<400> SEQUENCE: 38

Val Phe Glu Phe Glu Tyr Leu Asp Asp Ser Val Leu Glu Glu Leu Leu
1               5                   10                  15

<210> SEQ ID NO 39
<211> LENGTH: 16
<212> TYPE: PRT
<213> ORGANISM: Arabidopsis thaliana
<220> FEATURE:
<223> OTHER INFORMATION: G30 EDLL domain

<400> SEQUENCE: 39

Val Phe Glu Phe Glu Tyr Leu Asp Asp Ser Val Leu Asp Glu Leu Leu
1               5                   10                  15

<210> SEQ ID NO 40
<211> LENGTH: 16
<212> TYPE: PRT
<213> ORGANISM: Arabidopsis thaliana
<220> FEATURE:
<223> OTHER INFORMATION: G1791 EDLL domain

<400> SEQUENCE: 40

Val Ile Glu Phe Glu Tyr Leu Asp Asp Ser Leu Leu Glu Glu Leu Leu
1               5                   10                  15

<210> SEQ ID NO 41
<211> LENGTH: 16
<212> TYPE: PRT
<213> ORGANISM: Glycine max
<220> FEATURE:
<223> OTHER INFORMATION: G3520 EDLL domain

<400> SEQUENCE: 41

Val Ile Glu Phe Glu Cys Leu Asp Asp Lys Leu Leu Glu Asp Leu Leu
1               5                   10                  15

<210> SEQ ID NO 42
<211> LENGTH: 16
<212> TYPE: PRT
<213> ORGANISM: Glycine max
<220> FEATURE:
<223> OTHER INFORMATION: G3519 EDLL domain

<400> SEQUENCE: 42

```
Thr Phe Glu Leu Glu Tyr Leu Asp Asn Lys Leu Leu Glu Glu Leu Leu
1               5                   10                  15
```

<210> SEQ ID NO 43
<211> LENGTH: 16
<212> TYPE: PRT
<213> ORGANISM: Oryza sativa
<220> FEATURE:
<223> OTHER INFORMATION: G3383 EDLL domain

<400> SEQUENCE: 43

```
Lys Ile Glu Phe Glu Tyr Leu Asp Asp Lys Val Leu Asp Asp Leu Leu
1               5                   10                  15
```

<210> SEQ ID NO 44
<211> LENGTH: 16
<212> TYPE: PRT
<213> ORGANISM: Zea mays
<220> FEATURE:
<223> OTHER INFORMATION: G3517 EDLL domain

<400> SEQUENCE: 44

```
Val Ile Glu Phe Glu Tyr Leu Asp Asp Glu Val Leu Gln Glu Met Leu
1               5                   10                  15
```

<210> SEQ ID NO 45
<211> LENGTH: 16
<212> TYPE: PRT
<213> ORGANISM: Glycine max
<220> FEATURE:
<223> OTHER INFORMATION: G3518 EDLL domain

<400> SEQUENCE: 45

```
Thr Phe Glu Leu Glu Tyr Phe Asp Asn Lys Leu Leu Glu Glu Leu Leu
1               5                   10                  15
```

<210> SEQ ID NO 46
<211> LENGTH: 16
<212> TYPE: PRT
<213> ORGANISM: Zea mays
<220> FEATURE:
<223> OTHER INFORMATION: G3739 EDLL domain

<400> SEQUENCE: 46

```
Val Ile Glu Leu Glu Tyr Leu Asp Asp Glu Val Leu Gln Glu Met Leu
1               5                   10                  15
```

<210> SEQ ID NO 47
<211> LENGTH: 16
<212> TYPE: PRT
<213> ORGANISM: Triticum aestivum
<220> FEATURE:
<223> OTHER INFORMATION: G3736 EDLL domain

<400> SEQUENCE: 47

```
Val Ile Glu Phe Glu Tyr Leu Asp Asp Asp Val Leu Gln Ser Met Leu
1               5                   10                  15
```

<210> SEQ ID NO 48
<211> LENGTH: 16
<212> TYPE: PRT
<213> ORGANISM: Oryza sativa
<220> FEATURE:
<223> OTHER INFORMATION: G3381 EDLL domain

<400> SEQUENCE: 48

```
Pro Ile Glu Phe Glu Tyr Leu Asp Asp His Val Leu Gln Glu Met Leu
```

```
<210> SEQ ID NO 49
<211> LENGTH: 16
<212> TYPE: PRT
<213> ORGANISM: Oryza sativa
<220> FEATURE:
<223> OTHER INFORMATION: G3737 EDLL domain

<400> SEQUENCE: 49

Lys Val Glu Leu Val Tyr Leu Asp Asp Lys Val Leu Asp Glu Leu Leu
1               5                   10                  15

<210> SEQ ID NO 50
<211> LENGTH: 16
<212> TYPE: PRT
<213> ORGANISM: Oryza sativa
<220> FEATURE:
<223> OTHER INFORMATION: G3515 EDLL domain

<400> SEQUENCE: 50

Lys Val Glu Leu Glu Cys Leu Asp Asp Lys Val Leu Glu Asp Leu Leu
1               5                   10                  15

<210> SEQ ID NO 51
<211> LENGTH: 16
<212> TYPE: PRT
<213> ORGANISM: Zea mays
<220> FEATURE:
<223> OTHER INFORMATION: G3516 EDLL domain

<400> SEQUENCE: 51

Lys Val Glu Leu Glu Cys Leu Asp Asp Arg Val Leu Glu Glu Leu Leu
1               5                   10                  15

<210> SEQ ID NO 52
<211> LENGTH: 16
<212> TYPE: PRT
<213> ORGANISM: Oryza sativa
<220> FEATURE:
<223> OTHER INFORMATION: G3380 EDLL domain

<400> SEQUENCE: 52

Val Ile Glu Leu Glu Cys Leu Asp Asp Gln Val Leu Gln Glu Met Leu
1               5                   10                  15

<210> SEQ ID NO 53
<211> LENGTH: 16
<212> TYPE: PRT
<213> ORGANISM: Zea mays
<220> FEATURE:
<223> OTHER INFORMATION: G3794 EDLL domain

<400> SEQUENCE: 53

Val Ile Glu Leu Glu Cys Leu Asp Asp Gln Val Leu Gln Glu Met Leu
1               5                   10                  15

<210> SEQ ID NO 54
<211> LENGTH: 14
<212> TYPE: PRT
<213> ORGANISM: Medicago truncatula
<220> FEATURE:
<223> OTHER INFORMATION: G3735 EDLL domain

<400> SEQUENCE: 54

Glu Leu Glu Phe Leu Asp Asn Lys Leu Leu Gln Glu Leu Leu
1               5                   10
```

```
<210> SEQ ID NO 55
<211> LENGTH: 14
<212> TYPE: PRT
<213> ORGANISM: Arabidopsis thaliana
<220> FEATURE:
<221> NAME/KEY: misc_feature
<222> LOCATION: (2)..(5)
<223> OTHER INFORMATION: Xaa can be any naturally occurring amino acid
<220> FEATURE:
<221> NAME/KEY: misc_feature
<222> LOCATION: (7)..(9)
<223> OTHER INFORMATION: Xaa can be any naturally occurring amino acid
<220> FEATURE:
<221> NAME/KEY: misc_feature
<222> LOCATION: (11)..(13)
<223> OTHER INFORMATION: Xaa can be any naturally occurring amino acid
<220> FEATURE:
<223> OTHER INFORMATION: EDLL domain

<400> SEQUENCE: 55

Glu Xaa Xaa Xaa Xaa Asp Xaa Xaa Xaa Leu Xaa Xaa Xaa Leu
1               5                   10

<210> SEQ ID NO 56
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Leu or Phe
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
<223> OTHER INFORMATION: Xaa can be Asp or Asn
<220> FEATURE:
<221> NAME/KEY: misc_feature
<222> LOCATION: (8)..(9)
<223> OTHER INFORMATION: Xaa can be any naturally occurring amino acid
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain

<400> SEQUENCE: 56

Glu Xaa Xaa Xaa Xaa Asp Xaa Xaa Xaa Leu Xaa Xaa Xaa Leu
1               5                   10

<210> SEQ ID NO 57
<211> LENGTH: 75
<212> TYPE: DNA
<213> ORGANISM: Arabidopsis thaliana
<220> FEATURE:
<223> OTHER INFORMATION: fragment encoding G1792 EDLL domain used for
      cloning

<400> SEQUENCE: 57
gaagttttcg agtttgagta tttggacgat aaggttcttg aagaacttct tgattcagaa      60
```
gaaaggaaga gataa                                                      75

<210> SEQ ID NO 58
<211> LENGTH: 144
<212> TYPE: DNA
<213> ORGANISM: Arabidopsis thaliana
<220> FEATURE:
<223> OTHER INFORMATION: fragment encoding G1792 EDLL (2X) domain used
      for cloning

<400> SEQUENCE: 58
gaagttttcg agtttgagta tttggacgat aaggttcttg aagaacttct tgattcagaa      60
gaaaggaaga gagaagtttt cgagtttgag tatttggacg ataaggttct tgaagaactt     120
cttgattcag aagaaaggaa gaga                                            144

<210> SEQ ID NO 59
<211> LENGTH: 63
<212> TYPE: DNA
<213> ORGANISM: Medicago truncatula
<220> FEATURE:
<223> OTHER INFORMATION: fragment encoding G3735 EDLL domain used for
      cloning

<400> SEQUENCE: 59
tttgatgagc ttgaattctt ggataataag ttgcttcaag aacttcttca agatggaaca      60
caa                                                                   63

<210> SEQ ID NO 60
<211> LENGTH: 72
<212> TYPE: DNA
<213> ORGANISM: Oryza sativa
<220> FEATURE:
<223> OTHER INFORMATION: cloned sequence fragment encoding G3737 EDLL
      domain

<400> SEQUENCE: 60
aaggtggagc ttgtgtacct tgacgacaag gtgctcgacg agctccttgc ggaggactac      60
agctaccgca ac                                                         72

<210> SEQ ID NO 61
<211> LENGTH: 72
<212> TYPE: DNA
<213> ORGANISM: Arabidopsis thaliana
<220> FEATURE:
<223> OTHER INFORMATION: fragment encoding G30 EDLL domain used for
      cloning

<400> SEQUENCE: 61
gtttttgagt ttgagtactt ggacgatagc gttttggatg aacttcttga atatggagag      60
aactataaca ag                                                         72

<210> SEQ ID NO 62
<211> LENGTH: 72
<212> TYPE: DNA
<213> ORGANISM: Glycine max
<220> FEATURE:
<223> OTHER INFORMATION: fragment encoding G3518 EDLL domain used for
      cloning

<400> SEQUENCE: 62
acttttgagt tggagtactt cgataataag ttgctcgagg aactccttca gatgcaagat      60
aacagacact tc                                                         72

<210> SEQ ID NO 63
<211> LENGTH: 72
<212> TYPE: DNA
<213> ORGANISM: Zea mays
<220> FEATURE:
<223> OTHER INFORMATION: fragment encoding G3739 EDLL domain used for
      cloning

<400> SEQUENCE: 63
gtgatcgagc tcgagtacct cgacgacgag gtgctgcagg agatgctcag gaaccacgag    60
ccgtcgtcgt ct                                                        72

<210> SEQ ID NO 64
<211> LENGTH: 16
<212> TYPE: PRT
<213> ORGANISM: Arabidopsis thaliana
<220> FEATURE:
<223> OTHER INFORMATION: G1752 subsequence

<400> SEQUENCE: 64

Leu Val Val Phe Glu Asp Leu Gly Ala Glu Tyr Leu Glu Gln Leu Leu
1               5                   10                  15

<210> SEQ ID NO 65
<211> LENGTH: 16
<212> TYPE: PRT
<213> ORGANISM: Arabidopsis thaliana
<220> FEATURE:
<223> OTHER INFORMATION: G26 subsequence

<400> SEQUENCE: 65

Ser Ser Ser Ser Ser Ser Leu Asn His Gln Gly Leu Arg Pro Asn Leu
1               5                   10                  15

<210> SEQ ID NO 66
<211> LENGTH: 16
<212> TYPE: PRT
<213> ORGANISM: Arabidopsis thaliana
<220> FEATURE:
<223> OTHER INFORMATION: G22 subsequence

<400> SEQUENCE: 66

Glu Leu Asp Phe Thr Val Asp Gln Phe Tyr Phe Asp Gly Ser Leu Leu
1               5                   10                  15

<210> SEQ ID NO 67
<211> LENGTH: 14
<212> TYPE: PRT
<213> ORGANISM: Arabidopsis thaliana
<220> FEATURE:
<223> OTHER INFORMATION: G1006 subsequence

<400> SEQUENCE: 67

Lys Cys Glu Val Gly Asp Glu Thr Arg Val Asp Glu Leu Leu
1               5                   10

<210> SEQ ID NO 68
<211> LENGTH: 16
<212> TYPE: PRT
<213> ORGANISM: Arabidopsis thaliana
<220> FEATURE:
<223> OTHER INFORMATION: G28 subsequence

<400> SEQUENCE: 68

Thr Val Lys Cys Glu Val Val Glu Val Ala Arg Gly Asp Arg Leu Leu

-continued

```
1               5                   10                  15

<210> SEQ ID NO 69
<211> LENGTH: 16
<212> TYPE: PRT
<213> ORGANISM: Arabidopsis thaliana
<220> FEATURE:
<223> OTHER INFORMATION: G1751 subsequence

<400> SEQUENCE: 69

Cys Asn Met Glu Glu Trp Met Asn Met Met Met Met Met Asp Phe Gly
1               5                   10                  15

<210> SEQ ID NO 70
<211> LENGTH: 16
<212> TYPE: PRT
<213> ORGANISM: Arabidopsis thaliana
<220> FEATURE:
<223> OTHER INFORMATION: G45 subsequence

<400> SEQUENCE: 70

Leu Phe Glu Phe Glu Asp Leu Gly Ser Asp Tyr Leu Glu Thr Leu Leu
1               5                   10                  15

<210> SEQ ID NO 71
<211> LENGTH: 16
<212> TYPE: PRT
<213> ORGANISM: Arabidopsis thaliana
<220> FEATURE:
<223> OTHER INFORMATION: G1266 subsequence

<400> SEQUENCE: 71

Val Val Val Phe Glu Asp Leu Gly Glu Gln Tyr Leu Glu Glu Leu Leu
1               5                   10                  15

<210> SEQ ID NO 72
<211> LENGTH: 15
<212> TYPE: PRT
<213> ORGANISM: Arabidopsis thaliana
<220> FEATURE:
<223> OTHER INFORMATION: G2512 subsequence

<400> SEQUENCE: 72

Leu Val Val Leu Glu Asp Leu Gly Ala Glu Tyr Leu Glu Glu Leu
1               5                   10                  15

<210> SEQ ID NO 73
<211> LENGTH: 141
<212> TYPE: PRT
<213> ORGANISM: Arabidopsis thaliana
<220> FEATURE:
<223> OTHER INFORMATION: G481 polypeptide

<400> SEQUENCE: 73

Met Ala Asp Thr Pro Ser Ser Pro Ala Gly Asp Gly Gly Glu Ser Gly
1               5                   10                  15

Gly Ser Val Arg Glu Gln Asp Arg Tyr Leu Pro Ile Ala Asn Ile Ser
                20                  25                  30

Arg Ile Met Lys Lys Ala Leu Pro Pro Asn Gly Lys Ile Gly Lys Asp
            35                  40                  45

Ala Lys Asp Thr Val Gln Glu Cys Val Ser Glu Phe Ile Ser Phe Ile
        50                  55                  60

Thr Ser Glu Ala Ser Asp Lys Cys Gln Lys Glu Lys Arg Lys Thr Val
65                  70                  75                  80
```

```
Asn Gly Asp Asp Leu Leu Trp Ala Met Ala Thr Leu Gly Phe Glu Asp
                85                  90                  95

Tyr Leu Glu Pro Leu Lys Ile Tyr Leu Ala Arg Tyr Arg Glu Leu Glu
            100                 105                 110

Gly Asp Asn Lys Gly Ser Gly Lys Ser Gly Asp Gly Ser Asn Arg Asp
        115                 120                 125

Ala Gly Gly Val Ser Gly Glu Met Pro Ser Trp
    130                 135                 140

<210> SEQ ID NO 74
<211> LENGTH: 199
<212> TYPE: PRT
<213> ORGANISM: Arabidopsis thaliana
<220> FEATURE:
<223> OTHER INFORMATION: G483 polypeptide

<400> SEQUENCE: 74

Met Glu Gln Ser Glu Glu Gly Gln Gln Gln Gln Gln Gln Gly Val Met
1               5                   10                  15

Asp Tyr Val Pro Pro His Ala Tyr Gln Ser Gly Pro Val Asn Ala Ala
            20                  25                  30

Ser His Met Ala Phe Gln Ala His His Phe His His His His Gln
        35                  40                  45

Gln Gln Gln Gln Gln Leu Gln Met Phe Trp Ala Asn Gln Met Gln
    50                  55                  60

Glu Ile Glu His Thr Thr Asp Phe Lys Asn His Thr Leu Pro Leu Ala
65                  70                  75                  80

Arg Ile Lys Lys Ile Met Lys Ala Asp Glu Asp Val Arg Met Ile Ser
                85                  90                  95

Ala Glu Ala Pro Val Ile Phe Ala Lys Ala Cys Glu Met Phe Ile Leu
            100                 105                 110

Glu Leu Thr Leu Arg Ala Trp Ile His Thr Glu Glu Asn Lys Arg Arg
        115                 120                 125

Thr Leu Gln Lys Asn Asp Ile Ala Ala Ala Ile Ser Arg Thr Asp Val
    130                 135                 140

Phe Asp Phe Leu Val Asp Ile Ile Pro Arg Asp Glu Leu Lys Glu Glu
145                 150                 155                 160

Gly Leu Gly Val Thr Lys Gly Thr Ile Pro Ser Val Val Gly Ser Pro
                165                 170                 175

Pro Tyr Tyr Tyr Leu Gln Gln Gly Met Met Gln His Trp Pro Gln
            180                 185                 190

Glu Gln His Pro Asp Glu Ser
        195

<210> SEQ ID NO 75
<211> LENGTH: 234
<212> TYPE: PRT
<213> ORGANISM: Arabidopsis thaliana
<220> FEATURE:
<223> OTHER INFORMATION: G715 polypeptide

<400> SEQUENCE: 75

Met Asp Thr Asn Asn Gln Gln Pro Pro Ser Ala Ala Gly Ile Pro
1               5                   10                  15

Pro Pro Pro Pro Gly Thr Thr Ile Ser Ala Ala Gly Gly Gly Ala Ser
            20                  25                  30

Tyr His His Leu Leu Gln Gln Gln Gln Gln Leu Gln Leu Phe Trp
        35                  40                  45
```

```
Thr Tyr Gln Arg Gln Glu Ile Glu Gln Val Asn Asp Phe Lys Asn His
 50                  55                  60

Gln Leu Pro Leu Ala Arg Ile Lys Lys Ile Met Lys Ala Asp Glu Asp
 65                  70                  75                  80

Val Arg Met Ile Ser Ala Glu Ala Pro Ile Leu Phe Ala Lys Ala Cys
                 85                  90                  95

Glu Leu Phe Ile Leu Glu Leu Thr Ile Arg Ser Trp Leu His Ala Glu
                100                 105                 110

Glu Asn Lys Arg Arg Thr Leu Gln Lys Asn Asp Ile Ala Ala Ala Ile
                115                 120                 125

Thr Arg Thr Asp Ile Phe Asp Phe Leu Val Asp Ile Val Pro Arg Asp
                130                 135                 140

Glu Ile Lys Asp Glu Ala Ala Val Leu Gly Gly Gly Met Val Val Ala
145                 150                 155                 160

Pro Thr Ala Ser Gly Val Pro Tyr Tyr Tyr Pro Pro Met Gly Gln Pro
                165                 170                 175

Ala Gly Pro Gly Gly Met Met Ile Gly Arg Pro Ala Met Asp Pro Asn
                180                 185                 190

Gly Val Tyr Val Gln Pro Pro Ser Gln Ala Trp Gln Ser Val Trp Gln
                195                 200                 205

Thr Ser Thr Gly Thr Gly Asp Asp Val Ser Tyr Gly Ser Gly Ser
                210                 215                 220

Ser Gly Gln Gly Asn Leu Asp Gly Gln Gly
225                 230
```

```
<210> SEQ ID NO 76
<211> LENGTH: 48
<212> TYPE: DNA
<213> ORGANISM: Arabidopsis thaliana
<220> FEATURE:
<223> OTHER INFORMATION: DNA encoding G1792 EDLL domain

<400> SEQUENCE: 76
gttttcgagt tgagtatttt ggacgataag gttcttgaag aacttctt         48

<210> SEQ ID NO 77
<211> LENGTH: 48
<212> TYPE: DNA
<213> ORGANISM: Arabidopsis thaliana
<220> FEATURE:
<223> OTHER INFORMATION: DNA encoding G1795 EDLL domain

<400> SEQUENCE: 77 gttttttgaat ttgagtactt ggatgatagt gttttggagg agctccctt        48

<210> SEQ ID NO 78
<211> LENGTH: 48
<212> TYPE: DNA
<213> ORGANISM: Arabidopsis thaliana
<220> FEATURE:
<223> OTHER INFORMATION: DNA encoding G30 EDLL domain

<400> SEQUENCE: 78 gttttttgagt ttgagtactt ggacgatagc gttttggatg aacttctt        48

<210> SEQ ID NO 79
<211> LENGTH: 48
<212> TYPE: DNA
<213> ORGANISM: Arabidopsis thaliana
<220> FEATURE:
```

<223> OTHER INFORMATION: DNA encoding G1791 EDLL domain

<400> SEQUENCE: 79
gttattgagt tcgagtattt ggatgatagt ttattggagg agctttta    48

<210> SEQ ID NO 80
<211> LENGTH: 48
<212> TYPE: DNA
<213> ORGANISM: Glycine max
<220> FEATURE:
<223> OTHER INFORMATION: DNA encoding G3520 EDLL domain

<400> SEQUENCE: 80
gttattgagt tcgagtgctt ggatgacaaa ttgttagagg accttctt    48

<210> SEQ ID NO 81
<211> LENGTH: 48
<212> TYPE: DNA
<213> ORGANISM: Glycine max
<220> FEATURE:
<223> OTHER INFORMATION: DNA encoding G3519 EDLL domain

<400> SEQUENCE: 81 actttttgagt tggagtactt ggataataag ttgctcgagg aactcctt    48

<210> SEQ ID NO 82
<211> LENGTH: 48
<212> TYPE: DNA
<213> ORGANISM: Oryza sativa
<220> FEATURE:
<223> OTHER INFORMATION: DNA encoding G3383 EDLL domain

<400> SEQUENCE: 82
aagatcgagt tcgagtacct cgacgacaag gtgctcgacg atctcctc    48

<210> SEQ ID NO 83
<211> LENGTH: 48
<212> TYPE: DNA
<213> ORGANISM: Zea mays
<220> FEATURE:
<223> OTHER INFORMATION: DNA encoding G3517 EDLL domain

<400> SEQUENCE: 83
gtgatcgagt ttgagtacct cgacgacgag gtgctgcagg agatgctc    48

<210> SEQ ID NO 84
<211> LENGTH: 48
<212> TYPE: DNA
<213> ORGANISM: Glycine max
<220> FEATURE:
<223> OTHER INFORMATION: DNA encoding G3518 EDLL domain

<400> SEQUENCE: 84 actttttgagt tggagtactt cgataataag ttgctcgagg aactcctt    48

<210> SEQ ID NO 85
<211> LENGTH: 48
<212> TYPE: DNA
<213> ORGANISM: Zea mays
<220> FEATURE:
<223> OTHER INFORMATION: DNA encoding G3739 EDLL domain

<400> SEQUENCE: 85
gtgatcgagc tcgagtacct cgacgacgag gtgctgcagg agatgctc    48

<210> SEQ ID NO 86
<211> LENGTH: 48
<212> TYPE: DNA
<213> ORGANISM: Triticum aestivum
<220> FEATURE:
<223> OTHER INFORMATION: DNA encoding G3736 EDLL domain

<400> SEQUENCE: 86
gtgatcgagt tcgagtacct ggacgacgac gtgctgcagt ccatgctc        48

<210> SEQ ID NO 87
<211> LENGTH: 48
<212> TYPE: DNA
<213> ORGANISM: Oryza sativa
<220> FEATURE:
<223> OTHER INFORMATION: DNA encoding G3381 EDLL domain

<400> SEQUENCE: 87
ccgatcgagt tcgagtacct cgatgaccac gtcctgcagg agatgctc        48

<210> SEQ ID NO 88
<211> LENGTH: 48
<212> TYPE: DNA
<213> ORGANISM: Oryza sativa
<220> FEATURE:
<223> OTHER INFORMATION: DNA encoding G3737 EDLL domain

<400> SEQUENCE: 88
aaggtggagc ttgtgtacct tgacgacaag gtgctcgacg agctcctt        48

<210> SEQ ID NO 89
<211> LENGTH: 48
<212> TYPE: DNA
<213> ORGANISM: Oryza sativa
<220> FEATURE:
<223> OTHER INFORMATION: DNA encoding G3515 EDLL domain

<400> SEQUENCE: 89
aaggtggagc tggagtgcct cgacgacaag gtcctggagg acctcctc        48

<210> SEQ ID NO 90
<211> LENGTH: 48
<212> TYPE: DNA
<213> ORGANISM: Zea mays
<220> FEATURE:
<223> OTHER INFORMATION: DNA encoding G3516 EDLL domain

<400> SEQUENCE: 90
aaggtggagc tggagtgcct cgacgacagg gtcttggaag agctgctc        48

<210> SEQ ID NO 91
<211> LENGTH: 48
<212> TYPE: DNA
<213> ORGANISM: Oryza sativa
<220> FEATURE:
<223> OTHER INFORMATION: DNA encoding G3380 EDLL domain

<400> SEQUENCE: 91
gtgatcgagc tggagtgcct agacgaccaa gtgctgcaag agatgctc        48

<210> SEQ ID NO 92
<211> LENGTH: 48
<212> TYPE: DNA
<213> ORGANISM: Zea mays
<220> FEATURE:
<223> OTHER INFORMATION: DNA encoding G3794 EDLL domain -continued

<400> SEQUENCE: 92
gtgatcgagc tggagtgcct ggacgatcag gtgctgcagg agatgctc                48

<210> SEQ ID NO 93
<211> LENGTH: 42
<212> TYPE: DNA
<213> ORGANISM: Medicago truncatula
<220> FEATURE:
<223> OTHER INFORMATION: DNA encoding G3735 EDLL domain

<400> SEQUENCE: 93
gagcttgaat tcttggataa taagttgctt caagaacttc tt                      42

<210> SEQ ID NO 94
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Phe or Leu
<220> FEATURE:
<221> NAME/KEY: misc_feature
<222> LOCATION: (3)..(4)
<223> OTHER INFORMATION: Xaa can be any naturally occurring amino acid
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
<223> OTHER INFORMATION: Xaa can be Asp or Asn
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be Val or Leu
<220> FEATURE:
<221> NAME/KEY: misc_feature
<222> LOCATION: (11)..(12)
<223> OTHER INFORMATION: Xaa can be any naturally occurring amino acid
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain consensus sequence E-F/L-X-X-L/F-D-
      D/N-X-V/L/I-L-X-X-L/M-L

<400> SEQUENCE: 94

Glu Xaa Xaa Xaa Xaa Asp Xaa Xaa Xaa Leu Xaa Xaa Xaa Leu
1               5                   10

<210> SEQ ID NO 95
<211> LENGTH: 14
<212> TYPE: PRT
<213> ORGANISM: Arabidopsis thaliana
<220> FEATURE:
<221> NAME/KEY: misc_feature
<222> LOCATION: (2)..(2)
<223> OTHER INFORMATION: Xaa can be Phe or Leu
<220> FEATURE:
<221> NAME/KEY: misc_feature
<222> LOCATION: (3)..(3)
<223> OTHER INFORMATION: Xaa can be Glu or Val
<220> FEATURE:
<221> NAME/KEY: misc_feature
<222> LOCATION: (4)..(4)
<223> OTHER INFORMATION: Xaa can be Tyr, Cys, or Phe
<220> FEATURE:
<221> NAME/KEY: misc_feature
<222> LOCATION: (5)..(5)
<223> OTHER INFORMATION: Xaa can be Leu or Phe
<220> FEATURE:
<221> NAME/KEY: misc_feature
<222> LOCATION: (7)..(7)
<223> OTHER INFORMATION: Xaa can be Asp or Asn
<220> FEATURE:
<221> NAME/KEY: misc_feature
<222> LOCATION: (8)..(8)
<223> OTHER INFORMATION: Xaa can be any naturally occurring amino acid
<220> FEATURE:
<221> NAME/KEY: misc_feature
<222> LOCATION: (9)..(9)
<223> OTHER INFORMATION: Xaa can be Val or Leu
<220> FEATURE:
<221> NAME/KEY: misc_feature
<222> LOCATION: (11)..(11)
<223> OTHER INFORMATION: Xaa can be Glu, Gln, or Asp
<220> FEATURE:
<221> NAME/KEY: misc_feature
<222> LOCATION: (12)..(12)
<223> OTHER INFORMATION: Xaa can be Glu, Asp, or Ser
<220> FEATURE:
<221> NAME/KEY: misc_feature
<222> LOCATION: (13)..(13)
<223> OTHER INFORMATION: Xaa can be Leu or Met
<220> FEATURE:
<223> OTHER INFORMATION: EDLL domain consensus sequence E-F/L-E/V-Y/C/F-
    L/F-D-D/N-X-V/L-L-E/Q/D-E/D/S-L/M-L

<400> SEQUENCE: 95

Glu Xaa Xaa Xaa Xaa Asp Xaa Xaa Xaa Leu Xaa Xaa Xaa Leu
1               5                   10

<210> SEQ ID NO 96
<211> LENGTH: 682
<212> TYPE: DNA
<213> ORGANISM: artificial sequence
<220> FEATURE:
<223> OTHER INFORMATION: G481:EDLL:cMyc

<400> SEQUENCE: 96
atggcggata cgccttcgag cccagctgga gatggcggag aaagcggcgg ttccgttagg      60
gagcaggatc gataccttcc tatagctaat atcagcagga tcatgaagaa agcgttgcct    120
cctaatggta agattggaaa agatgctaag gatacagttc aggaatgcgt ctctgagttc    180
atcagcttca tcactagcga ggccagtgat aagtgtcaaa aagagaaaag gaaaactgtg    240
aatggtgatg atttgttgtg ggcaatggca acattaggat ttgaggatta cctggaacct    300
ctaaagatat acctagcgag gtacaggag ttggagggtg ataataaggg atcaggaaag    360
agtggagatg gatcaaatag agatgctggt ggcggtgttt ctggtgaaga atgccgagc     420 tggcatatgg aagttttcga gtttgagtat ttggacgata aggttcttga gaacttctt     480 gattcagaag aaaggaagag agagctcggg ttaattaacg gtgaacaaaa gctaatctcc    540
gaggaagact tgaacggtga acaaaaatta atctcgaag aagacttgaa cggactcgac    600
ggtgaacaaa agttgatttc tgaagaagat ttgaacggtg aacaaaagct aatctccgag    660
gaagacttga acggtagctg aa                                              682

<210> SEQ ID NO 97
<211> LENGTH: 1110
<212> TYPE: DNA
<213> ORGANISM: artificial sequence
<220> FEATURE:
<223> OTHER INFORMATION: G400:EDLL:cMyc

<400> SEQUENCE: 97

```
atgatgttcg agaaagacga tctgggtcta agcttaggct tgaattttcc aaagaaacag      60
atcaatctca aatcaaatcc atctgtttct gttactcctt cttcttcttc ttttggatta    120
ttcagaagat cttcatggaa cgagagtttt acttcttcag ttccaaactc agattcgtca    180
caaaaagaaa caagaacttt catccgagga atcgacgtga acagaccacc gtctacagcg    240
gaatacggcg acgaagacgc tggagtatct tcacctaaca gtacagtctc aagctctaca    300
gggaaaagaa gcgagagaga agaagacaca gatccacaag gctcaagagg aatcagtgac    360
gatgaagatg gtgataactc caggaaaaag cttagacttt ccaaagatca atctgctatt    420
cttgaagaga ccttcaaaga tcacagtact ctcaatccga agcagaagca agcattggct    480
aaacaattag ggttacgagc aagacaagtg gaagtttggt ttcagaacag acgagcaaga    540
acaaagctga agcaaacgga ggtagactgc gagttcttac ggagatgctg cgagaatcta    600
acggaagaga accgtcggct acaaaaagaa gtaacggaat tgagagcact taagctctct    660
cctcagttct acatgcacat gagcccaccc actactttga ccatgtgccc ttcatgtgaa    720
cacgtgtcgg tcccgccacc acaacctcag gctgctacgt cagcgcacca ccggtcgttg    780
ccggtcaatg cgtgggctcc tgcgacgagg atatctcacg gcttgacttt tgacgctctt    840
cgtcctaggt cccatatgga agttttcgag tttgagtatt tggacgataa ggttcttgaa    900
gaacttcttg attcagaaga aggaagagaa gagctcgggt taattaacgg tgaacaaaag    960
ctaatctccg aggaagactt gaacggtgaa caaaaattaa tctcagaaga agacttgaac   1020
ggactcgacg tgaacaaaa gttgatttct gaagaagatt tgaacggtga acaaaagcta   1080
atctccgagg aagacttgaa cggtagctga                                    1110
```

<210> SEQ ID NO 98
<211> LENGTH: 1110
<212> TYPE: DNA
<213> ORGANISM: artificial sequence
<220> FEATURE:
<223> OTHER INFORMATION: G400EAR:EDLL:cMyc

<400> SEQUENCE: 98

```
atgatgttcg agaaagacga tctgggtgct agcgctggct tgaattttcc aaagaaacag      60
atcaatctca aatcaaatcc atctgtttct gttactcctt cttcttcttc ttttggatta    120
ttcagaagat cttcatggaa cgagagtttt acttcttcag ttccaaactc agattcgtca    180
caaaaagaaa caagaacttt catccgagga atcgacgtga acagaccacc gtctacagcg    240
gaatacggcg acgaagacgc tggagtatct tcacctaaca gtacagtctc aagctctaca    300
gggaaaagaa gcgagagaga agaagacaca gatccacaag gctcaagagg aatcagtgac    360
gatgaagatg gtgataactc caggaaaaag cttagacttt ccaaagatca atctgctatt    420
cttgaagaga ccttcaaaga tcacagtact ctcaatccga agcagaagca agcattggct    480
aaacaattag ggttacgagc aagacaagtg gaagtttggt ttcagaacag acgagcaaga    540
acaaagctga agcaaacgga ggtagactgc gagttcttac ggagatgctg cgagaatcta    600
acggaagaga accgtcggct acaaaaagaa gtaacggaat tgagagcact taagctctct    660
cctcagttct acatgcacat gagcccaccc actactttga ccatgtgccc ttcatgtgaa    720
cacgtgtcgg tcccgccacc acaacctcag gctgctacgt cagcgcacca ccggtcgttg    780
ccggtcaatg cgtgggctcc tgcgacgagg atatctcacg gcttgacttt tgacgctctt    840
cgtcctaggt cccatatgga agttttcgag tttgagtatt tggacgataa ggttcttgaa    900
```

```
gaacttcttg attcagaaga aggaagagag gagctcgggt taattaacgg tgaacaaaag    960
ctaatctccg aggaagactt gaacggtgaa caaaaattaa tctcagaaga agacttgaac   1020
ggactcgacg gtgaacaaaa gttgatttct gaagaagatt tgaacggtga acaaaagcta   1080
atctccgagg aagacttgaa cggtagctga                                    1110

<210> SEQ ID NO 99
<211> LENGTH: 1821
<212> TYPE: DNA
<213> ORGANISM: Arabidopsis thaliana
<220> FEATURE:
<223> OTHER INFORMATION: Pr:G398

<400> SEQUENCE: 99
cgagtacagt tagatcatta atgagaagga gttatttcat ttgaaatcat gcgtataatg     60
attacaacga agcgaaaatg atgaaggcgc gtggtaggca atgataagat gtcggcgcgt    120
gaggaaacaa aataaaacgc acggccgggt cgagtgtttt cgggtccctt gttgtcacgt    180
gacatgaccc acctgcccat gttctctctt gagcccaaaa ctatttgaga cattttttaa    240
tcatctttcg gcagttttaa tttacttctt cttttttttt tttgtcaaca ataaagcaaa    300
atgattctga ttagcagcac tcagaatata tctgattata gaacacgatc tgaatactta    360
aaaattctac aaaattgatg ataagggaag tatgatgatc tataatagtt gaaagtttaa    420
gaacatgaaa tgaaaataga gaaacagtca gtgaatattg gattcatatg taatacatat    480
gggtgttagt gtaatgatag atcccacatc ccacatggat atgattggat cacaacaggt    540
gactggccca caactttgaa tgagctcaga ttcatgtgga ttgtgttttg taccaaccac    600
ttgatttagt ccttttttttt tcttcattat ttcaacaatt aattgccaac tatttcttcg    660
atatctgttc tcatccgtgt gtgatcttga ctgattgagt tgttttttttt ttctttacaa    720 aggtcacaag ttcttgcacc aatgattgga aaaatttgag ggttaaataa aaatgaaaag    780
agaaaatgaa ctgaaatatt tactaccact tttaggtgga gtaaaaaact aaagatgttc    840
acgtttattt ctttacagta gagtaaatat tttgtagcat aactattaga ttggcaatta    900
ttcaacttac cgtaaatact aaataaaatt cactctagta agctcatcca ataacatctt    960
tatttttttt ttttgacatg gtcaaaaaga ttagcaagtt acaactctta ataataattc   1020
tattaatttt tttttttaata aagaactaat gtctatatat ctcgaaatga tatcaaattg   1080
gcgcaataat aaaattcctc ggatactatt aaatcagaag ctaaggctgc ttatatctaa   1140
tatatgcaag acataacatg agtcacttca tatatatgtg aaggtatata attaaaactt   1200
agaatcatta tttagttgat taggcatata atttgatgta cttattgtcg ctaaataaat   1260
gtcataatgg atttgcaccg catattatag agtttctctt ttcctagtcc aaatttgcaa   1320
gaaataaagt agagatggaa aatatgaatt tgcattttaa atttactttg gattccatac   1380
atatatagaa gtactttgag gttatggaaa agatagcaa agataggac ttactataca    1440 atttactaaa atagtaaaag aagaagaagg aaaagataaa gaaaaaaaaa aaagagaaag   1500
gagaagacaa agagggaaca agttggggat ataataattg agtttcaaaa gggcattaat   1560
agattataat tggccaacct gacaacatct catatcattc acttcctata ttaatcctct   1620
ctttctcttt tcatttccca tttcacatct ctctctctct ataagaaccc tagaagaagg   1680
tttctcttgt cctccataca cttagcacaa ctgataaatc ttttgaggta aaatcagctt   1740
tagatcaagg ttttttctagt catctctact cataaagatc aaagcttttg ctattctcat   1800
```

```
tttctaccaa gagacaatat c                                          1821

<210> SEQ ID NO 100
<211> LENGTH: 894
<212> TYPE: DNA
<213> ORGANISM: artificial sequence
<220> FEATURE:
<223> OTHER INFORMATION: P38588   35S::G28:EDLL

<400> SEQUENCE: 100
gttatgtcga tgacggcgga ttctcaatct gattatgctt ttcttgagtc catacgacga    60
cacttactag gagaatcgga gccgatactc agtgagtcga cagcgagttc ggttactcaa   120
tcttgtgtaa ccggtcagag cattaaaccg gtgtacggac gaaaccctag ctttagcaaa   180
ctgtatcctt gcttcaccga gagctgggga gatttgccgt tgaaagaaaa cgattctgag   240
gatatgttag tttacggtat cctcaacgac gcctttcacg gcggttggga gccgtcttct   300
tcgtcttccg acgaagatcg tagctctttc ccgagtgtta agatcgagac tccggagagt   360
ttcgcggcgg tggattctgt tccggtcaag aaggagaaga cgagtcctgt ttcggcggcg   420
gtgacggcgg cgaagggaaa gcattataga ggagtgagac aaaggccgtg ggggaaattt   480
gcggcggaga ttagagatcc ggcgaagaac ggagctaggg tttggttagg aacgtttgag   540
acggcggagg acgcggcgtt ggcttacgac agagctgctt tcaggatgcg tggttcccgc   600
gctttgttga atttccgtt gagagttaat tcaggagaac ccgacccggt tcgaatcaag   660
tccaagagat cttctttttc ttcttctaac gagaacggag ctccgaagaa gaggagaacg   720
gtggccgccg gtggtggaat ggataaggga ttgacggtga agtgcgaggt tgttgaagtg   780
gcacgtggcg atcgtttatt ggttttaggc ggccgctcta gagaagtttt cgagtttgag   840
tatttggacg ataaggttct tgaagaactt cttgattcag aagaaggaa gaga          894

<210> SEQ ID NO 101
<211> LENGTH: 669
<212> TYPE: DNA
<213> ORGANISM: artificial sequence
<220> FEATURE:
<223> OTHER INFORMATION: P38589   35S::G1274:EDLL

<400> SEQUENCE: 101
atgaatatct ctcaaaaccc tagccctaat tttacgtact tctccgatga aaactttatt    60
aatccgttta tggataacaa cgatttctca aatttgatgt tctttgacat agatgaagga   120
ggtaacaatg gattaatcga ggaagagatc tcatctccga caagcatcgt ttcgtcggag   180
acatttaccg gggaaagcgg cggatccggc agcgcaacaa cgttgagtaa aaaggaatca   240
actaatagag gaagtaaaga gagtgatcag acgaaggaga cgggtcatcg agttgcattt   300
agaacgagat cgaagattga tgtgatggat gatggtttta atggaggaa gtatggcaag   360 aaatctgtca aaaacaacat taacaagagg aattactaca aatgctcaag tgaaggttgc   420
tcggtgaaga gagggtaga gagagatggt gacgatgcag cttatgtaat tacaacatat   480
gaaggagtcc ataaccatga gagtctctct aatgtctatt acaatgaaat ggttttatct   540
tatgatcatg ataactggaa ccaacactct cttcttcgat cttgcggccg ctctagagaa   600
gttttcgagt ttgagtattt ggacgataag gttcttgaag aacttcttga ttcagaagaa   660
aggaagaga                                                           669

<210> SEQ ID NO 102
<211> LENGTH: 1047
```

<212> TYPE: DNA
<213> ORGANISM: artificial sequence
<220> FEATURE:
<223> OTHER INFORMATION: P38590 prAt5G43840::G867:EDLL

<400> SEQUENCE: 102

```
ggtaccatgg aatcgagtag cgttgatgag agtactacaa gtacaggttc catctgtgaa     60
accccggcga taactccggc gaaaaagtcg tcggtaggta acttatacag gatgggaagc    120
ggatcaagcg ttgtgttaga ttcagagaac ggcgtagaag ctgaatctag gaagcttccg    180
tcgtcaaaat acaaaggtgt ggtgccacaa ccaaacggaa gatggggagc tcagatttac    240
gagaaacacc agcgcgtgtg gctcgggaca ttcaacgaag aagacgaagc cgctcgtgcc    300
tacgacgtcg cggttcacag gttccgtcgc cgtgacgccg tcacaaattt caaagacgtg    360
aagatggacg aagacgaggt cgatttcttg aattctcatt cgaaatctga gatcgttgat    420
atgttgagga acatactta taacgaagag ttagagcaga gtaaacggcg tcgtaatggt    480
aacgaaaaca tgactaggac gttgttaacg tcggggttga gtaatgatgg tgtttctacg    540
acggggttta gatcggcgga ggcactgttt gagaaagcgg taacgccaag cgacgttggg    600
aagctaaacc gtttggttat accgaaacat cacgcagaga acatttttcc gttaccgtca    660
agtaacgttt ccgtgaaagg agtgttgttg aactttgagg acgttaacgg gaaagtgtgg    720
aggttccgtt actcgtattg gaacagtagt cagagttatg ttttgactaa aggttggagc    780
aggttcgtta aggagaagaa tctacgtgct ggtgacgtgg ttagtttcag tagatctaac    840
ggtcaggatc aacagttgta cattgggtgg aagtcgagat ccgggtcaga tttagatgcg    900
ggtcgggttt tgagattgtt cggagttaac atttcaccgg agagttcaag aaacgacgtc    960
gtaggaaaca aaagagtgaa cgatactgag atgttatcgt tggtgtgtag caagaagcaa   1020
cgcatctttc acgcctcgtg cggccgc                                       1047
```

<210> SEQ ID NO 103
<211> LENGTH: 798
<212> TYPE: DNA
<213> ORGANISM: artificial sequence
<220> FEATURE:
<223> OTHER INFORMATION: P38591 prAt5G43840::G913:EDLL

<400> SEQUENCE: 103

```
atgtcgaata taataattc tccgaccacc gtgaatcaag aaacgacgac gtctcgtgaa     60
gtctcaatca cattgcctac tgatcaatct cctcaaacct caccaggatc atcttcttct    120
ccttcaccga gaccttccgg tggatcaccg gcgagaagaa cggcgactgg attatccggc    180
aagcactcta tttttcagggg gattcgacta cgtaacggaa aatgggtatc ggagattaga    240
gagccacgta aaacgacaag aatttggctc gggacttatc cggtaccgga gatggctgcc    300
gccgcttacg acgtggctgc gttagcttta aaaggacccg acgccgtttt gaattttcct    360
ggtttagctt tgacttacgt ggctccggtt tcaaactctg ctgcggatat aagagcggct    420
gctagtagag cagcggagat gaagcaaccg gatcagggtg gggatgagaa ggtattggaa    480
ccggttcaac ccggcaaaga ggaagaatta gaagaagtgt cgtgtaactc gtgttcgttg    540
gagtttatgg atgaggaagc gatgttgaat atgccgactt tgttgacgga gatggctgaa    600
gggatgttga tgagtccacc gagaatgatg atacatccga cgatggaaga tgattcgccg    660
gagaatcatg aaggagataa tctttggagt tataaaggcg gccgctctag agaagttttc    720
gagtttgagt atttggacga taaggttctt gaagaacttt tgattcagag agaaaggaag    780
```
agaggatcct ctagctag                                                 798

<210> SEQ ID NO 104
<211> LENGTH: 771
<212> TYPE: DNA
<213> ORGANISM: artificial sequence
<220> FEATURE:
<223> OTHER INFORMATION: P38592   prAt5G43840::G1760:EDLL

<400> SEQUENCE: 104
atgggaagag ggaagattgt gatccaaagg atcgatgatt caacgagtag acaagtcact    60
ttctccaaac gaagaaaggg ccttatcaag aaagccaaag agctagctat tctctgtgat   120
gccgaggtcg gtctcatcat cttctctagc accggaaagc tctatgactt tgcaagctcc   180
agcatgaagt cggttattga tagatacaac aagagcaaga tcgagcaaca acaactattg   240
aaccccgcat cagaagtcaa gttttggcag agaagctg ctgttctaag acaagaactg   300
catgctttgc aagaaaatca tcggcaaatg atgggagaac agctaaatgg tttaagtgtt   360
aacgagctaa acagtcttga gaatcaaatt gagataagtt tgcgtggaat tcgtatgaga   420
aaggaacaac tgttgactca agaaatccaa gaactaagcc aaaagaggaa tcttattcat   480
caggaaaacc tcgatttatc taggaaagta caacggattc atcaagaaaa tgtggagctc   540
tacaagaagg cttatatggc aaacacaaac gggtttacac accgtgaagt agctgttgcg   600
gatgatgaat cacacactca gattcggctg caactaagcc agcctgaaca ttccgattat   660
gacactccac caagagcaaa cgaaggcggc cgctctagag aagttttcga gtttgagtat   720
ttggacgata aggttcttga agaacttctt gattcagaag aaaggaagag a            771

<210> SEQ ID NO 105
<211> LENGTH: 872
<212> TYPE: DNA
<213> ORGANISM: artificial sequence
<220> FEATURE:
<223> OTHER INFORMATION: P38593   35S::G2932:EDLL

<400> SEQUENCE: 105
atgtgtgcat tagtacctcc attgttttcca aactttgggt ggccatcaac gggagagtac    60
gacagctact acctcgccgg agatatcctc aacaacggcg ggtttcttga ttttccggta   120
ccggaggaga cttatggagc tgttacagcg gtgactcaac atcagaatag ctttggtgtt   180
tctgtttcgt cggagggaaa tgaaatagac aacaatccgg tggtcgtcaa gaagcttaat   240
cacaatgcta gtgagcgtga ccgtcgcagg aaaattaact ctttgttctc atctctccgt   300
tcatgtcttc ctgcctctgg ccaatcgaag aagctaagca ttcctgcgac ggtttctcga   360
agcttgaagt acataccaga gctgcaagag caagtgaaga agctaataaa aagaaggaa   420
gagctcttgg tgcaaatttc aggtcaaaga aacactgaat gttacgttaa gcagccacca   480
aaggccgtcg cgaattatat ctcgaccgtt tctgcgacta ggcttggtga caacgaagtg   540
atggtccaaa tctcatcgtc caagattcat aacttttcga tatctaatgt tttaagtggg   600
ttagaagaag ataggtttgt tcttgtggac atgtcatctt caaggtctca aggagaaagg   660
cttttctaca ctttgcattt acaagtggag aagattgaaa attacaagct gaattgcgaa   720
gagttaagtc agaggatgtt gtacttgtat gaggaatgtg gaaactcata tataggcggc   780
cgctctagag aagttttcga gtttgagtat ttggacgata aggttcttga agaacttctt   840
gattcagaag aaaggaagag aggatcctct ag                                   872

<210> SEQ ID NO 106
<211> LENGTH: 774
<212> TYPE: DNA
<213> ORGANISM: artificial sequence
<220> FEATURE:
<223> OTHER INFORMATION: P38587 prRD29a::G912:EDLL

<400> SEQUENCE: 106

```
atgaatccat tttactctac attcccagac tcgtttctct caatctccga tcatagatct      60
ccggtttcag acagtagtga gtgttcacca aagttagctt caagttgtcc aaagaaacga     120
gctgggagga agaagtttcg tgagacacgt catccgattt acagaggagt tcgtcagagg     180
aattctggta aatgggtttg tgaagttaga gagcctaata agaaatctag gatttggtta     240
ggtacttttc cgacggttga aatggctgct cgtgctcatg atgttgctgc tttagctctt     300
cgtggtcgct ctgcttgtct caatttcgct gattctgctt ggcggcttcg tattcctgag     360
actacttgtc ctaaggagat tcagaaagct gcgtctgaag ctgcaatggc gtttcagaat     420
gagactacga cggagggatc taaaactgcg gcggaggcag aggaggcggc aggggagggg     480
gtgagggagg gggagaggag ggcggaggag cagaatggtg gtgtgtttta tatggatgat     540
gaggcgcttt ggggatgcc caacttttt gagaatatgg cggaggggat gcttttgccg       600
ccgccggaag ttggctggaa tcataacgac tttgacggag tgggtgacgt gtcactctgg     660
agttttgacg agtgcggccg ctctagagaa gttttcgagt tgagtatttt ggacgataag     720
gttcttgaag aacttcttga ttcagaagaa aggaagagag atcctctag ctag            774
```

<210> SEQ ID NO 107
<211> LENGTH: 571
<212> TYPE: DNA
<213> ORGANISM: artificial sequence
<220> FEATURE:
<223> OTHER INFORMATION: P30086 G481:EDLL

<400> SEQUENCE: 107

```
ggcgcgcctc agcagtcgct gtcgttacca tggcggatac gccttcgagc ccagctggag      60
atggcggaga aagcggcggt tccgttaggg agcaggatcg ataccttcct atagctaata    120
tcagcaggat catgaagaaa gcgttgcctc ctaatggtaa gattggaaaa gatgctaagg    180
atacagttca ggaatgcgtc tctgagttca tcagcttcat cactagcgag gccagtgata    240
agtgtcaaaa agagaaaagg aaaactgtga atggtgatga tttgttgtgg gcaatggcaa    300
cattaggatt tgaggattac ctggaacctc taaagatata cctagcgagg tacagggagt    360
tggagggtga taataaggga tcaggaaaga gtggagatgg atcaaataga gatgctggtg    420
gcggtgtttc tggtgaagaa atgccgagct ggggagctgg cgaagttttc gagtttgagt    480
atttggacga taaggttctt gaagaacttc ttgattcaga agaaggaag agatagaacc     540
cagcggtact cgctgaggcg atcgcgggcc c                                   571
```

<210> SEQ ID NO 108
<211> LENGTH: 850
<212> TYPE: DNA
<213> ORGANISM: artificial sequence
<220> FEATURE:
<223> OTHER INFORMATION: P30087 G715:EDLL

<400> SEQUENCE: 108

```
ggcgcgcctc agcagtcgct gtcgttacca tggataccaa caaccagcaa ccacctccct      60
ccgccgccgg aatccctcct ccaccacctg gaaccaccat ctccgccgca ggaggaggag    120
```

```
cttcttacca ccaccttctc caacaacaac aacaacagct ccaactattc tggacctacc    180
aacgccaaga gatcgaacaa gttaacgatt tcaaaaacca tcagcttcca ctagctagga    240
taaaaaagat catgaaagcc gatgaagatg ttcgtatgat ctccgcagaa gcaccgattc    300
tcttcgcgaa agcttgtgag cttttcattc tcgagctcac gatcagatct tggcttcacg    360
ctgaggagaa taaacgtcgt acgcttcaga aaaacgatat cgctgctgcg attactagga    420
ctgatatctt cgatttcctt gttgatattg ttcctagaga tgagattaag gacgaagccg    480
cagtcctcgg tggtggaatg gtggtggctc ctaccgcgag cggcgtgcct tactattatc    540
cgccgatggg acaaccagct ggtcctggag ggatgatgat tgggagacca gctatggatc    600
cgaatggtgt ttatgtccag cctccgtctc aggcgtggca gagtgtttgg cagacttcga    660
cggggacggg agatgatgtc tcttatggta gtggtggaag ttccggtcaa gggaatctcg    720
acggccaagg tggagctggc gaagttttcg agtttgagta tttggacgat aaggttcttg    780
aagaacttct tgattcagaa gaaaggaaga gatagaaccc agcggtactc gctgaggcga    840
tcgcgggccc                                                          850
```

<210> SEQ ID NO 109
<211> LENGTH: 718
<212> TYPE: DNA
<213> ORGANISM: artificial sequence
<220> FEATURE:
<223> OTHER INFORMATION: P30089 G482:EDLL

<400> SEQUENCE: 109

```
ggcgcgcctc agcagtcgct gtcgttacca tggggattc cgacagggat tccggtggag    60
ggcaaaacgg gaacaaccag aacggacagt cctccttgtc tccaagagag caagacaggt   120
tcttgccgat cgctaacgtc agccggatca tgaagaaggc cttgcccgcc aacgccaaga   180
tctctaaaga tgccaaagag acgatgcagg agtgtgtctc cgagttcatc agcttcgtca   240
ccggagaagc atctgataag tgtcagaagg agaagaggaa gacgatcaac ggagacgatt   300
tgctctgggc tatgactact ctaggtttg aggattatgt tgagccattg aaagtttact   360
tgcagaggtt tagggagatc gaaggggaga ggactggact agggaggcca cagactggtg   420
gtgaggtcgg agagcatcag agagatgctg tcggagatgg cggtgggttc tacggtggtg   480
gtggtgggat gcagtatcac caacatcatc agtttcttca ccagcagaac catatgtatg   540
gagccacagg tggcggtagc gacagtggag gtggagctgc ctccggtagg acaaggactg   600
gagctggcga agttttcgag tttgagtatt tggacgataa ggttcttgaa gaacttcttg   660
attcagaaga aaggaagaga tagaacccag cggtactcgc tgaggcgatc gcgggccc    718
```

<210> SEQ ID NO 110
<211> LENGTH: 964
<212> TYPE: DNA
<213> ORGANISM: artificial sequence
<220> FEATURE:
<223> OTHER INFORMATION: P30091 G926:EDLL

<400> SEQUENCE: 110

```
ggcgcgcctc agcagtcgct gtcgttacca tgcaatcaaa accgggaaga gaaaacgaag    60
aggaagtcaa taatcaccat gctgttcagc agccgatgat gtatgcagag ccctggtgga   120 aaacaactc ctttggtgtt gtacctcaag cgagaccttc tggaattcca tcaaattcct   180
cttctttgga ttgccccaat ggttccgagt caaacgatgt tcattcagca tctgaagacg   240
gtgcgttgaa tggtgaaaac gatggcactt ggaaggattc acaagctgca acttcctctc   300
```

```
gttcagtaga taatcacgga atggaaggaa atgacccagc gctctctatc cgtaacatgc    360
atgatcagcc acttgtacaa ccaccagagc ttgttggaca ctatatcgct tgtgtcccaa    420
acccatatca ggatccatat tatgggggat tgatgggagc atatggtcat cagcaattgg    480
gttttcgtcc atatcttgga atgcctcgtg aaagaacagc tctgccactt gacatggcac    540
aagagcccgt ttatgtgaat gcaaagcagt acgagggaat tctaaggcga agaaaagcac    600
gtgccaaggc agagctagag aggaaagtca tccgggacag aaagccatat cttcacgagt    660
caagacacaa gcatgcaatg agaagggcac gagcgagtgg aggccggttt gcgaagaaaa    720
gtgaggtaga agcgggagag gatgcaggag ggagagacag agaaaggggt tcagcaacca    780
actcatcagg ctctgaacaa gttgagacag actctaatga accctgaat tcttctggtg     840 caccaggagc tggcgaagtt ttcgagtttg agtatttgga cgataaggtt cttgaagaac    900
ttcttgattc agaagaaagg aagagataga acccagcggt actcgctgag gcgatcgcgg    960
gccc                                                                 964

<210> SEQ ID NO 111
<211> LENGTH: 509
<212> TYPE: DNA
<213> ORGANISM: Arabidopsis thaliana
<220> FEATURE:
<223> OTHER INFORMATION: P39387  prRD29a  abiotic stress inducible
      promoter

<400> SEQUENCE: 111
accggtattt tacgtataaa ataaaagatc atacctatta gaacgattaa ggagaaatac     60
aattcgaatg agaaggatgt gccgtttgtt ataataaaca gccacacgac gtaaacgtaa    120
aatgaccaca tgatgggcca atagacatgg accgactact aataatagta agttacattt    180
taggatggaa taaatatcat accgacatca gtttgaaaga aagggaaaa aagaaaaaa     240 taaataaaag atatactacc gacatgagtt ccaaaaagca aaaaaaaaga tcaagccgac    300
acagacacgc gtagagagca aaatgacttt gacgtcacac cacgaaaaca gacgcttcat    360
acgtgtccct ttatctctct cagtctctct ataaacttag tgagaccctc ctctgtttta    420
ctcacaaata agcaaactag aaaacaatca tcaggaataa agggtttgat tacttctatt    480
ggaaagaaaa aaatctttgg aaacctagg                                     509

<210> SEQ ID NO 112
<211> LENGTH: 795
<212> TYPE: DNA
<213> ORGANISM: Arabidopsis thaliana
<220> FEATURE:
<223> OTHER INFORMATION: P29152  prAT5G43840 drought inducible promoter

<400> SEQUENCE: 112
ggatccctcg atttcgaat aaattatttg agctttccaa actgtaattc aagtattatt      60
acttatatag tgttagtgta cttcaaaagt taaagcataa attttcttat atttgaaatg    120
acctcttctt tacaaaatct tcttaaaatt atgcattatc aatatattaa ttgtatatat    180
atatataatg tataattctg cttgtgtcgt gcttaaccgt ttgatttggt gtggttagat    240
ctggttttcc cccaacccaa ttcaattgaa tcaaggatca atcaaatttt caaaggatac    300
tcttgttctc tacacaaatc tttcaaaggg ttccaccaaa aatcccatca ttctgacttc    360
agaataaaca aacaaaccac gaaacgtatc tctatgcatt cactcaacg tgtcatgggc     420 gaaaacgaag cttataaatg ttggagcata gtcactaaat ttataatgat taattaaatt    480
```

```
ttagattttc tgatattcat agaagacaaa agaacacaaa agtagcatct tccaatgaat      540
gtatgacact atgatctctc atttccattt atagcaaatc ggctttgtcc acatcaaaga      600
taactaataa atagacttat ccaaaacact caaaagcaat acatttctat ccaaaaatat      660
taaaccccaa aatatagac agcataaaag catcctcaag cttcagctat tcatcacaac       720
tattctctcc tctctctttt tttattaaaa aagctcaaat ttatataggt ttttgttca       780 caaaccgggc gcgcc                                                        795
```

<210> SEQ ID NO 113
<211> LENGTH: 619
<212> TYPE: DNA
<213> ORGANISM: Arabidopsis thaliana
<220> FEATURE:
<223> OTHER INFORMATION: P28627  prAT5G52300 drought inducible promoter

<400> SEQUENCE: 113

```
ggatcctgat gatgatgatg aagaagagaa cgaattttga aattggcggt tttgaatttt      60
taagaaatta aaaatatcc cccgtcgatt tcaagaggga gatggagata ccaaagcaac       120
tctcgccact tgtcgtcttt taattttaat tgagtacgtt atgccgtttt aaatgttcaa      180
aacagcacac agttgatagc tgaattgatt ttttcttttg ccgttttgtt atatttaaac     240
aacacacagt gcatttgcca ataactaca tgatgggcca ataaacgtgg accgactaaa      300
actaaataat agaagataca tcgataggct tctctaaaga tcggataaaa gataatgtcg     360
catagccacg tagagagcaa ctggctgaga cgtggcagga cgaaacggac gcatcgtacg     420
tgtcagaatc ctacagaagt aaagagacag aagccagaga gaggtggttc ggccatatct     480
catcgttctc tctataaact ttatcgaact ttgttctgat tttctcagag acacgaaaag     540
aaagaaaaca acactagaac aaagagggtt tgattgattc acttgaaaaa gagaaaacac     600
agctttggaa aggcgcgcc                                                   619
```

<210> SEQ ID NO 114
<211> LENGTH: 1218
<212> TYPE: DNA
<213> ORGANISM: Arabidopsis thaliana
<220> FEATURE:
<223> OTHER INFORMATION: P28632  prAT1G35230 pathogen inducible promoter

<400> SEQUENCE: 114

```
ggatccctct tctaagaata gttgcaagcc tttaaatact ccgacaaatc tggcattagc      60
cgaaagatat tccaaactca aaatcggatc agatagtgtg gtggtctaat tttacctgga     120
tcgggagatg tccactctgt accaccttga tgcattttta ctgatactga tcagatcaac     180
cgatataata tatatataaa aaagaaagt tcgtccaaaa ggaatcatta ttttcttaac      240
caatagaata taggaaataa taggataaat ctatattagt ggacaggtaa tagaatgctt     300
tcattcacat tgaaatcata ttgtaataag cacacttttc ttatcaaaaa aaaaaggcaa     360
aaagaaatgg ccacgcaata aaatcattag ggtaagttga attttggtcc ataatattat     420
aaattaattt aatctcgaaa gcttaatctt atgatctcat gtgatcttta ttgaatttac     480
ttacttccat agagttttgt attttgtcta aggaaagaaa aaaaaagtct gccagctttg     540
gaacgccgcc cattcctcta gactttcttg gaaacaacgc gttgttcttg ttggggtcga     600
cgaagactca ctaaatccat ccgacgactc agatttatc ttggcttctt ttgatgtgta      660
cacatatcca ccctgatttg attcccaaag ccaaaagcct gaacaatgta gtgtagaaga    720
```

```
agtgacggga aaaaacggta atgaatccac aatggatatt tacagaaaga aataaaatta    780
tatagattat agagaagcaa aattatgcaa ataatcttta tttaatacta ttaaaagagt    840
agctgttgga aactataaca ggtaattttaa aatattttac aagttcaaca tataataatt   900
ttgaaattca gtccaacata actatcagta tggaaataag ccaaacaaat tactcaaaat    960
aagaaatatg ttttcacatt attatttaaa cattttttagt catttgtttg cttatttcc    1020 aaaacgatat ttatgttgga cttgttttca aagtattat gttgaacttg taaaaaaat     1080 ttatatagct gttgaaattt ccaagaaaat aaggttttac acctaaaccc ttccactata    1140
tatataaacc ccacttttgt ctctatatct ttactaattt cttaaaccct ctcaacaata    1200
cgtaacaccg ggcgcgcc                                                  1218

<210> SEQ ID NO 115
<211> LENGTH: 574
<212> TYPE: DNA
<213> ORGANISM: Cauliflower mosaic virus
<220> FEATURE:
<223> OTHER INFORMATION: CaMV 35S promoter

<400> SEQUENCE: 115
gcggattcca ttgcccagct atctgtcact ttattgtgaa gatagtgaaa aagaaggtgg    60
ctcctacaaa tgccatcatt gcgataaagg aaaggccatc gttgaagatg cctctgccga   120
cagtggtccc aaagatggac ccccacccac gaggagcatc gtggaaaaag aagacgttcc   180
aaccacgtct tcaaagcaag tggattgatg tgatggtccg attgagactt ttcaacaaag   240
ggtaatatcc ggaaacctcc tcggattcca ttgcccagct atctgtcact ttattgtgaa   300
gatagtggaa aaggaaggtg gctcctacaa atgccatcat tgcgataaag gaaaggccat   360
cgttgaagat gcctctgccg acagtggtcc caaagatgga ccccaccca cgaggagcat   420 cgtggaaaaa gaagacgttc caaccacgtc ttcaaagcaa gtggattgat gtgatatctc   480
cactgacgta aggggatgacg cacaatccca ctatccttcg caagacccett cctctatata   540 aggaagttca tttcatttgg agaggacacg ctga                                574

<210> SEQ ID NO 116
<211> LENGTH: 284
<212> TYPE: PRT
<213> ORGANISM: Arabidopsis thaliana
<220> FEATURE:
<223> OTHER INFORMATION: G400 polypeptide

<400> SEQUENCE: 116

Met Met Phe Glu Lys Asp Asp Leu Gly Leu Ser Leu Gly Leu Asn Phe
1               5                   10                  15

Pro Lys Lys Gln Ile Asn Leu Lys Ser Asn Pro Ser Val Ser Val Thr
            20                  25                  30

Pro Ser Ser Ser Ser Phe Gly Leu Phe Arg Arg Ser Ser Trp Asn Glu
        35                  40                  45

Ser Phe Thr Ser Ser Val Pro Asn Ser Asp Ser Gln Lys Glu Thr
    50                  55                  60

Arg Thr Phe Ile Arg Gly Ile Asp Val Asn Arg Pro Pro Ser Thr Ala
65                  70                  75                  80

Glu Tyr Gly Asp Glu Asp Ala Gly Val Ser Ser Pro Asn Ser Thr Val
                85                  90                  95

Ser Ser Ser Thr Gly Lys Arg Ser Glu Arg Glu Glu Asp Thr Asp Pro
            100                 105                 110
```

```
Gln Gly Ser Arg Gly Ile Ser Asp Asp Glu Asp Gly Asp Asn Ser Arg
            115                 120                 125

Lys Lys Leu Arg Leu Ser Lys Asp Gln Ser Ala Ile Leu Glu Glu Thr
    130                 135                 140

Phe Lys Asp His Ser Thr Leu Asn Pro Lys Gln Lys Gln Ala Leu Ala
145                 150                 155                 160

Lys Gln Leu Gly Leu Arg Ala Arg Gln Val Glu Val Trp Phe Gln Asn
                165                 170                 175

Arg Arg Ala Arg Thr Lys Leu Lys Gln Thr Glu Val Asp Cys Glu Phe
            180                 185                 190

Leu Arg Arg Cys Cys Glu Asn Leu Thr Glu Glu Asn Arg Arg Leu Gln
        195                 200                 205

Lys Glu Val Thr Glu Leu Arg Ala Leu Lys Leu Ser Pro Gln Phe Tyr
    210                 215                 220

Met His Met Ser Pro Pro Thr Thr Leu Thr Met Cys Pro Ser Cys Glu
225                 230                 235                 240

His Val Ser Val Pro Pro Gln Pro Gln Ala Ala Thr Ser Ala His
                245                 250                 255

His Arg Ser Leu Pro Val Asn Ala Trp Ala Pro Ala Thr Arg Ile Ser
            260                 265                 270

His Gly Leu Thr Phe Asp Ala Leu Arg Pro Arg Ser
        275                 280

<210> SEQ ID NO 117
<211> LENGTH: 440
<212> TYPE: DNA
<213> ORGANISM: Saccharomyces cerevisiae
<220> FEATURE:
<223> OTHER INFORMATION: GAL4 DNA binding domain (GD)

<400> SEQUENCE: 117
atggagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
caaagacagt tgactgtatc                                                440

<210> SEQ ID NO 118
<211> LENGTH: 702
<212> TYPE: DNA
<213> ORGANISM: artificial sequence
<220> FEATURE:
<223> OTHER INFORMATION: GD-EDLL:cMyc / (GD:G1792EDLL:cMyc)

<400> SEQUENCE: 118
atggagctac tgtcttctat cgaacaagca tgcgatattt gccgacttaa aaagctcaag      60
tgctccaaag aaaaaccgaa gtgcgccaag tgtctgaaga caactggga gtgtcgctac     120 tctcccaaaa ccaaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
```

```
aatgtgaata aagatgccgt cacagataga ttggcttcag tggagactga tatgcctcta      360
acattgagac agcatagaat aagtgcgaca tcatcatcgg aagagagtag taacaaaggt      420
caaagacagt tgactgtatc gccgcatatg gaagttttcg agtttgagta tttggacgat      480
aaggttcttg aagaacttct tgattcagaa gaaaggaaga gagagctcgg gttaattaac      540
ggtgaacaaa agctaatctc cgaggaagac ttgaacggtg aacaaaaatt aatctcagaa      600
gaagacttga acggactcga cggtgaacaa aagttgattt ctgaagaaga tttgaacggt      660
gaacaaaagc taatctccga ggaagacttg aacggtagct ga                        702

<210> SEQ ID NO 119
<211> LENGTH: 72
<212> TYPE: DNA
<213> ORGANISM: artificial sequence
<220> FEATURE:
<223> OTHER INFORMATION: EDLLm, EDLL domain with conserved hydrophobic
      leucine residues changed to valine

<400> SEQUENCE: 119
gaagttttcg agtttgagta tttggacgat aaggttgttg aagaacttgt tgattcagaa       60
gaaaggaaga ga                                                           72

<210> SEQ ID NO 120
<211> LENGTH: 1959
<212> TYPE: DNA
<213> ORGANISM: artificial sequence
<220> FEATURE:
<223> OTHER INFORMATION: Gal4UAS(4X):GUS

<400> SEQUENCE: 120
ctgcagctcg gaggacagta ctccgctcgg aggacagtac tccgctcgga ggacagtact       60
ccgctcggag gacagtactc cgtcgaccgc aagacccttc ctctatataa ggaagttcat      120
ttcatttgga gaggacacgc tcgagtggcc accatggtaa gcttagcggg ccccgtccgt      180
gaaatcaaaa aactcgacgg cctgtgggca ttcagtctgg atcgcgaaaa ctgtggaatt      240
gatcagcgtt ggtgggaaag cgcgttacaa gaaagccggg caattgctgt gccaggcagt      300
tttaacgatc agttcgccga tgcagatatt cgtaattatg cgggcaacgt ctggtatcag      360
cgcgaagtct ttataccgaa aggttgggca ggccagcgta tcgtgctgcg tttcgatgcg      420
gtcactcatt acggcaaagt gtgggtcaat aatcaggaag tgatggagca tcagggcggc      480
tatacgccat ttgaagccga tgtcacgccg tatgttattg ccgggaaaag tgtacgtatc      540
accgtttgtg tgaacaacga actgaactgg cagactatcc cgccgggaat ggtgattacc      600
gacgaaaacg gcaagaaaaa gcagtcttac ttccatgatt tctttaacta tgccggaatc      660
catcgcagcg taatgctcta caccacgccg aacacctggg tggacgatat caccgtggtg      720
acgcatgtcg cgcaagactg taaccacgcg tctgttgact ggcaggtggt ggccaatggt      780
gatgtcagcg ttgaactgcg tgatgcggat caacaggtgt tgcaactgga caaggcact       840 agcgggactt tgcaagtggt gaatccgcac tctctggcaac cgggtgaagg ttatctctat      900
gaactgtgcg tcacagccaa agccagaca gagtgtgata tctacccgct tcgcgtcggc       960
atccggtcag tggcagtgaa gggcgaacag ttcctgatta ccacaaaacc gttctacttt     1020
actggctttg gtcgtcatga agatgcggac ttacgtggca aaggattcga taacgtgctg     1080
atggtgcacg accacgcatt aatggactgg attggggcca actcctaccg tacctcgcat     1140
tacccttacg ctgaagagat gctcgactgg gcagatgaac atggcatcgt ggtgattgat     1200
```

```
gaaactgctg ctgtcggctt taacctctct ttaggcattg gtttcgaagc gggcaacaag     1260
ccgaaagaac tgtacagcga agaggcagtc aacggggaaa ctcagcaagc gcacttacag     1320
gcgattaaag agctgatagc gcgtgacaaa aaccacccaa gcgtggtgat gtggagtatt     1380
gccaacgaac cggatacccg tccgcaagtg cacgggaata tttcgccact ggcggaagca     1440
acgcgtaaac tcgacccgac gcgtccgatc acctgcgtca atgtaatgtt ctgcgacgct     1500
cacaccgata ccatcagcga tctctttgat gtgctgtgcc tgaaccgtta ttacggatgg     1560
tatgtccaaa gcggcgattt ggaaacggca gagaaggtac tggaaaaaga acttctggcc     1620
tggcaggaga aactgcatca gccgattatc atcaccgaat acggcgtgga tacgttagcc     1680
gggctgcact caatgtacac cgacatgtgg agtgaagagt atcagtgtgc atggctggat     1740
atgtatcacc gcgtctttga tcgcgtcagc gccgtcgtcg gtaacaggt atggaatttc     1800 gccgattttg cgacctcgca aggcatattg cgcgttggcg gtaacaagaa agggatcttc     1860
actcgcgacc gcaaaccgaa gtcggcggct tttctgctgc aaaaacgctg gactggcatg     1920
aacttcggtg aaaaaccgca gcagggaggc aaacaatga                           1959

<210> SEQ ID NO 121
<211> LENGTH: 1253
<212> TYPE: DNA
<213> ORGANISM: artificial sequence
<220> FEATURE:
<223> OTHER INFORMATION: GD:G483 fusion

<400> SEQUENCE: 121
atggagctac tgtcttctat cgaacaagca tgcgatattt gccgacttaa aaagctcaag       60
tgctccaaag aaaaaccgaa gtgcgccaag tgtctgaaga caactgggga gtgtcgctac      120
tctcccaaaa ccaaaaggtc tccgctgact agggcacatc tgacagaagt ggaatcaagg      180
ctagaaagac tggaacagct atttctactg attttttcctc gagaagacct tgacatgatt      240
ttgaaaatgg attctttaca ggatataaaa gcattgttaa caggattatt tgtacaagat      300
aatgtgaata agatgccgt cacagataga ttggcttcag tggagactga tatgcctcta      360
acattgagac agcatagaat aagtgcgaca tcatcatcgg aagagagtag taacaaaggt      420
caaagacagt tgactgtatc gccgcatatg gaggcggcgc gccacgcggc cgcactagtc      480
atggagcagt cagaagaggg tcaacagcaa cagcaacagg gagtgatgga ttatgtacct      540
cctcatgctt atcagagtgg gccagtaaat gcagcttccc atatggcatt ccaacaagct      600
caccacttcc accaccacca tcagcagcaa caacagcagc agcttcagat gttctgggct      660
aaccaaatgc aagagatcga gcataccact gatttcaaga accacaccct tccctagcc      720 cgcatcaaga agatcatgaa agctgatgaa gatgtgagga tgatctctgc ggaggctcct      780 gtgattttg ccaaggcctg tgagatgttc attttggagc tcactctacg tgcttggatc      840
cacaccgagg agaacaagag gaggaccttg cagaagaacg catcgccgc tgccatttcc      900 aggaccgacg tgtttgattt ccttgtggac ataatcccga gggacgagct gaaagaagaa      960
ggtttaggcg tgaccaaagg gaccatacca tcggtggtgg gttccccgcc atactattac     1020
ttgcaacaac agggatgat gcaacactgg ccccaggagc aacaccctga tgagtctgcc     1080
ccgggtgagc tcgaaggtga acaaaagcta atctccgagg aagacttgaa cggtgaacaa     1140
aaattaatct cagaagaaga cttgaacgga ctcgacggtg aacaaaagtt gatttctgaa     1200
gaagatttga acggtgaaca aaagctaatc tccgaggaag acttgaacgg tag             1253
```

<210> SEQ ID NO 122
<211> LENGTH: 699
<212> TYPE: DNA
<213> ORGANISM: artificial sequence
<220> FEATURE:
<223> OTHER INFORMATION: GD:VP16 fusion

<400> SEQUENCE: 122

```
atggagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
caaagacagt tgactgtatc gccggaattc ccggggatct gggccccccc gaccgatgtc     480
agcctggggg acgagctcca cttagacggc gaggacgtgg cgatggcgca tgccgacgcg     540
ctagacgatt tcgatctgga catgttgggg acggggatt ccccgggtcc gggatttacc     600
ccccacgact ccgcccccta cggcgctctg gatatggccg acttcgagtt tgagcagatg     660
tttaccgatg cccttggaat tgacgagtac ggtgggtga                           699
```

<210> SEQ ID NO 123
<211> LENGTH: 732
<212> TYPE: DNA
<213> ORGANISM: artificial sequence
<220> FEATURE:
<223> OTHER INFORMATION: GD:G30EDLL:cMyc fusion

<400> SEQUENCE: 123

```
atggagctac tgtcttctat cgaacaagca tgcgatattt gccgacttaa aaagctcaag      60
tgctccaaag aaaaaccgaa gtgcgccaag tgtctgaaga caactggga gtgtcgctac     120
tctcccaaaa ccaaaaggtc tccgctgact agggcacatc tgacagaagt ggaatcaagg     180
ctagaaagac tggaacagct atttctactg attttcctc gagaagacct tgacatgatt     240
ttgaaaatgg attctttaca ggatataaaa gcattgttaa caggattatt tgtacaagat     300
aatgtgaata aagatgccgt cacagataga ttggcttcag tggagactga tatgcctcta     360
acattgagac agcatagaat aagtgcgaca tcatcatcgg aagagagtag taacaaaggt     420
caaagacagt tgactgtatc gccgcatatg gtttttgagt ttgagtactt ggacgatagc     480
gttttggatg aacttcttga atatggagag aactataaca agactcataa tatcaacatg     540
ggcaagaggc aagagctcgg gttaattaac ggtgaacaaa agctaatctc cgaggaagac     600
ttgaacggtg aacaaaaatt aatctcagaa gaagacttga acggactcga cggtgaacaa     660
aagttgattt ctgaagaaga tttgaacggt gaacaaaagc taatctccga ggaagacttg     720
aacggtagct ga                                                         732
```

<210> SEQ ID NO 124
<211> LENGTH: 702
<212> TYPE: DNA
<213> ORGANISM: artificial sequence
<220> FEATURE:
<223> OTHER INFORMATION: GD:G3518EDLL:cMyc fusion

<400> SEQUENCE: 124

```
atggagctac tgtcttctat cgaacaagca tgcgatattt gccgacttaa aaagctcaag    60
tgctccaaag aaaaaccgaa gtgcgccaag tgtctgaaga acaactggga gtgtcgctac   120
tctcccaaaa ccaaaaggtc tccgctgact agggcacatc tgacagaagt ggaatcaagg   180
ctagaaagac tggaacagct atttctactg attttcctc gagaagacct tgacatgatt   240
ttgaaaatgg attctttaca ggatataaaa gcattgttaa caggattatt tgtacaagat   300
aatgtgaata agatgccgt cacagataga ttggcttcag tggagactga tatgcctcta   360
acattgagac agcatagaat aagtgcgaca tcatcatcgg aagagagtag taacaaaggt   420
caaagacagt tgactgtatc gccgcatatg acttttgagt ggagtacttc gataataag    480
ttgctcgagg aactccttca gatgcaagat aacagacact tcgagctcgg gttaattaac   540
ggtgaacaaa agctaatctc cgaggaagac ttgaacggtg aacaaaaatt aatctcagaa   600
gaagacttga acggactcga cggtgaacaa aagttgattt ctgaagaaga tttgaacggt   660
gaacaaaagc taatctccga ggaagacttg aacggtagct ga                      702
```

<210> SEQ ID NO 125
<211> LENGTH: 693
<212> TYPE: DNA
<213> ORGANISM: artificial sequence
<220> FEATURE:
<223> OTHER INFORMATION: GD:G3735EDLL:cMyc fusion

<400> SEQUENCE: 125

```
atggagctac tgtcttctat cgaacaagca tgcgatattt gccgacttaa aaagctcaag    60
tgctccaaag aaaaaccgaa gtgcgccaag tgtctgaaga acaactggga gtgtcgctac   120
tctcccaaaa ccaaaaggtc tccgctgact agggcacatc tgacagaagt ggaatcaagg   180
ctagaaagac tggaacagct atttctactg attttcctc gagaagacct tgacatgatt   240
ttgaaaatgg attctttaca ggatataaaa gcattgttaa caggattatt tgtacaagat   300
aatgtgaata agatgccgt cacagataga ttggcttcag tggagactga tatgcctcta   360
acattgagac agcatagaat aagtgcgaca tcatcatcgg aagagagtag taacaaaggt   420
caaagacagt tgactgtatc gccgcatatg tttgatgagc ttgaattctt ggataataag   480
ttgcttcaag aacttcttca agatggaaca caagagctcg ggttaattaa cggtgaacaa   540
aagctaatct ccgaggaaga cttgaacggt gaacaaaaat taatctcaga agaagacttg   600
aacggactcg acggtgaaca aaagttgatt tctgaagaag atttgaacgg tgaacaaaag   660
ctaatctccg aggaagactt gaacggtagc tga                                693
```

<210> SEQ ID NO 126
<211> LENGTH: 714
<212> TYPE: DNA
<213> ORGANISM: artificial sequence
<220> FEATURE:
<223> OTHER INFORMATION: GD:G3737EDLL:cMyc fusion

<400> SEQUENCE: 126

```
atggagctac tgtcttctat cgaacaagca tgcgatattt gccgacttaa aaagctcaag    60
tgctccaaag aaaaaccgaa gtgcgccaag tgtctgaaga acaactggga gtgtcgctac   120
tctcccaaaa ccaaaaggtc tccgctgact agggcacatc tgacagaagt ggaatcaagg   180
ctagaaagac tggaacagct atttctactg attttcctc gagaagacct tgacatgatt   240
ttgaaaatgg attctttaca ggatataaaa gcattgttaa caggattatt tgtacaagat   300
aatgtgaata agatgccgt cacagataga ttggcttcag tggagactga tatgcctcta   360
```

```
acattgagac agcatagaat aagtgcgaca tcatcatcgg aagagagtag taacaaaggt    420
caaagacagt tgactgtatc gccgcatatg aaggtggagc ttgtgtacct tgacgacaag    480
gtgctcgacg agctccttgc ggaggactac agctaccgca acaacaacaa ctacgagctc    540
gggttaatta acggtgaaca aaagctaatc tccgaggaag acttgaacgg tgaacaaaaa    600
ttaatctcag aagaagactt gaacggactc gacggtgaac aaaagttgat ttctgaagaa    660
gatttgaacg gtgaacaaaa agctaatctc ccgaggaagact tgaacggtag ctga        714

<210> SEQ ID NO 127
<211> LENGTH: 717
<212> TYPE: DNA
<213> ORGANISM: artificial sequence
<220> FEATURE:
<223> OTHER INFORMATION: GD:G3739EDLL:cMyc fusion

<400> SEQUENCE: 127
atggagctac tgtcttctat cgaacaagca tgcgatattt gccgacttaa aaagctcaag     60
tgctccaaag aaaaaccgaa gtgcgccaag tgtctgaaga caactgggga gtgtcgctac    120
tctcccaaaa ccaaaaggtc tccgctgact agggcacatc tgacagaagt ggaatcaagg    180
ctagaaagac tggaacagct atttctactg attttcctc gagaagacct tgacatgatt    240
ttgaaaatgg attctttaca ggatataaaa gcattgttaa caggattatt tgtacaagat    300
aatgtgaata agatgccgt cacagataga ttggcttcag tggagactga tatgcctcta    360
acattgagac agcatagaat aagtgcgaca tcatcatcgg aagagagtag taacaaaggt    420
caaagacagt tgactgtatc gccgcatatg gtgatcgagc tcgagtacct cgacgacgag    480
gtgctgcagg agatgctcag gaaccacgag ccgtcgtcgt ctgcgaggaa gaagatggag    540
ctcgggttaa ttaacggtga acaaaagcta atctccgagg aagacttgaa cggtgaacaa    600
aaattaatct cagaagaaga cttgaacgga ctcgacggtg aacaaaagtt gatttctgaa    660
gaagatttga acggtgaaca aaagctaatc tccgaggaag acttgaacgg tagctga       717

<210> SEQ ID NO 128
<211> LENGTH: 1032
<212> TYPE: DNA
<213> ORGANISM: artificial sequence
<220> FEATURE:
<223> OTHER INFORMATION: cMyc:G400 fusion

<400> SEQUENCE: 128
atggcgttaa ttaacggtga acaaaagcta atctccgagg aagacttgaa cggtgaacaa     60
aaattaatct cagaagaaga cttgaacgga ctcgacggtg aacaaaagtt gatttctgaa    120
gaagatttga acggtgaaca aaagctaatc tccgaggaag acttgaacgg tagccatatg    180
atgttcgaga agacgatct gggtctaagc ttaggcttga attttccaaa gaaacagatc    240
aatctcaaat caaatccatc tgtttctgtt actccttctt cttcttcttt tggattattc    300
agaagatctt catggaacga gagttttact tcttcagttc caaactcaga ttcgtcacaa    360
aaagaaacaa gaactttcat ccgaggaatc gacgtgaaca gaccaccgtc tacagcggaa    420
tacggcgacg aagacgctgg agtatcttca cctaacagta cagtctcaag ctctacaggg    480
aaaagaagcg agagagaaga agacacagat ccacaaggct caagaggaat cagtgacgat    540
gaagatggtg ataactccag gaaaaagctt agacttcca aagatcaatc tgctattctt    600
gaagagacct tcaaagatca cagtactctc aatccgaagc agaagcaagc attggctaaa    660
```

```
caattagggt tacgagcaag acaagtggaa gtttggtttc agaacagacg agcaagaaca    720
aagctgaagc aaacggaggt agactgcgag ttcttacgga gatgctgcga gaatctaacg    780
gaagagaacc gtcggctaca aaaagaagta acggaattga gagcacttaa gctctctcct    840
cagttctaca tgcacatgag cccacccact actttgacca tgtgcccttc atgtgaacac    900
gtgtcggtcc cgccaccaca acctcaggct gctacgtcag cgcaccaccg gtcgttgccg    960
gtcaatgcgt gggctcctgc gacgaggata tctcacggct tgacttttga cgctcttcgt   1020
cctaggtcct aa                                                        1032

<210> SEQ ID NO 129
<211> LENGTH: 682
<212> TYPE: DNA
<213> ORGANISM: artificial sequence
<220> FEATURE:
<223> OTHER INFORMATION: G481:EDLL:cMyc fusion

<400> SEQUENCE: 129
atggcggata cgccttcgag cccagctgga gatggcggag aaagcggcgg ttccgttagg     60
gagcaggatc gataccttcc tatagctaat atcagcagga tcatgaagaa agcgttgcct    120
cctaatggta agattggaaa agatgctaag gatacagttc aggaatgcgt ctctgagttc    180
atcagcttca tcactagcga ggccagtgat aagtgtcaaa agagaaaag gaaaactgtg    240 aatggtgatg atttgttgtg ggcaatggca acattaggat tgaggattac ctggaacct    300 ctaaagatat acctagcgag gtacaggag ttggagggtg ataataaggg atcaggaaag    360
agtggagatg atcaaatag agatgctggt ggcggtgttt ctggtgaaga atgccgagc    420 tggcatatgg aagttttcga gtttgagtat ttggacgata aggttcttga agaacttctt    480
gattcagaag aaaggaagag agagctcggg ttaattaacg gtgaacaaaa gctaatctcc    540
gaggaagact gaacggtga acaaaaatta atctcagaag aagacttgaa cggactcgac    600
ggtgaacaaa agttgatttc tgaagaagat ttgaacggtg aacaaaagct aatctccgag    660
gaagacttga acggtagctg aa                                             682

<210> SEQ ID NO 130
<211> LENGTH: 1110
<212> TYPE: DNA
<213> ORGANISM: artificial sequence
<220> FEATURE:
<223> OTHER INFORMATION: G400:EDLL:cMyc fusion

<400> SEQUENCE: 130
atgatgttcg agaaagacga tctgggtcta agcttaggct tgaattttcc aaagaaacag     60
atcaatctca aatcaaatcc atctgtttct gttactcctt cttcttcttc ttttggatta    120
ttcagaagat cttcatggaa cgagagtttt acttcttcag ttccaaactc agattcgtca    180
caaaaagaaa caagaacttt catccgagga atcgacgtga acagaccacc gtctacagcg    240
gaatacggcg acgaagacgc tggagtatct tcacctaaca gtacagtctc aagctctaca    300
gggaaaagaa gcgagagaga agaagacaca gatccacaag gctcaagagg aatcagtgac    360
gatgaagatg gtgataactc caggaaaag cttagacttt ccaaagatca atctgctatt    420
cttgaagaga ccttcaaaga tcacagtact ctcaatccga agcagaagca agcattggct    480
aaacaattag ggttacgagc aagacaagtg gaagtttggt ttcagaacag acgagcaaga    540
acaaagctga gcaaacggaa ggtagactgc gagttcttac ggagatgctg cgagaatcta    600
acggaagaga accgtcggct acaaaaagaa gtaacggaat tgagagcact taagctctct    660
```

```
cctcagttct acatgcacat gagcccaccc actactttga ccatgtgccc ttcatgtgaa      720
cacgtgtcgg tcccgccacc acaacctcag gctgctacgt cagcgcacca ccggtcgttg      780
ccggtcaatg cgtgggctcc tgcgacgagg atatctcacg gcttgacttt tgacgctctt      840
cgtcctaggt cccatatgga agttttcgag tttgagtatt tggacgataa ggttcttgaa      900
gaacttcttg attcagaaga aaggaagaga gagctcgggt taattaacgg tgaacaaaag      960
ctaatctccg aggaagactt gaacggtgaa caaaaattaa tctcagaaga agacttgaac     1020
ggactcgacg gtgaacaaaa gttgatttct gaagaagatt tgaacggtga acaaaagcta     1080
atctccgagg aagacttgaa cggtagctga                                      1110
```

<210> SEQ ID NO 131
<211> LENGTH: 190
<212> TYPE: PRT
<213> ORGANISM: Arabidopsis thaliana
<220> FEATURE:
<223> OTHER INFORMATION: G482 polypeptide

<400> SEQUENCE: 131

```
Met Gly Asp Ser Asp Arg Asp Ser Gly Gly Gly Gln Asn Gly Asn Asn
1               5                   10                  15

Gln Asn Gly Gln Ser Ser Leu Ser Pro Arg Glu Gln Asp Arg Phe Leu
            20                  25                  30

Pro Ile Ala Asn Val Ser Arg Ile Met Lys Lys Ala Leu Pro Ala Asn
        35                  40                  45

Ala Lys Ile Ser Lys Asp Ala Lys Glu Thr Met Gln Glu Cys Val Ser
    50                  55                  60

Glu Phe Ile Ser Phe Val Thr Gly Glu Ala Ser Asp Lys Cys Gln Lys
65                  70                  75                  80

Glu Lys Arg Lys Thr Ile Asn Gly Asp Asp Leu Leu Trp Ala Met Thr
                85                  90                  95

Thr Leu Gly Phe Glu Asp Tyr Val Glu Pro Leu Lys Val Tyr Leu Gln
            100                 105                 110

Arg Phe Arg Glu Ile Glu Gly Glu Arg Thr Gly Leu Gly Arg Pro Gln
        115                 120                 125

Thr Gly Gly Glu Val Gly Glu His Gln Arg Asp Ala Val Gly Asp Gly
    130                 135                 140

Gly Gly Phe Tyr Gly Gly Gly Gly Met Gln Tyr His Gln His His
145                 150                 155                 160

Gln Phe Leu His Gln Gln Asn His Met Tyr Gly Ala Thr Gly Gly Gly
                165                 170                 175

Ser Asp Ser Gly Gly Gly Ala Ala Ser Gly Arg Thr Arg Thr
            180                 185                 190
```

<210> SEQ ID NO 132
<211> LENGTH: 194
<212> TYPE: PRT
<213> ORGANISM: Arabidopsis thaliana
<220> FEATURE:
<223> OTHER INFORMATION: G1274 polypeptide

<400> SEQUENCE: 132

```
Met Asn Ile Ser Gln Asn Pro Ser Pro Asn Phe Thr Tyr Phe Ser Asp
1               5                   10                  15

Glu Asn Phe Ile Asn Pro Phe Met Asp Asn Asn Asp Phe Ser Asn Leu
            20                  25                  30
```

Met Phe Phe Asp Ile Asp Glu Gly Gly Asn Asn Gly Leu Ile Glu Glu
            35                  40                  45

Glu Ile Ser Ser Pro Thr Ser Ile Val Ser Ser Glu Thr Phe Thr Gly
 50                  55                  60

Glu Ser Gly Gly Ser Gly Ser Ala Thr Thr Leu Ser Lys Lys Glu Ser
65                  70                  75                  80

Thr Asn Arg Gly Ser Lys Glu Ser Asp Gln Thr Lys Glu Thr Gly His
                85                  90                  95

Arg Val Ala Phe Arg Thr Arg Ser Lys Ile Asp Val Met Asp Asp Gly
            100                 105                 110

Phe Lys Trp Arg Lys Tyr Gly Lys Lys Ser Val Lys Asn Asn Ile Asn
        115                 120                 125

Lys Arg Asn Tyr Tyr Lys Cys Ser Ser Glu Gly Cys Ser Val Lys Lys
130                 135                 140

Arg Val Glu Arg Asp Gly Asp Asp Ala Ala Tyr Val Ile Thr Thr Tyr
145                 150                 155                 160

Glu Gly Val His Asn His Glu Ser Leu Ser Asn Val Tyr Tyr Asn Glu
                165                 170                 175

Met Val Leu Ser Tyr Asp His Asp Asn Trp Asn Gln His Ser Leu Leu
            180                 185                 190

Arg Ser

<210> SEQ ID NO 133
<211> LENGTH: 344
<212> TYPE: PRT
<213> ORGANISM: Arabidopsis thaliana
<220> FEATURE:
<223> OTHER INFORMATION: G867 polypeptide

<400> SEQUENCE: 133

Met Glu Ser Ser Ser Val Asp Glu Ser Thr Thr Ser Thr Gly Ser Ile
1               5                   10                  15

Cys Glu Thr Pro Ala Ile Thr Pro Ala Lys Lys Ser Ser Val Gly Asn
            20                  25                  30

Leu Tyr Arg Met Gly Ser Gly Ser Ser Val Val Leu Asp Ser Glu Asn
        35                  40                  45

Gly Val Glu Ala Glu Ser Arg Lys Leu Pro Ser Ser Lys Tyr Lys Gly
 50                  55                  60

Val Val Pro Gln Pro Asn Gly Arg Trp Gly Ala Gln Ile Tyr Glu Lys
65                  70                  75                  80

His Gln Arg Val Trp Leu Gly Thr Phe Asn Glu Glu Asp Glu Ala Ala
                85                  90                  95

Arg Ala Tyr Asp Val Ala Val His Arg Phe Arg Arg Arg Asp Ala Val
            100                 105                 110

Thr Asn Phe Lys Asp Val Lys Met Asp Glu Asp Glu Val Asp Phe Leu
        115                 120                 125

Asn Ser His Ser Lys Ser Glu Ile Val Asp Met Leu Arg Lys His Thr
130                 135                 140

Tyr Asn Glu Glu Leu Glu Gln Ser Lys Arg Arg Arg Asn Gly Asn Gly
145                 150                 155                 160

Asn Met Thr Arg Thr Leu Leu Thr Ser Gly Leu Ser Asn Asp Gly Val
                165                 170                 175

Ser Thr Thr Gly Phe Arg Ser Ala Glu Ala Leu Phe Glu Lys Ala Val
            180                 185                 190

Thr Pro Ser Asp Val Gly Lys Leu Asn Arg Leu Val Ile Pro Lys His

```
                195                 200                 205
    His Ala Glu Lys His Phe Pro Leu Pro Ser Ser Asn Val Ser Val Lys
        210                 215                 220

Gly Val Leu Leu Asn Phe Glu Asp Val Asn Gly Lys Val Trp Arg Phe
    225                 230                 235                 240

Arg Tyr Ser Tyr Trp Asn Ser Ser Gln Ser Tyr Val Leu Thr Lys Gly
                    245                 250                 255

Trp Ser Arg Phe Val Lys Glu Lys Asn Leu Arg Ala Gly Asp Val Val
                260                 265                 270

Ser Phe Ser Arg Ser Asn Gly Gln Asp Gln Leu Tyr Ile Gly Trp
                275                 280                 285

Lys Ser Arg Ser Gly Ser Asp Leu Asp Ala Gly Arg Val Leu Arg Leu
        290                 295                 300

Phe Gly Val Asn Ile Ser Pro Glu Ser Ser Arg Asn Asp Val Val Gly
    305                 310                 315                 320

Asn Lys Arg Val Asn Asp Thr Glu Met Leu Ser Leu Val Cys Ser Lys
                    325                 330                 335

Lys Gln Arg Ile Phe His Ala Ser
                340

<210> SEQ ID NO 134
<211> LENGTH: 228
<212> TYPE: PRT
<213> ORGANISM: Arabidopsis thaliana
<220> FEATURE:
<223> OTHER INFORMATION: G1760 polypeptide

<400> SEQUENCE: 134

Met Gly Arg Gly Lys Ile Val Ile Gln Arg Ile Asp Asp Ser Thr Ser
    1               5                   10                  15

Arg Gln Val Thr Phe Ser Lys Arg Arg Lys Gly Leu Ile Lys Lys Ala
                    20                  25                  30

Lys Glu Leu Ala Ile Leu Cys Asp Ala Glu Val Gly Leu Ile Ile Phe
                35                  40                  45

Ser Ser Thr Gly Lys Leu Tyr Asp Phe Ala Ser Ser Ser Met Lys Ser
        50                  55                  60

Val Ile Asp Arg Tyr Asn Lys Ser Lys Ile Glu Gln Gln Gln Leu Leu
    65                  70                  75                  80

Asn Pro Ala Ser Glu Val Lys Phe Trp Gln Arg Glu Ala Ala Val Leu
                    85                  90                  95

Arg Gln Glu Leu His Ala Leu Gln Glu Asn His Arg Gln Met Met Gly
                100                 105                 110

Glu Gln Leu Asn Gly Leu Ser Val Asn Glu Leu Asn Ser Leu Glu Asn
            115                 120                 125

Gln Ile Glu Ile Ser Leu Arg Gly Ile Arg Met Arg Lys Glu Gln Leu
        130                 135                 140

Leu Thr Gln Glu Ile Gln Glu Leu Ser Gln Lys Arg Asn Leu Ile His
    145                 150                 155                 160

Gln Glu Asn Leu Asp Leu Ser Arg Lys Val Gln Arg Ile His Gln Glu
                    165                 170                 175

Asn Val Glu Leu Tyr Lys Lys Ala Tyr Met Ala Asn Thr Asn Gly Phe
                180                 185                 190

Thr His Arg Glu Val Ala Val Ala Asp Asp Glu Ser His Thr Gln Ile
            195                 200                 205

Arg Leu Gln Leu Ser Gln Pro Glu His Ser Asp Tyr Asp Thr Pro Pro
```

-continued

```
                210                 215                 220

Arg Ala Asn Glu
225

<210> SEQ ID NO 135
<211> LENGTH: 232
<212> TYPE: PRT
<213> ORGANISM: Arabidopsis thaliana
<220> FEATURE:
<223> OTHER INFORMATION: G913 polypeptide

<400> SEQUENCE: 135

Met Ser Asn Asn Asn Ser Pro Thr Thr Val Asn Gln Glu Thr Thr
1               5                   10                  15

Thr Ser Arg Glu Val Ser Ile Thr Leu Pro Thr Asp Gln Ser Pro Gln
                20                  25                  30

Thr Ser Pro Gly Ser Ser Ser Pro Ser Pro Arg Pro Ser Gly Gly
            35                  40                  45

Ser Pro Ala Arg Arg Thr Ala Thr Gly Leu Ser Gly Lys His Ser Ile
        50                  55                  60

Phe Arg Gly Ile Arg Leu Arg Asn Gly Lys Trp Val Ser Glu Ile Arg
65                  70                  75                  80

Glu Pro Arg Lys Thr Thr Arg Ile Trp Leu Gly Thr Tyr Pro Val Pro
                85                  90                  95

Glu Met Ala Ala Ala Tyr Asp Val Ala Ala Leu Ala Leu Lys Gly
                100                 105                 110

Pro Asp Ala Val Leu Asn Phe Pro Gly Leu Ala Leu Thr Tyr Val Ala
        115                 120                 125

Pro Val Ser Asn Ser Ala Ala Asp Ile Arg Ala Ala Ser Arg Ala
130                 135                 140

Ala Glu Met Lys Gln Pro Asp Gln Gly Gly Asp Glu Lys Val Leu Glu
145                 150                 155                 160

Pro Val Gln Pro Gly Lys Glu Glu Leu Glu Val Ser Cys Asn
                165                 170                 175

Ser Cys Ser Leu Glu Phe Met Asp Glu Glu Ala Met Leu Asn Met Pro
                180                 185                 190

Thr Leu Leu Thr Glu Met Ala Glu Gly Met Leu Met Ser Pro Pro Arg
            195                 200                 205

Met Met Ile His Pro Thr Met Glu Asp Asp Ser Pro Glu Asn His Glu
        210                 215                 220

Gly Asp Asn Leu Trp Ser Tyr Lys
225                 230

<210> SEQ ID NO 136
<211> LENGTH: 224
<212> TYPE: PRT
<213> ORGANISM: Arabidopsis thaliana
<220> FEATURE:
<223> OTHER INFORMATION: G912 polypeptide

<400> SEQUENCE: 136

Met Asn Pro Phe Tyr Ser Thr Phe Pro Asp Ser Phe Leu Ser Ile Ser
1               5                   10                  15

Asp His Arg Ser Pro Val Ser Asp Ser Ser Glu Cys Ser Pro Lys Leu
                20                  25                  30

Ala Ser Ser Cys Pro Lys Lys Arg Ala Gly Arg Lys Lys Phe Arg Glu
            35                  40                  45
```

Thr Arg His Pro Ile Tyr Arg Gly Val Arg Gln Arg Asn Ser Gly Lys
 50                  55                  60

Trp Val Cys Glu Val Arg Glu Pro Asn Lys Lys Ser Arg Ile Trp Leu
 65                  70                  75                  80

Gly Thr Phe Pro Thr Val Glu Met Ala Ala Arg Ala His Asp Val Ala
                     85                  90                  95

Ala Leu Ala Leu Arg Gly Arg Ser Ala Cys Leu Asn Phe Ala Asp Ser
                100                 105                 110

Ala Trp Arg Leu Arg Ile Pro Glu Thr Thr Cys Pro Lys Glu Ile Gln
                115                 120                 125

Lys Ala Ala Ser Glu Ala Ala Met Ala Phe Gln Asn Glu Thr Thr Thr
130                 135                 140

Glu Gly Ser Lys Thr Ala Ala Glu Ala Glu Ala Ala Gly Glu Gly
145                 150                 155                 160

Val Arg Glu Gly Glu Arg Arg Ala Glu Gln Asn Gly Gly Val Phe
                165                 170                 175

Tyr Met Asp Asp Glu Ala Leu Leu Gly Met Pro Asn Phe Phe Glu Asn
                180                 185                 190

Met Ala Glu Gly Met Leu Leu Pro Pro Glu Val Gly Trp Asn His
                195                 200                 205

Asn Asp Phe Asp Gly Val Gly Asp Val Ser Leu Trp Ser Phe Asp Glu
210                 215                 220

<210> SEQ ID NO 137
<211> LENGTH: 258
<212> TYPE: PRT
<213> ORGANISM: Arabidopsis thaliana
<220> FEATURE:
<223> OTHER INFORMATION: G2932 polypeptide

<400> SEQUENCE: 137

Met Cys Ala Leu Val Pro Pro Leu Phe Pro Asn Phe Gly Trp Pro Ser
1                   5                   10                  15

Thr Gly Glu Tyr Asp Ser Tyr Tyr Leu Ala Gly Asp Ile Leu Asn Asn
                20                  25                  30

Gly Gly Phe Leu Asp Phe Pro Val Pro Glu Glu Thr Tyr Gly Ala Val
                35                  40                  45

Thr Ala Val Thr Gln His Gln Asn Ser Phe Gly Val Ser Val Ser Ser
 50                  55                  60

Glu Gly Asn Glu Ile Asp Asn Pro Val Val Lys Lys Leu Asn
 65                  70                  75                  80

His Asn Ala Ser Glu Arg Asp Arg Arg Lys Ile Asn Ser Leu Phe
                 85                  90                  95

Ser Ser Leu Arg Ser Cys Leu Pro Ala Ser Gly Gln Ser Lys Lys Leu
                100                 105                 110

Ser Ile Pro Ala Thr Val Ser Arg Ser Leu Lys Tyr Ile Pro Glu Leu
                115                 120                 125

Gln Glu Gln Val Lys Lys Leu Ile Lys Lys Glu Glu Leu Leu Val
130                 135                 140

Gln Ile Ser Gly Gln Arg Asn Thr Glu Cys Tyr Val Lys Gln Pro Pro
145                 150                 155                 160

Lys Ala Val Ala Asn Tyr Ile Ser Thr Val Ser Ala Thr Arg Leu Gly
                165                 170                 175

Asp Asn Glu Val Met Val Gln Ile Ser Ser Ser Lys Ile His Asn Phe
                180                 185                 190

Ser Ile Ser Asn Val Leu Ser Gly Leu Glu Glu Asp Arg Phe Val Leu
                195                 200                 205

Val Asp Met Ser Ser Arg Ser Gln Gly Arg Leu Phe Tyr Thr
210                 215                 220

Leu His Leu Gln Val Glu Lys Ile Glu Asn Tyr Lys Leu Asn Cys Glu
225                 230                 235                 240

Glu Leu Ser Gln Arg Met Leu Tyr Leu Tyr Glu Cys Gly Asn Ser
                245                 250                 255

Tyr Ile

<210> SEQ ID NO 138
<211> LENGTH: 272
<212> TYPE: PRT
<213> ORGANISM: Arabidopsis thaliana
<220> FEATURE:
<223> OTHER INFORMATION: G926 polypeptide

<400> SEQUENCE: 138

Met Gln Ser Lys Pro Gly Arg Glu Asn Glu Glu Val Asn Asn His
1               5                   10                  15

His Ala Val Gln Gln Pro Met Met Tyr Ala Glu Pro Trp Trp Lys Asn
                20                  25                  30

Asn Ser Phe Gly Val Val Pro Gln Ala Arg Pro Ser Gly Ile Pro Ser
            35                  40                  45

Asn Ser Ser Ser Leu Asp Cys Pro Asn Gly Ser Glu Ser Asn Asp Val
        50                  55                  60

His Ser Ala Ser Glu Asp Gly Ala Leu Asn Gly Glu Asn Asp Gly Thr
65                  70                  75                  80

Trp Lys Asp Ser Gln Ala Ala Thr Ser Ser Arg Ser Val Asp Asn His
                85                  90                  95

Gly Met Glu Gly Asn Asp Pro Ala Leu Ser Ile Arg Asn Met His Asp
            100                 105                 110

Gln Pro Leu Val Gln Pro Glu Leu Val Gly His Tyr Ile Ala Cys
        115                 120                 125

Val Pro Asn Pro Tyr Gln Asp Pro Tyr Tyr Gly Gly Leu Met Gly Ala
130                 135                 140

Tyr Gly His Gln Gln Leu Gly Phe Arg Pro Tyr Leu Gly Met Pro Arg
145                 150                 155                 160

Glu Arg Thr Ala Leu Pro Leu Asp Met Ala Gln Glu Pro Val Tyr Val
                165                 170                 175

Asn Ala Lys Gln Tyr Glu Gly Ile Leu Arg Arg Arg Lys Ala Arg Ala
            180                 185                 190

Lys Ala Glu Leu Glu Arg Lys Val Ile Arg Asp Arg Lys Pro Tyr Leu
        195                 200                 205

His Glu Ser Arg His Lys His Ala Met Arg Arg Ala Arg Ala Ser Gly
210                 215                 220

Gly Arg Phe Ala Lys Lys Ser Glu Val Glu Ala Gly Glu Asp Ala Gly
225                 230                 235                 240

Gly Arg Asp Arg Glu Arg Gly Ser Ala Thr Asn Ser Ser Gly Ser Glu
                245                 250                 255

Gln Val Glu Thr Asp Ser Asn Glu Thr Leu Asn Ser Ser Gly Ala Pro
            260                 265                 270

<210> SEQ ID NO 139
<211> LENGTH: 234
<212> TYPE: PRT

```
<213> ORGANISM: Arabidopsis thaliana
<220> FEATURE:
<223> OTHER INFORMATION: G715 polypeptide

<400> SEQUENCE: 139

Met Asp Thr Asn Asn Gln Gln Pro Pro Pro Ser Ala Ala Gly Ile Pro
 1               5                  10                  15

Pro Pro Pro Pro Gly Thr Thr Ile Ser Ala Ala Gly Gly Gly Ala Ser
            20                  25                  30

Tyr His His Leu Leu Gln Gln Gln Gln Gln Leu Gln Leu Phe Trp
            35                  40                  45

Thr Tyr Gln Arg Gln Glu Ile Glu Gln Val Asn Asp Phe Lys Asn His
        50                  55                  60

Gln Leu Pro Leu Ala Arg Ile Lys Lys Ile Met Lys Ala Asp Glu Asp
65                  70                  75                  80

Val Arg Met Ile Ser Ala Glu Ala Pro Ile Leu Phe Ala Lys Ala Cys
                85                  90                  95

Glu Leu Phe Ile Leu Glu Leu Thr Ile Arg Ser Trp Leu His Ala Glu
               100                 105                 110

Glu Asn Lys Arg Arg Thr Leu Gln Lys Asn Asp Ile Ala Ala Ala Ile
               115                 120                 125

Thr Arg Thr Asp Ile Phe Asp Phe Leu Val Asp Ile Val Pro Arg Asp
        130                 135                 140

Glu Ile Lys Asp Glu Ala Ala Val Leu Gly Gly Gly Met Val Val Ala
145                 150                 155                 160

Pro Thr Ala Ser Gly Val Pro Tyr Tyr Tyr Pro Pro Met Gly Gln Pro
                165                 170                 175

Ala Gly Pro Gly Gly Met Met Ile Gly Arg Pro Ala Met Asp Pro Asn
               180                 185                 190

Gly Val Tyr Val Gln Pro Pro Ser Gln Ala Trp Gln Ser Val Trp Gln
           195                 200                 205

Thr Ser Thr Gly Thr Gly Asp Asp Val Ser Tyr Gly Ser Gly Gly Ser
        210                 215                 220

Ser Gly Gln Gly Asn Leu Asp Gly Gln Gly
225                 230
```

STRONG ACTIVATION DOMAIN

This application is a continuation application of U.S. application Ser. No. 13/000,488, filed on Feb. 4, 2011 (pending), which is the 35 U.S.C. 371 National Stage of International Application No. PCT/US09/048,814, filed Jun. 26, 2009, which claims the benefit of U.S. Provisional Application No. 61/076,534, filed Jun. 27, 2008. This application is a continuation-in-part of U.S. application Ser. No. 12/705,845, filed on 15 Feb. 2010 (pending), which is a continuation-in-part of U.S. application Ser. No. 10/714,887, filed on Nov. 13, 2003 (now abandoned). U.S. application Ser. No. 12/705,845 is also a continuation-in-part of U.S. application Ser. No. 11/981,576, filed Oct. 30, 2007, which issued as U.S. Pat. No. 7,888,558 on Feb. 15, 2011. This application is also a continuation-in-part of U.S. application Ser. No. 10/903,236, filed on Jul. 30, 2004 (pending). All the above-referenced applications are hereby incorporated by reference in their entirety.

FIELD OF THE INVENTION

The present invention relates to plant genomics and plant improvement, and modifying gene and protein expression.

BACKGROUND OF THE INVENTION

A transcriptional activation domain (TAD) is the region of a transcription factor (TF) protein that is necessary for its transcriptional activation activity when bound to a promoter. The TAD can be present at any location in the protein. These sequences are usually transportable, that is, they retain activation function when isolated from their native proteins and fused to any sequence specific DNA binding domain (DBD) protein. Hence, a TAD:DBD fusion can be used to turn on the expression of any desired target gene, when the promoter of that target gene contains a specific DNA sequence bound by the DBD. This property of TADs extends their utility in various agriculture and medicinal research. TADs are routinely being used in the study of protein-protein and protein-DNA interactions, and also being used for the targeted induction of genes in plants, animals and yeast.

TADs can be classified into three major classes depending upon their amino acid composition: proline-rich, glutamine-rich and acidic-rich. Most well characterized TADs, which confer strong transcriptional activation potential, including the yeast activator protein GAL4 and the VP16 protein from herpes simplex virus, fall in the category of acidic activators. These activation domains, though they are typically large in size, are routinely used for inducing gene expression, and for, protein-protein and protein-DNA interaction studies in yeast, plants and other animal science research.

The acidic activators form an amphipathic structure, that is, the activation domain contains many acidic and polar amino acids residues interspersed with hydrophobic residues. Such stretches of acidic amino acids are widely distributed in various proteins, but all regions rich in acidic amino acids do not necessarily have role in activation. Due to the loose consensus in the amino acid sequence conservation among activators, it is difficult to predict whether or not a given protein sequence has a role in transcriptional activation.

Activation domains that presently used in the art are generally derived from non-plant proteins such as GAL4 protein (yeast) and VP16 viral protein (herpes simplex virus). Due to their large size, fusion of these domains to a TF can lead to a change in the native structure which compromises the function of that TF. In addition, it may be considered undesirable to use sequences from non-plant proteins in plants destined for commercial use as transgenic crops, particularly those grown for food purposes.

SUMMARY OF THE INVENTION

The EDLL domain is a new activation domain identified from a plant protein. It is highly active when fused with different classes of proteins from plants and yeast, and has activation potential comparable to the widely used VP16 activation domain. Unlike other known strong activation domains such as VP16 and GAL4, EDLL is relatively small in size; fusion of such a small peptide to any protein has a lower chance of altering the native conformation of the fusion protein. The EDLL domain is also present in many plant species, including useful crop species such as rice, maize, soybean and alfalfa. The EDLL domain from these crops or from other plant species can be fused with transcription factors isolated from the same species, or other plant species, and can be used for enhanced induction of any target genes in those crop varieties. This approach affords enhanced activation of TF targets while avoiding contamination of the crop genome with expressed genetic materials derived from outside of the plant kingdom.

The invention thus pertains to a chimeric polypeptide that may be used to increase the expression of a polynucleotide sequence in a host cell or plant. The chimeric polypeptide comprises a transcription activation domain that is covalently fused to a transcription regulatory polypeptide, containing a DBD. The transcription activation domain generally comprises the consensus sequence $EX_4DX_3LX_3L$ (SEQ ID NO: 55), or the consensus sequence E-L/F-$X_2$-L/F-D-D/N-$X_2$-L-$X_2$-L/M-L (SEQ ID NO: 56), or the consensus sequence E-F/L-X-X-L/F-D-D/N-X-V/L/I-L-X-X-L/M-L (SEQ ID NO: 94), or the consensus sequence E-F/L-E/V-Y/C/F-L/F-D-D/N-X-V/L-L-E/Q/D-E/D/S-L/M-L (SEQ ID NO: 95).

Specific examples of activation domains described by the consensus sequence SEQ ID NOs: 55, 56, 94 or 95 are provided. The transcription activation domain and the transcription regulatory protein within the chimeric polypeptide do not occur in nature in the same polypeptide, or do not occur in nature with the same order or orientation or with the same spacing within the same peptide, that is, they are mutually heterologous. The transcription activation domain and the transcription regulatory protein in the chimeric polypeptide also do not occur in the same copy number or configuration in nature.

The chimeric polypeptide is able to activate the transcription of a target polynucleotide sequence to which the chimeric polypeptide binds.

The invention also pertains to a nucleic acid construct encoding a chimeric polypeptide, as described in the preceding paragraph, that may be used to increase the expression of a polynucleotide sequence after introducing the nucleic acid construct into a host cell.

The invention is also directed to host cells and transgenic plants that are transformed with the nucleic acid construct described in the preceding paragraph.

The invention is also directed to a method for increasing the expression of a polynucleotide sequence in a host cell by introducing the nucleic acid construct described above into the host cell.

BRIEF DESCRIPTION OF THE SEQUENCE LISTING AND DRAWINGS

The Sequence Listing provides exemplary polynucleotide and polypeptide sequences of the invention. The traits associated with the use of the sequences are included in the Examples.

Incorporation of the Sequence Listing

The copy of the Sequence Listing being submitted electronically with this patent application, provided under 37 CFR § 1.821-1.825, is a read-only memory computer-readable file in ASCII text format. The Sequence Listing is named "MBI-0084CON_ST25.txt", the electronic file of the Sequence Listing was created on Nov. 8, 2013, and is 123 kilobytes in size (measured in MS-WINDOWS). The Sequence Listing is herein incorporated by reference in its entirety.

FIG. 1 shows an optimal alignment of the conserved "EDLL" activation domain found in AP2 transcription factors orthologous to the *Arabidopsis* AtERF98 (G1792) protein (these proteins and other phylogenetically- and closely-related sequences constitute the "G1792 Glade"). Functional G1792 Glade members contain, at relative positions, a glutamic acid residue at position 3, an aspartic acid residue at position 8, and a leucine residue at positions 12 and 16. FIG. 1 also provides a sequence logo of the EDLL domain, which consists of stacks of symbols, one stack for each position in the sequence. The overall height of the stack at any position indicates the sequence conservation at that position, while the height of symbols within the stack indicates the relative frequency of each amino or nucleic acid at that position (see Schneider et al. (1990) *Nucleic Acids Res.* 18: 6097-6100; Crooks et al. (2004) *Genome Res.* 14: 1188-1190; or weblogo.berkeley.edu). This sequence logo thus provides a graphical representation of the relative frequencies of the amino acids found in this alignment and in the Sequence listing in the EDLL consensus sequence SEQ ID NO: 95.

FIG. 2 illustrates the results of experiments to demonstrate experimentally the function of the EDLL motif. A 24 amino acid motif comprising the EDLL domain (SEQ ID NO: 37) of AtERF98 (G1792; SEQ ID NO: 2) was fused with a sequence-specific GAL4 DNA binding domain (DBD; encoded by SEQ ID NO: 117) from yeast (GAL4 DBD or "GD"). The chimeric protein, ("GD-EDLL" in this figure; (SEQ ID NO: 118), when expressed in plant protoplasts, induced the expression of a GUS (β-glucuronidase) reporter gene containing GAL4 DBD binding sequences in the promoter (the GUS reporter system makes use of the fluorescent β-glucuronidase substrate, 4-methylumbelliferyl beta-D-glucuronide (MUG), to determine the expression level of the GUS gene). The GAL4 DBD without the EDLL motif ("GD" in this figure; encoded by SEQ ID NO: 117) could not induce the expression of the reporter gene significantly. The activation of the reporter gene by EDLL motif is comparable in magnitude to that obtained with the widely used VP16 activation domain from herpes simplex virus (comparing "GD-VP16", encoded by SEQ ID NO: 122, and GD-EDLL, encoded by SEQ ID NO: 118, in this figure). When the conserved hydrophobic leucine residues were changed to valine ("EDLLm"; encoded by SEQ ID NO: 119), the activation potential of EDLL motif was significantly compromised.

Figure 3:
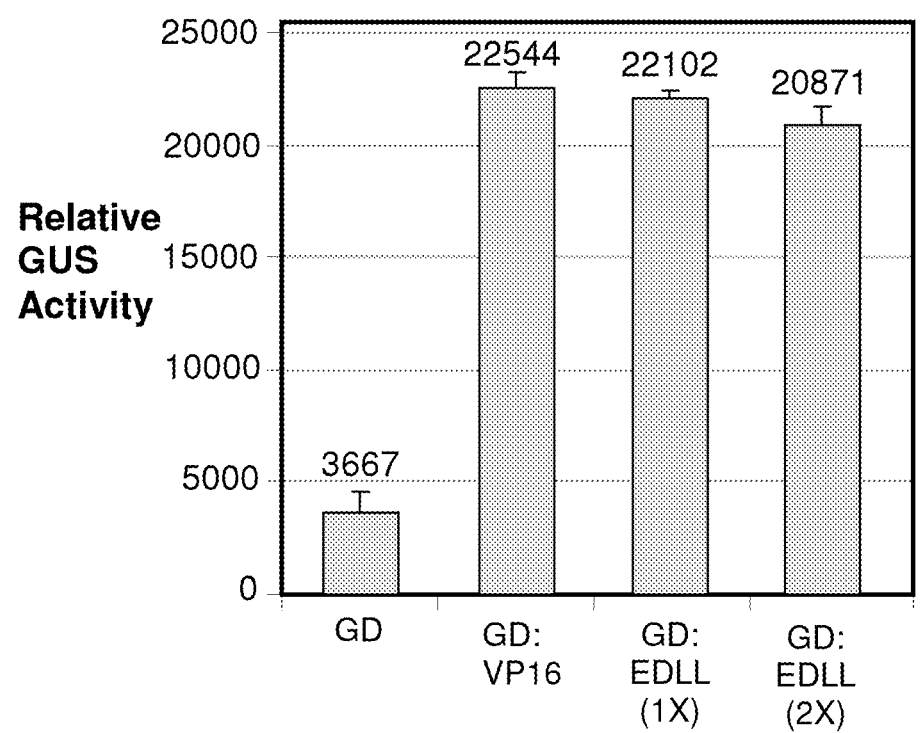

FIG. 3 shows a graph of relative functional activity determined by either fusing one or two copies of the AtERF98 (G1792) EDLL domain (SEQ ID NO: 37) to a sequence-specific GAL4 DNA binding domain from yeast (encoded by SEQ ID NO: 117), and co-expressing these constructs in plant protoplasts with a reporter construct comprising GAL4-UAS fused to a GUS sequence (as described above for FIG. 2). When either one copy [GD:EDLL(1×)] or two copies [GD:EDLL(2×)] of the AtERF98 EDLL motif are fused to the GAL4 DNA binding domain, reporter gene activity was significantly higher than with the GAL4 DNA binding domain alone (GD), and comparable to the activity obtained with a VP16 activation domain (GD:VP16).

Figure 4:
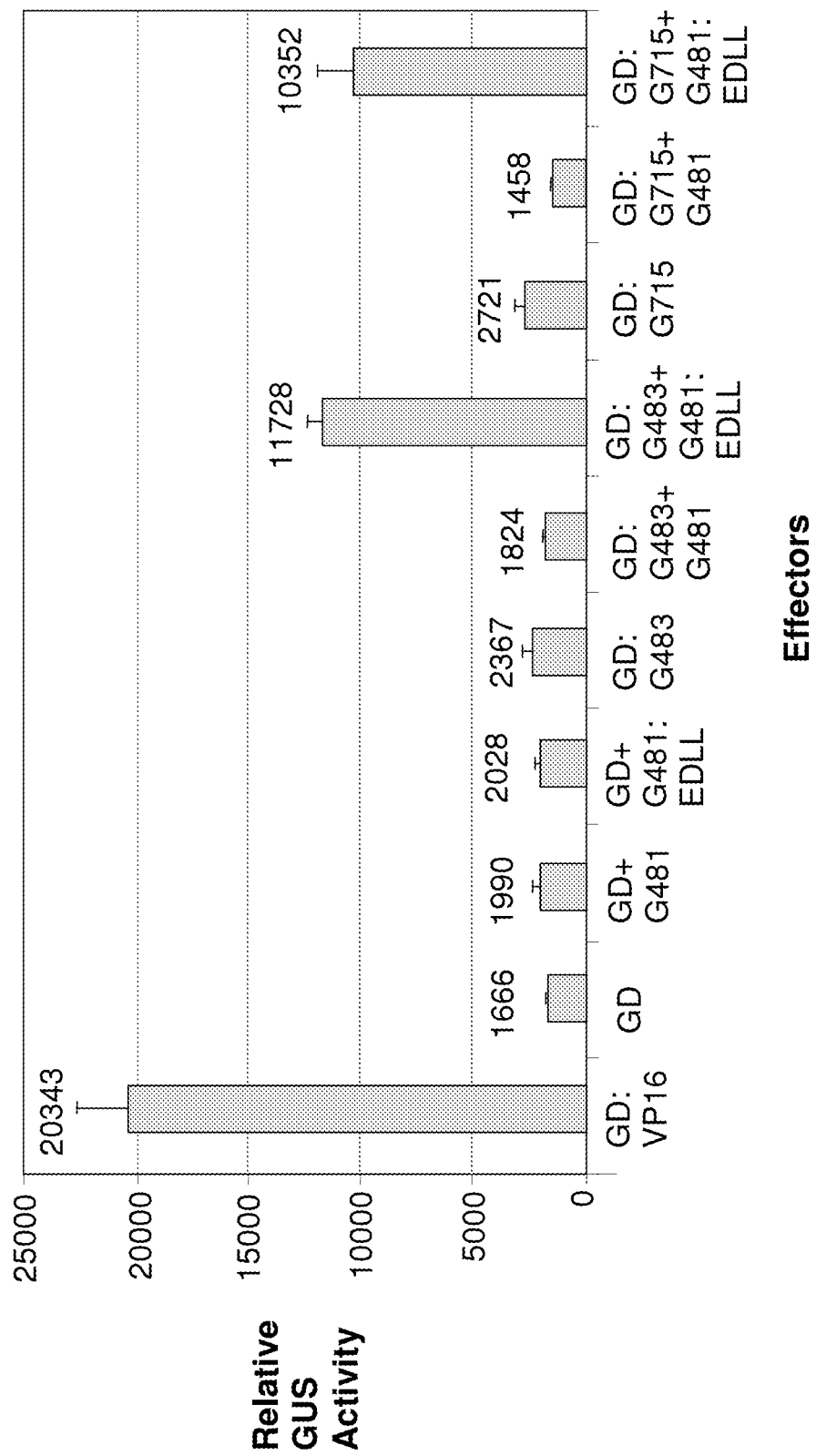

The results provided in FIG. 4 demonstrate that the EDLL motif confers transcriptional activation function to a plant sequence specific DNA binding transcription factor, specifically NF-YB1 (G481, SEQ ID NO: 73). NF-Y (Nuclear Factor-Y) proteins, also referred to as CCAAT sequence binding proteins, consist of three subunits; NF-YA, NF-YB, and NF-YC, all of which are necessary for DNA binding. NF-YB proteins interact with NF-YC proteins as part of a heterotrimeric DNA binding complex (the NF-YB/NF-YC heterodimer is translocated into the nucleus, the NF-YA subunit interacts with the NF-YB:NF-YC heterodimer, and the resulting complex is able to recognize and bind to a "CCAAT" penta-nucleotide element), and this interaction can be detected in plant protoplasts in a two-hybrid assay, with one protein fused to an activation domain and another fused to a DNA binding domain. To demonstrate the utility of the EDLL domain in activating transcription when fused to a heterologous transcription factor, the EDLL motif of AtERF98 was fused to G481 (an NF-YB subunit; SEQ ID NO: 96), and the yeast GAL4 DNA binding domain (GD; encoded by SEQ ID NO: 117) was fused to G483 (SEQ ID NO: 74; an NF-YC subunit). When the GD:G483 chimeric protein (encoded by SEQ ID NO: 121) was expressed in plant protoplasts along with a reporter gene containing GAL4 binding sequences, the GD-G483 chimeric protein alone could not induce reporter gene activity. When G481 (SEQ ID NO: 73) was co-expressed without an EDLL fusion and GD-G483 in protoplasts, the G481+G483 dimer could also not induce the activity of the reporter gene. This indicated that the NF-YB/NF-YC dimer alone is not sufficient to induce the reporter gene activity. When the G481:EDLL fusion (encoded by SEQ ID NO: 96) was co-expressed with GD:G483 in the protoplasts, the G481: EDLL/GD:G483 dimer induced the activity of reporter gene to a significant degree. This interaction was specific to the dimerization of G481 and G483, because the G481:EDLL fusion did not activate the reporter gene when co-expressed with the GD alone (GD+G481:EDLL). The GAL4 DNA binding domain fused directly to the VP16 activation domain (GD:VP16; SEQ ID NO: 122) served as a positive control for activation. A similar experiment was conducted with another NF-YC protein, G715, SEQ ID NO: 75, and the result was similar to that with G483 (shown in figure). This indicated that the EDLL motif can function in larger complexes, and can confer transcriptional activation function to a plant transcription factor lacking strong activation capacity. It is also active even if the protein is not binding DNA directly (G481:EDLL alone can not bind DNA; data not shown) but is recruited to the DNA via interaction with another DNA binding protein (GD:G483 or GD:G715).

Figure 5:
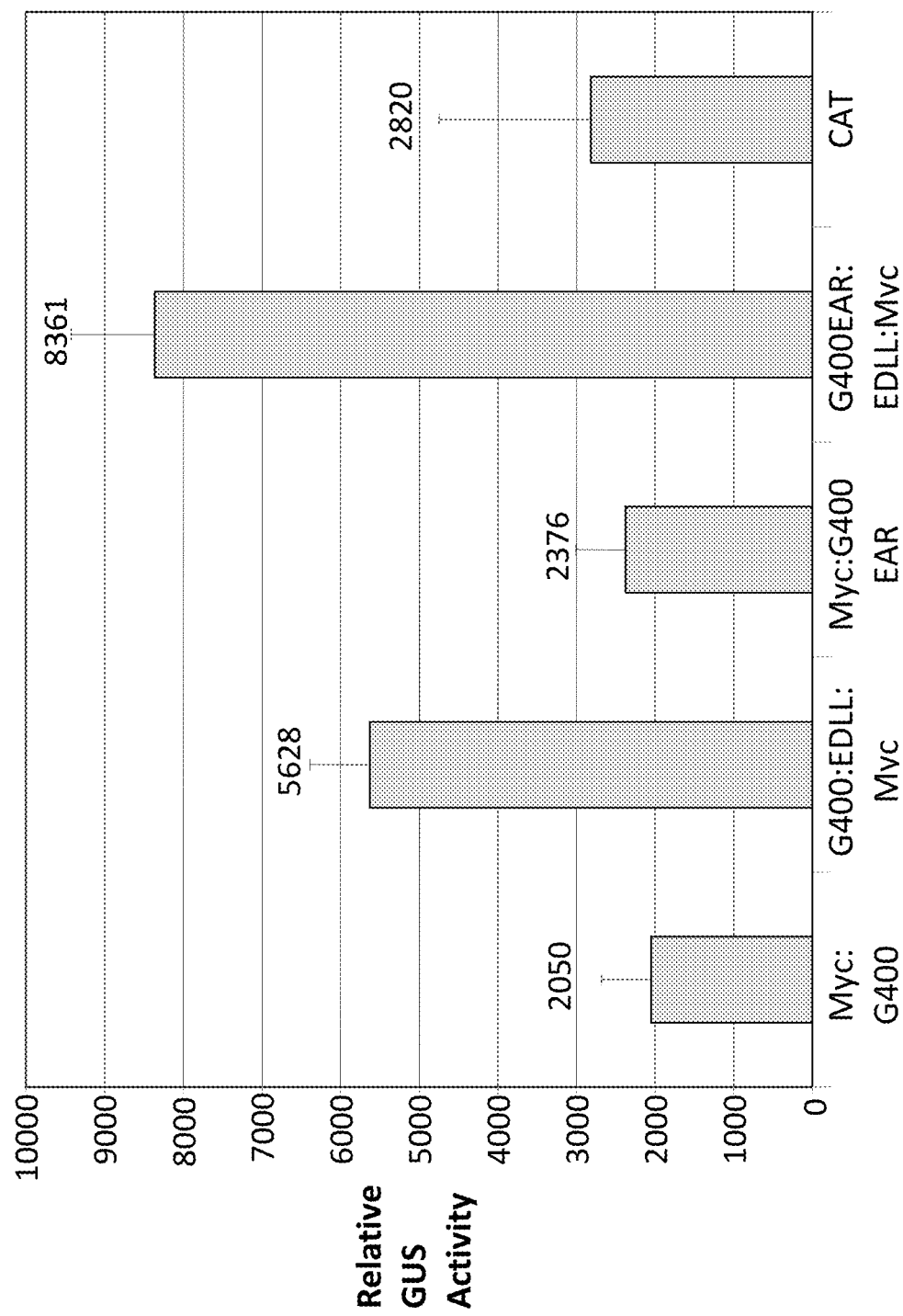

FIG. 5 demonstrates that addition of the EDLL domain to a transcriptional repressor can convert it to a transcriptional activator. G400 (SEQ ID NO: 116) is a homeodomain-leucine zipper (HD-Zip) transcription factor that contains a repression domain termed an EAR domain (Ciarbelli et al. (2008) *Plant Mol Biol.* 68: 465-478). This protein binds to the promoter of another HD-Zip gene (prG398; SEQ ID NO:

99), but does not activate transcription (Myc:G400; encoded by SEQ ID NO: 128) relative to a non-specific control construct (CAT). Addition of the EDLL domain to this transcription factor (G400:EDLL:Myc; encoded by SEQ ID NO: 97) produced significant activation of prG398:GUS fusion construct (SEQ ID NO: 99:GUS), even though the native repression domain was still present. Addition of the EDLL domain to a variant of G400 with the EAR domain mutated (G400EAR:EDLL:Myc; encoded by SEQ ID NO: 98) produced greater activation of the reporter fusion. These results demonstrate that addition of the EDLL domain to a transcription factor with transcriptional repression activity can at least partially overcome the effect of the repression domain.

Figure 6:
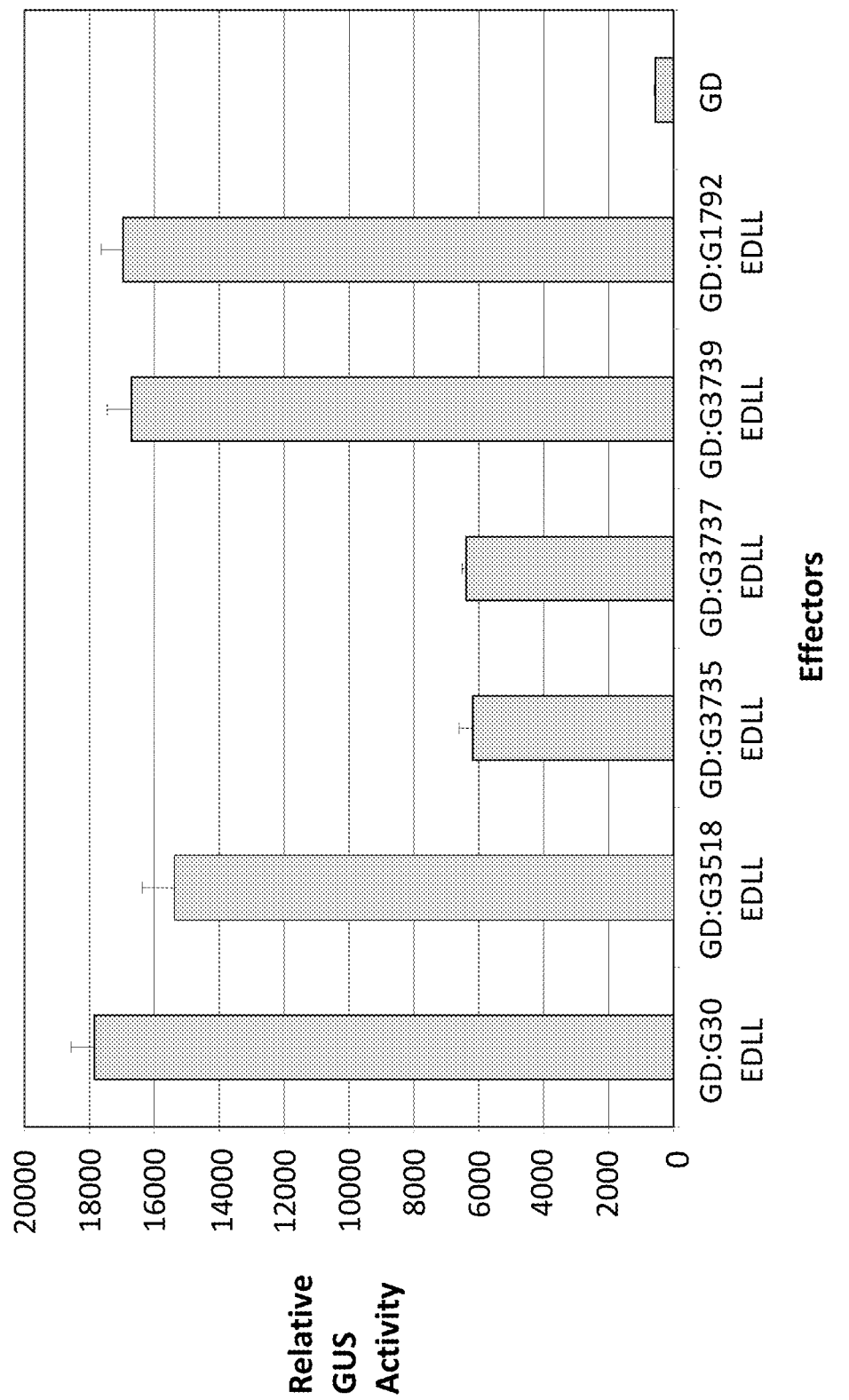

FIG. 6 demonstrates the utility of EDLL domains from other plant species. When fused to the GAL4 DNA binding domain (GD; encoded by SEQ ID NO: 117), EDLL domains from *A. thaliana* (GD:G30EDLL, encoded by SEQ ID NO: 123; GD:G1792EDLL, encoded by SEQ ID NO: 117 fused to SEQ ID NO: 37), soy (GD:G3518EDLL, encoded by SEQ ID NO: 124), *M. truncatula* (GD:G3735EDLL, encoded by SEQ ID NO: 125), rice (GD:G3737EDLL, encoded by SEQ ID NO: 126) and maize (GD:G3739EDLL, encoded by SEQ ID NO: 127) all produced significant transcriptional activation of a chimeric reporter gene containing GAL4 DBD binding sequences in the promoter.

DETAILED DESCRIPTION OF THE INVENTION

The present invention relates to polynucleotides and polypeptides for modifying phenotypes of plants, particularly those associated with increased abiotic stress tolerance, increased biotic stress tolerance and increased yield with respect to a control plant (for example, a wild-type plant, a non-transformed plant, or a plant transformed with an "empty" nucleic acid construct lacking a polynucleotide of interest comprised within a nucleic acid construct introduced into an experimental plant). Throughout this disclosure, various information sources are referred to and/or are specifically incorporated. The information sources include scientific journal articles, patent documents, textbooks, and World Wide Web browser-inactive page addresses. While the reference to these information sources clearly indicates that they can be used by one of skill in the art, each and every one of the information sources cited herein are specifically incorporated in their entirety, whether or not a specific mention of "incorporation by reference" is noted. The contents and teachings of each and every one of the information sources can be relied on and used to make and use embodiments of the invention.

As used herein and in the appended claims, the singular forms "a", "an", and "the" include the plural reference unless the context clearly dictates otherwise. Thus, for example, a reference to "a host cell" includes a plurality of such host cells, and a reference to "a stress" is a reference to one or more stresses and equivalents thereof known to those skilled in the art, and so forth.

Definitions

"Polynucleotide" is a nucleic acid molecule comprising a plurality of polymerized nucleotides, for example, at least about 15 consecutive polymerized nucleotides. A polynucleotide may be a nucleic acid, oligonucleotide, nucleotide, or any fragment thereof. In many instances, a polynucleotide comprises a nucleotide sequence encoding a polypeptide (or protein) or a domain or fragment thereof. Additionally, the polynucleotide may comprise a promoter, an intron, an enhancer region, a polyadenylation site, a translation initiation site, 5' or 3' untranslated regions, a reporter gene, a selectable marker, or the like. The polynucleotide can be single-stranded or double-stranded DNA or RNA. The polynucleotide optionally comprises modified bases or a modified backbone. The polynucleotide can be, for example, genomic DNA or RNA, a transcript (such as an mRNA), a cDNA, a PCR product, a cloned DNA, a synthetic DNA or RNA, or the like. The polynucleotide can be combined with carbohydrate, lipids, protein, or other materials to perform a particular activity such as transformation or form a useful composition such as a peptide nucleic acid (PNA). The polynucleotide can comprise a sequence in either sense or antisense orientations. "Oligonucleotide" is substantially equivalent to the terms amplimer, primer, oligomer, element, target, and probe and is preferably single-stranded.

A "recombinant polynucleotide" is a polynucleotide that is not in its native state, for example, the polynucleotide comprises a nucleotide sequence not found in nature, or the polynucleotide is in a context other than that in which it is naturally found, for example, separated from nucleotide sequences with which it typically is in proximity in nature, or adjacent (or contiguous with) nucleotide sequences with which it typically is not in proximity. For example, the sequence at issue can be cloned into a nucleic acid construct, or otherwise recombined with one or more additional nucleic acids.

An "isolated polynucleotide" is a polynucleotide, whether naturally occurring or recombinant, that is present outside the cell in which it is typically found in nature, whether purified or not. Optionally, an isolated polynucleotide is subject to one or more enrichment or purification procedures, for example, cell lysis, extraction, centrifugation, precipitation, or the like.

"Gene" or "gene sequence" refers to the partial or complete coding sequence of a gene, its complement, and its 5' or 3' untranslated regions. A gene is also a functional unit of inheritance, and in physical terms is a particular segment or sequence of nucleotides along a molecule of DNA (or RNA, in the case of RNA viruses) involved in producing a polypeptide chain. The latter may be subjected to subsequent processing such as chemical modification or folding to obtain a functional protein or polypeptide. A gene may be isolated, partially isolated, or found with an organism's genome. By way of example, a transcription factor gene encodes a transcription factor polypeptide, which may be functional or require processing to function as an initiator of transcription.

Operationally, genes may be defined by the cis-trans test, a genetic test that determines whether two mutations occur in the same gene and that may be used to determine the limits of the genetically active unit (Rieger et al. (1976) *Glossary of Genetics and Cytogenetics: Classical and Molecular*, 4th ed., Springer Verlag, Berlin). A gene generally includes regions preceding ("leaders"; upstream) and following ("trailers"; downstream) the coding region. A gene may also include intervening, non-coding sequences, referred to as "introns", located between individual coding segments, referred to as "exons". Most genes have an associated promoter region, a regulatory sequence 5' of the transcription initiation codon (there are some genes that do not have an identifiable promoter). The function of a gene may also be regulated by enhancers, operators, and other regulatory elements.

The terms "chimeric", "fusion" and "composite" are used to denote a protein, peptide domain or nucleotide sequence or molecule containing at least two component portions which are mutually heterologous in the sense that they are not, otherwise, found directly (covalently) linked in nature. That is, the component portions are not found in the same continuous polypeptide or gene in nature, at least not in the same copy number, order, configuration or orientation or with the same spacing present in the chimeric protein or composite domain. Specifically, the chimeric polypeptides comprised herein each comprise a transcription regulatory protein and a transcription activation domain that are derived from different sources, or may be present in a different copy number, or may be present in a different configuration, than is found in nature.

Such materials contain components derived from at least two different proteins or genes or from at least two non-adjacent portions of the same protein or gene. Composite proteins, and DNA sequences which encode them, are recombinant in the sense that they contain at least two constituent portions which are not otherwise found directly linked (covalently) together in nature.

"Heterologous" with respect to polynucleotide or polypeptide sequences refers to sequences that are of different origins, such as, for example, from different organisms, different genes or proteins, different regions of a chromosome, different chromosomes, or different transcription regulating regions. For example, a chimeric protein comprising two subsequences, where the subsequences are not associated with each other in nature, or operatively linked to each other in nature, constitutes a protein with mutually heterologous components. A specific example may include, but would not be limited to, a transcriptional activation domain from one protein fused to a transcription factor sequence from another protein, where the two are not associated with each other in nature; in this case, the transcriptional activation domain and the transcription factor sequence are mutually heterologous.

A "polypeptide" is an amino acid sequence comprising a plurality of consecutive polymerized amino acid residues for example, at least about 15 consecutive polymerized amino acid residues. In many instances, a polypeptide comprises a polymerized amino acid residue sequence that is a transcription factor or a domain or portion or fragment thereof. Additionally, the polypeptide may comprise: (i) a nuclear localization domain; (ii) an activation domain; (iii) a repression domain; (iv) an oligomerization domain; (v) a protein-protein interaction domain; (vi) a DNA-binding domain; or the like. The polypeptide optionally comprises modified amino acid residues, naturally occurring amino acid residues not encoded by a codon, non-naturally occurring amino acid residues.

"Protein" refers to an amino acid sequence, oligopeptide, peptide, polypeptide or portions thereof whether naturally occurring or synthetic.

"Portion", as used herein, refers to any part of a protein used for any purpose, but especially for the screening of a library of molecules which specifically bind to that portion or for the production of antibodies.

A "recombinant polypeptide" is a polypeptide produced by translation of a recombinant polynucleotide. A "synthetic polypeptide" is a polypeptide created by consecutive polymerization of isolated amino acid residues using methods well known in the art. An "isolated polypeptide," whether a naturally occurring or a recombinant polypeptide, is more enriched in (or out of) a cell than the polypeptide in its natural state in a wild-type cell, for example, more than about 5% enriched, more than about 10% enriched, or more than about 20%, or more than about 50%, or more, enriched, that is, alternatively denoted: 105%, 110%, 120%, 150% or more, enriched relative to wild type standardized at 100%. Such an enrichment is not the result of a natural response of a wild-type plant. Alternatively, or additionally, the isolated polypeptide is separated from other cellular components with which it is typically associated, for example, by any of the various protein purification methods herein.

"Homology" refers to sequence similarity between a reference sequence and at least a fragment of a newly sequenced clone insert or its encoded amino acid sequence.

"Identity" or "similarity" refers to sequence similarity between two polynucleotide sequences or between two polypeptide sequences, with identity being a more strict comparison. The phrases "percent identity" and "% identity" refer to the percentage of sequence identity found in a comparison of two or more polynucleotide sequences or two or more polypeptide sequences. "Sequence similarity" refers to the percent similarity in base pair sequence (as determined by any suitable method) between two or more polynucleotide sequences. Two or more sequences can be anywhere from 0-100% similar, or any integer value therebetween. Identity or similarity can be determined by comparing a position in each sequence that may be aligned for purposes of comparison. When a position in the compared sequence is occupied by the same nucleotide base or amino acid, then the molecules are identical at that position. A degree of similarity or identity between polynucleotide sequences is a function of the number of identical, matching or corresponding nucleotides at positions shared by the polynucleotide sequences. A degree of identity of polypeptide sequences is a function of the number of identical amino acids at corresponding positions shared by the polypeptide sequences. A degree of homology or similarity of polypeptide sequences is a function of the number of amino acids at corresponding positions shared by the polypeptide sequences.

"Alignment" refers to a number of nucleotide bases or amino acid residue sequences aligned by lengthwise comparison so that components in common (that is, nucleotide bases or amino acid residues at corresponding positions) may be visually and readily identified. The fraction or percentage of components in common is related to the homology or identity between the sequences. Alignments such as those of FIG. 1 may be used to identify conserved domains and relatedness within these domains. An alignment may suitably be determined by means of computer programs known in the art, such as MACVECTOR software (1999) (Accelrys, Inc., San Diego, Calif.).

A "conserved domain" or "conserved region" as used herein refers to a region within heterogeneous polynucleotide or polypeptide sequences where there is a relatively high degree of sequence identity or homology between the distinct sequences. With respect to polynucleotides encoding presently disclosed polypeptides, a conserved domain is preferably at least nine base pairs (bp) in length. Transcription factor sequences that possess or encode for conserved domains that have a minimum percentage identity and have comparable biological activity to the present polypeptide sequences, thus being members of the same clade of transcription factor polypeptides, are encompassed by the invention. Reduced or eliminated expression of a polypeptide that comprises, for example, a conserved domain having DNA-binding, activation or nuclear localization activity, results in the transformed plant having similar improved traits as other transformed plants having reduced or eliminated expression of other members of the same clade of transcription factor polypeptides.

A fragment or domain can be referred to as outside a conserved domain, outside a consensus sequence, or outside a consensus DNA-binding site that is known to exist or that exists for a particular polypeptide class, family, or sub-family. In this case, the fragment or domain will not include the exact amino acids of a consensus sequence or consensus DNA-binding site of a transcription factor class, family or sub-family, or the exact amino acids of a particular transcription factor consensus sequence or consensus DNA-binding site. Furthermore, a particular fragment, region, or domain of a polypeptide, or a polynucleotide encoding a polypeptide, can be "outside a conserved domain" if all the amino acids of the fragment, region, or domain fall outside of a defined conserved domain(s) for a polypeptide or protein. Sequences having lesser degrees of identity but comparable biological activity are considered to be equivalents.

As one of ordinary skill in the art recognizes, conserved domains may be identified as regions or domains of identity to a specific consensus sequence (see, for example, Riechmann et al. (2000) *Science* 290, 2105-2110; and Riechmann and Ratcliffe (2000) *Curr. Opin. Plant Biol.* 3, 423-434). Thus, by using alignment methods well known in the art, the conserved domains of the plant polypeptides may be determined.

The conserved domains for many of the polypeptide sequences of the invention are listed in Table 1. Also, the polypeptides of Table 1 have conserved domains specifically indicated by amino acid coordinate start and stop sites. A comparison of the regions of these polypeptides allows one of skill in the art (see, for example, Reeves and Nissen, 1995, to identify domains or conserved domains for any of the polypeptides listed or referred to in this disclosure.

"Complementary" refers to the natural hydrogen bonding by base pairing between purines and pyrimidines. For example, the sequence A-C-G-T (5'→3') forms hydrogen bonds with its complements A-C-G-T (5'→3') or A-C-G-U (5'→3'). Two single-stranded molecules may be considered partially complementary, if only some of the nucleotides bond, or "completely complementary" if all of the nucleotides bond. The degree of complementarity between nucleic acid strands affects the efficiency and strength of hybridization and amplification reactions. "Fully complementary" refers to the case where bonding occurs between every base pair and its complement in a pair of sequences, and the two sequences have the same number of nucleotides.

The terms "paralog" and "ortholog" are defined below in the section entitled "Orthologs and Paralogs". In brief, orthologs and paralogs are evolutionarily related genes that have similar sequences and functions. Orthologs are structurally related genes in different species that are derived by a speciation event. Paralogs are structurally related genes within a single species that are derived by a duplication event.

The term "equivalog" describes members of a set of homologous proteins that are conserved with respect to function since their last common ancestor. Related proteins are grouped into equivalog families, and otherwise into protein families with other hierarchically defined homology types. This definition is provided at the Institute for Genomic Research (TIGR) World Wide Web (www) website, "tigr.org" under the heading "Terms associated with TIGRFAMs".

In general, the term "variant" refers to molecules with some differences, generated synthetically or naturally, in their base or amino acid sequences as compared to a reference (native) polynucleotide or polypeptide, respectively. These differences include substitutions, insertions, deletions or any desired combinations of such changes in a native polynucleotide of amino acid sequence.

With regard to polynucleotide variants, differences between presently disclosed polynucleotides and polynucleotide variants are limited so that the nucleotide sequences of the former and the latter are closely similar overall and, in many regions, identical. Due to the degeneracy of the genetic code, differences between the former and latter nucleotide sequences may be silent (that is, the amino acids encoded by the polynucleotide are the same, and the variant polynucleotide sequence encodes the same amino acid sequence as the presently disclosed polynucleotide. Variant nucleotide sequences may encode different amino acid sequences, in which case such nucleotide differences will result in amino acid substitutions, additions, deletions, insertions, truncations or fusions with respect to the similar disclosed polynucleotide sequences. These variations may result in polynucleotide variants encoding polypeptides that share at least one functional characteristic. The degeneracy of the genetic code also dictates that many different variant polynucleotides can encode identical and/or substantially similar polypeptides in addition to those sequences illustrated in the Sequence Listing.

Also within the scope of the invention is a variant of a nucleic acid listed in the Sequence Listing, that is, one having a sequence that differs from the one of the polynucleotide sequences in the Sequence Listing, or a complementary sequence, that encodes a functionally equivalent polypeptide (that is, a polypeptide having some degree of equivalent or similar biological activity) but differs in sequence from the sequence in the Sequence Listing, due to degeneracy in the genetic code. Included within this definition are polymorphisms that may or may not be readily detectable using a particular oligonucleotide probe of the polynucleotide encoding polypeptide, and improper or unexpected hybridization to allelic variants, with a locus other than the normal chromosomal locus for the polynucleotide sequence encoding polypeptide.

"Allelic variant" or "polynucleotide allelic variant" refers to any of two or more alternative forms of a gene occupying the same chromosomal locus. Allelic variation arises naturally through mutation, and may result in phenotypic polymorphism within populations. Gene mutations may be "silent" or may encode polypeptides having altered amino acid sequences. "Allelic variant" and "polypeptide allelic variant" may also be used with respect to polypeptides, and in this case, the terms refer to a polypeptide encoded by an allelic variant of a gene.

"Splice variant" or "polynucleotide splice variant" as used herein refers to alternative forms of RNA transcribed from a gene. Splice variation naturally occurs as a result of alternative sites being spliced within a single transcribed RNA molecule or between separately transcribed RNA molecules, and may result in several different forms of mRNA transcribed from the same gene. Thus, splice variants may encode polypeptides having different amino acid sequences, which may or may not have similar functions in the organism. "Splice variant" or "polypeptide splice variant" may also refer to a polypeptide encoded by a splice variant of a transcribed mRNA.

As used herein, "polynucleotide variants" may also refer to polynucleotide sequences that encode paralogs and orthologs of the presently disclosed polypeptide sequences. "Polypeptide variants" may refer to polypeptide sequences that are paralogs and orthologs of the presently disclosed polypeptide sequences.

Differences between presently disclosed polypeptides and polypeptide variants are limited so that the sequences of the former and the latter are closely similar overall and, in many regions, identical. Presently disclosed polypeptide sequences and similar polypeptide variants may differ in amino acid sequence by one or more substitutions, additions, deletions, fusions and truncations, which may be present in any combination. These differences may produce silent changes and result in functionally equivalent polypeptides. Thus, it will be readily appreciated by those of skill in the art, that any of a variety of polynucleotide sequences is capable of encoding the polypeptides and homolog polypeptides of the invention. A polypeptide sequence variant may have "conservative" changes, wherein a substituted amino acid has similar structural or chemical properties. Deliberate amino acid substitutions may thus be made on the basis of similarity in polarity, charge, solubility, hydrophobicity, hydrophilicity, and/or the amphipathic nature of the residues, as long as a significant amount of the functional or biological activity of the polypeptide is retained. For example, negatively charged amino acids may include aspartic acid and glutamic acid, positively charged amino acids may include lysine and arginine, and amino acids with uncharged polar head groups having similar hydrophilicity values may include leucine, isoleucine, and valine; glycine and alanine; asparagine and glutamine; serine and threonine; and phenylalanine and tyrosine. More rarely, a variant may have "non-conservative" changes, for example, replacement of a glycine with a tryptophan. Similar minor variations may also include amino acid deletions or insertions, or both. Related polypeptides may comprise, for example, additions and/or deletions of one or more N-linked or O-linked glycosylation sites, or an addition and/or a deletion of one or more cysteine residues. Guidance in determining which and how many amino acid residues may be substituted, inserted or deleted without abolishing functional or biological activity may be found using computer programs well known in the art, for example, DNASTAR software (see U.S. Pat. No. 5,840,544).

"Fragment", with respect to a polynucleotide, refers to a clone or any part of a polynucleotide molecule that retains a usable, functional characteristic. Useful fragments include oligonucleotides and polynucleotides that may be used in hybridization or amplification technologies or in the regulation of replication, transcription or translation. A "polynucleotide fragment" refers to any subsequence of a polynucleotide, typically, of at least about 9 consecutive nucleotides, preferably at least about 30 nucleotides, more preferably at least about 50 nucleotides, of any of the sequences provided herein. Exemplary polynucleotide fragments are the first sixty consecutive nucleotides of the polynucleotides listed in the Sequence Listing. Exemplary fragments also include fragments that comprise a region that encodes an conserved domain of a polypeptide. Exemplary fragments also include fragments that comprise a conserved domain of a polypeptide.

Fragments may also include subsequences of polypeptides and protein molecules, or a subsequence of the polypeptide. Fragments may have uses in that they may have antigenic potential. In some cases, the fragment or domain is a subsequence of the polypeptide which performs at least one biological function of the intact polypeptide in substantially the same manner, or to a similar extent, as does the intact polypeptide. For example, a polypeptide fragment can comprise a recognizable structural motif or functional domain such as a DNA-binding site or domain that binds to a DNA promoter region, an activation domain, or a domain for protein-protein interactions, and may initiate transcription. Fragments can vary in size from as few as 3 amino acid residues to the full length of the intact polypeptide, but are preferably at least about 30 amino acid residues in length and more preferably at least about 60 amino acid residues in length.

The invention also encompasses production of DNA sequences that encode polypeptides and derivatives, or fragments thereof, entirely by synthetic chemistry. After production, the synthetic sequence may be inserted into any of the many available nucleic acid constructs and cell systems using reagents well known in the art. Moreover, synthetic chemistry may be used to introduce mutations into a sequence encoding polypeptides or any fragment thereof.

The term "plant" includes whole plants, shoot vegetative organs/structures (for example, leaves, stems, rhizomes, and tubers), roots, flowers and floral organs/structures (for example, bracts, sepals, petals, stamens, carpels, anthers and ovules), seed (including embryo, endosperm, and seed coat) and fruit (the mature ovary), plant tissue (for example, vascular tissue, ground tissue, and the like), calli, protoplasts, and cells (for example, guard cells, egg cells, and the like), and progeny of same. The class of plants that can be used in the method of the invention is generally as broad as the class of higher and lower plants amenable to transformation techniques, including angiosperms (monocotyledonous and dicotyledonous plants), gymnosperms, ferns, horsetails, psilophytes, lycophytes, bryophytes, multicellular algae, and unicellular algae.

A "control plant" as used in the present invention refers to a plant cell, seed, plant component, plant tissue, plant organ or whole plant used to compare against transformed, transgenic or genetically modified plant for the purpose of identifying an enhanced phenotype in the transformed, transgenic or genetically modified plant. A control plant may in some cases be a transformed or transgenic plant line that comprises an empty nucleic acid construct or marker gene, but does not contain the recombinant polynucleotide of the present invention that is expressed in the transformed, transgenic or genetically modified plant being evaluated. In general, a control plant is a plant of the same line or variety as the transformed, transgenic or genetically modified plant being tested. A suitable control plant would include a genetically unaltered or non-transgenic plant of the parental line used to generate a transformed or transgenic plant herein.

"Wild type" or "wild-type", as used herein, refers to a plant cell, seed, plant component, plant tissue, plant organ or whole plant that has not been genetically modified or treated in an experimental sense. Wild-type cells, seed, components, tissue, organs or whole plants may be used as controls to compare levels of expression and the extent and nature of trait modification with cells, tissue or plants of the same species in which a polypeptide's expression is altered, for example, in that it has been knocked out, overexpressed, or ectopically expressed.

"Transformation" refers to the transfer of a foreign polynucleotide sequence into the genome of a host organism such as that of a plant or plant cell, or introduction of a foreign polynucleotide sequence into plant or plant cell such that is expressed and results in production of protein. Typically, the foreign genetic material has been introduced into the plant by human manipulation, but any method can be used as one of skill in the art recognizes. Examples of methods of plant transformation include *Agrobacterium*-mediated transformation (De Blaere et. al. (1987) "Vectors for Cloning in Plant Cells", *Meth. Enzymol.*, vol. 153:277-292) and biolistic methodology (U.S. Pat. No. 4,945,050 to Klein et al.).

A "transformed plant", which may also be referred to as a "transgenic plant" or "transformant", generally refers to a plant, a plant cell, plant tissue, seed or calli that has been through, or is derived from a plant cell that has been through, a stable or transient transformation process in which a "nucleic acid construct" that contains at least one exogenous polynucleotide sequence is introduced into the plant. The "nucleic acid construct" contains genetic material that is not found in a wild-type plant of the same species, variety or cultivar, or may contain extra copies of a native sequence under the control of its native promoter. The genetic material may include a regulatory element, a transgene (for example, a transcription factor sequence), a transgene overexpressing a protein of interest, an insertional mutagenesis event (such as by transposon or T-DNA insertional mutagenesis), an activation tagging sequence, a mutated sequence, an antisense transgene sequence, a construct containing inverted repeat sequences derived from a gene of interest to induce RNA interference, or a nucleic acid sequence designed to produce a homologous recombination event or DNA-repair based change, or a sequence modified by chimeraplasty. In some embodiments the regulatory and transcription factor sequence may be derived from the host plant, but by their incorporation into a nucleic acid construct, represent an arrangement of the polynucleotide sequences not found in a wild-type plant of the same species, variety or cultivar.

An "untransformed plant" is a plant that has not been through the transformation process.

A "stably transformed" plant, plant cell or plant tissue has generally been selected and regenerated on a selection media following transformation.

A "nucleic acid construct" may comprise a polypeptide-encoding sequence operably linked (that is, under regulatory control of) to appropriate inducible, tissue-specific, developmental, or constitutive regulatory sequences that allow for the controlled expression of polypeptide. The expression vector or cassette can be introduced into a plant by transformation or by breeding after transformation of a parent plant. A plant refers to a whole plant as well as to a plant part, such as seed, fruit, leaf, or root, plant tissue, plant cells or any other plant material, for example, a plant explant, to produce a recombinant plant (for example, a recombinant plant cell comprising the nucleic acid construct) as well as to progeny thereof, and to in vitro systems that mimic biochemical or cellular components or processes in a cell.

A "trait" refers to a physiological, morphological, biochemical, or physical characteristic of a plant or particular plant material or cell. In some instances, this characteristic is visible to the human eye, such as seed or plant size, or can be measured by biochemical techniques, such as detecting the protein, starch, or oil content of seed or leaves, or by observation of a metabolic or physiological process, for example, by measuring tolerance to water deprivation or particular salt or sugar concentrations, or by the observation of the expression level of a gene or genes, for example, by employing Northern analysis, RT-PCR, microarray gene expression assays, or reporter gene expression systems, or by agricultural observations such as hyperosmotic stress tolerance, disease resistance, growth rate, or yield. Any technique can be used to measure the amount of, comparative level of, or difference in any selected chemical compound or macromolecule in the transformed or transgenic plants, however.

"Trait modification" refers to a detectable difference in a characteristic in a plant with reduced or eliminated expression, or ectopic expression, of a polynucleotide or polypeptide of the present invention relative to a plant not doing so, such as a wild-type plant. In some cases, the trait modification can be evaluated quantitatively. For example, the trait modification can entail at least about a 2% increase or decrease, or an even greater difference, in an observed trait as compared with a control or wild-type plant. It is known that there can be a natural variation in the modified trait. Therefore, the trait modification observed entails a change of the normal distribution and magnitude of the trait in the plants as compared to control or wild-type plants.

When two or more plants have "similar morphologies", "substantially similar morphologies", "a morphology that is substantially similar", or are "morphologically similar", the plants have comparable forms or appearances, including analogous features such as overall dimensions, height, width, mass, root mass, shape, glossiness, color, stem diameter, leaf size, leaf dimension, leaf density, internode distance, branching, root branching, number and form of inflorescences, and other macroscopic characteristics, and the individual plants are not readily distinguishable based on morphological characteristics alone.

"Modulates" refers to a change in activity (biological, chemical, or immunological) or lifespan resulting from specific binding between a molecule and either a nucleic acid molecule or a protein.

"Ectopic expression or altered expression" in reference to a polynucleotide indicates that the pattern of expression in, for example, a transformed or transgenic plant or plant tissue, is different from the expression pattern in a wild-type plant or a reference plant of the same species. The pattern of expression may also be compared with a reference expression pattern in a wild-type plant of the same species. For example, the polynucleotide or polypeptide is expressed in a cell or tissue type other than a cell or tissue type in which the sequence is expressed in the wild-type plant, or by expression at a time other than at the time the sequence is expressed in the wild-type plant, or by a response to different inducible agents, such as hormones or environmental signals, or at different expression levels (either higher or lower) compared with those found in a wild-type plant. The term also refers to altered expression patterns that are produced by lowering the levels of expression to below the detection level or completely abolishing expression. The resulting expression pattern can be transient or stable, constitutive or inducible, tissue specific, or developmentally-regulated (each of these may be controlled by the choice of promoter operably linked to a polynucleotide encoding a polypeptide of the invention). In reference to a polypeptide, the terms "ectopic expression" or "altered expression" further may relate to altered activity levels resulting from the interactions of the polypeptides with exogenous or endogenous modulators or from interactions with factors or as a result of the chemical modification of the polypeptides.

The term "overexpression" as used herein refers to a greater expression level of a gene in a plant, plant cell or plant tissue, compared to expression of that gene in a wild-type plant, cell or tissue, at any developmental or temporal stage. Overexpression can occur when, for example, the genes encoding one or more polypeptides are under the control of a strong promoter (for example, the cauliflower mosaic virus 35S transcription initiation region). Overexpression may also be achieved by placing a gene of interest under the control of an inducible or tissue specific promoter, or may be achieved through integration of transposons or engineered T-DNA molecules into regulatory regions of a target gene. Thus, overexpression may occur throughout a plant, in specific tissues of the plant, or in the presence or absence of particular environmental signals, depending on the promoter or overexpression approach used.

Overexpression may take place in plant cells normally lacking expression of polypeptides functionally equivalent or identical to the present polypeptides. Overexpression may also occur in plant cells where endogenous expression of the present polypeptides or functionally equivalent molecules normally occurs, but such normal expression is at a lower level at the same time of day or at the same developmental stage. Overexpression of a gene thus results in a greater than normal production, or "overproduction" of the encoded RNA and or encoded the polypeptide in the plant, cell or tissue.

The term "transcription regulating region" refers to a DNA regulatory sequence that regulates expression of one or more genes in a plant when a transcription factor having one or more specific binding domains binds to the DNA regulatory sequence. Transcription factors typically possess a conserved DNA binding domain. The transcription factors also comprise an amino acid subsequence that forms a transcription activation domain that regulates expression of one or more target genes, such as genes that confer abiotic stress tolerance, in a plant when the transcription factor binds to the regulating region.

DESCRIPTION OF THE SPECIFIC EMBODIMENTS

The data presented herein represent the results obtained in experiments with polynucleotides and polypeptides that may be expressed in plants for the purpose of increasing yield, or reducing yield losses that arise from abiotic stresses.

The isolation and functional characterization of a small region comprising consecutive amino acids from Ethylene Response Factor 98 (AtERF98, SEQ ID NO: 2) of the flowering plant *Arabidopsis* is described herein. This small peptide contains many acidic and polar amino acids residue interspersed around hydrophobic leucines. This peptide was designated as the "EDLL motif", based on four conserved glutamic acid, aspartic acid, leucine and leucine residues in corresponding positions (FIG. 1), and as arranged in the consensus sequence $EX_4DX_3LX_3L$ (SEQ ID NO: 55), where X is any amino acid. The EDLL domain may also be characterized by the consensus sequence E-L/F-$X_2$-L/F-D-D/N-$X_2$-L-$X_2$-L/M-L (SEQ ID NO: 56), or the consensus sequence E-F/L-X-X-L/F-D-D/N-X-V/L/I-L-X-X-L/M-L (SEQ ID NO: 94), or the consensus sequence E-F/L-E/V-Y/C/F-L/F-D-D/N-X-V/L-L-E/Q/D-E/D/S-L/M-L (SEQ ID NO: 95), where X is any amino acid. Some experimental evidence has been obtained with sequences lacking the glutamic acid residue at the first position, in which the sequences retained some transcriptional activation potential. This modification may represent a means to fine-tune the activation potential of a particular EDLL sequence, which may be useful when a greater or lesser degree of activity of a transcription regulatory polypeptide to which the EDLL domain is fused is desirable.

The EDLL motif is conserved in diverse plant genera including, but not limited to, eudicots including *Arabidopsis, Glycine*, and *Medicago* and monocots *Oryza, Triticum,* and *Zea* (Table 1 and FIG. 1).

TABLE 1

| | Gene families and conserved EDLL domains of AtERF98 clade members | | | | |
|---|---|---|---|---|---|
| SEQ ID NO: | GID No./ Species | EDLL Domains in AA Coordinates | EDLL Domain | SEQ ID NO: of EDLL domain | Identical residues (% ID to G1792 EDLL Domain) |
| 2 | AtERF98 (G1792)/At | 117-132 | VFEFEYLDDKVLEELL | 37 | 16/16 (100%) |
| 4 | G1795/At | 104-119 | VFEFEYLDDSVLEELL | 38 | 15/16 (93.8%) |
| 6 | G30/At | 100-115 | VFEFEYLDDSVLDELL | 39 | 14/16 (87.5%) |
| 8 | G1791/At | 108-123 | VIEFEYLDDSLLEELL | 40 | 13/16 (81.2%) |
| 10 | G3520/Gm | 109-124 | VIEFECLDDKLLEDLL | 41 | 12/16 (75.0%) |
| 12 | G3519/Gm | 128-143 | TFELEYLDNKLLEELL | 42 | 12/16 (75.0%) |
| 14 | G3383/Os | 101-116 | KIEFEYLDDKVLDDLL | 43 | 12/16 (75.0%) |
| 16 | G3517/Zm | 103-118 | VIEFEYLDDEVLQEML | 44 | 12/16 (75.0%) |
| 18 | G3518/Gm | 135-150 | TFELEYFDNKLLEELL | 45 | 11/16 (68.7%) |
| 20 | G3739/Zm | 107-122 | VIELEYLDDEVLQEML | 46 | 11/16 (68.7%) |
| 22 | G3736/Ta | 108-123 | VIEFEYLDDDVLQSML | 47 | 11/16 (68.7%) |
| 24 | G3381/Os | 109-124 | PIEFEYLDDHVLQEML | 48 | 11/16 (68.7%) |
| 26 | G3737/Os | 101-116 | KVELVYLDDKVLDELL | 49 | 11/16 (68.7%) |
| 28 | G3515/Os | 116-131 | KVELECLDDKVLEDLL | 50 | 11/16 (68.7%) |
| 30 | G3516/Zm | 107-122 | KVELECLDDRVLEELL | 51 | 11/16 (68.7%) |
| 32 | G3380/Os | 103-118 | VIELECLDDQVLQEML | 52 | 10/16 (62.5%) |

TABLE 1 -continued

Gene families and conserved EDLL domains of AtERF98 clade members

| SEQ ID NO: | GID No./ Species | EDLL Domains in AA Coordinates | EDLL Domain | SEQ ID NO: of EDLL domain | Identical residues (% ID to G1792 EDLL Domain) |
|---|---|---|---|---|---|
| 34 | G3794/Zm | 102-117 | VIELECLDDQVLQEML | 53 | 10/16 (62.5%) |
| 36 | G3735/Mt | 131-144 | ELEFLDNKLLQELL | 54 | 9/16 (56.2%) |

Abbreviations for Table 1:
At - *Arabidopsis thaliana*;
Gm - *Glycine max*;
Mt - *Medicago truncatula*;
Os - *Oryza sativa*;
Ta - *Triticum aestivum*;
Zm - *Zea mays*

By performing a similar analysis starting with each of the EDLL domains in Table 1, the percentage identities of the closest homologs, and the proportion of identical residues (in parentheses), in decreasing order of identity to the following EDLL domains, are, for the:

G1795 EDLL domain, SEQ ID NO: 38, the following share identical residues of:
93.8% (15/16)—AtERF98, G30;
87.5% (14/16)—G1791;
75.0% (12/16)—G3517;
68.7% (11/16)—G3736, G3383, G3381, G3739, G3519, G3520, G3516;
62.5% (10/16)—G3518, G3794, G3737, G3380, G3515; and
50.0% (8/16)—G3735;

G30 EDLL domain, SEQ ID NO: 39, the following share identical residues of:
93.8% (15/16)—G1795;
87.5% (14/16)—G1792;
81.2% (13/16)—G1791;
75.0% (12/16)—G3383, G3517;
68.7% (11/16)—G3736, G3381, G3739, G3737;
62.5% (10/16)—G3519, G3520, G3794, G3380, G3516;
56.2% (9/16)—G3518, G3515; and
50.0% (8/16)—G3735;

G1791 EDLL domain, SEQ ID NO: 40, the following share identical residues of:
87.5% (14/16)—G1795;
81.2% (13/16)—G30, AtERF98, G3520;
75.0% (12/16)—G3517;
68.7% (11/16)—G3736, G3383, G3381, G3739, G3519;
62.5% (10/16)—G3794, G3518, G3380, G3516;
56.2% (9/16)—G3737, G3735, G3515; and
50.0%—(8/16);

G3520 EDLL domain, SEQ ID NO: 41, the following share identical residues of:
81.2% (13/16)—G1791;
75.0% (12/16)—AtERF98, G3515, G3383;
68.7% (11/16)—G1795;
62.5% (10/16)—G30, G3516, G3794, G3380, G3517, G3736, G3519; and
56.2% (9/16)—G3739, G3381, G3735, G3518, G3737;

G3519 EDLL domain, SEQ ID NO: 42, the following share identical residues of:
93.8% (15/16)—G3518;
75.0% (12/16)—AtERF98, G3735;
68.7% (11/16)—G1795, G1791;
62.5% (10/16)—G30, G3737, G3516, G3515, G3520;
56.2% (9/16)—G3739, G3383;
50.0% (8/16)—G3517, G3381, G3794, G3380; and
43.7% (7/16)—G3736;

G3383 EDLL domain, SEQ ID NO: 43, the following share identical residues of:
75.0% (12/16)—AtERF98, G30, G3737, G3515, G3520;
68.7% (11/16)—G1791, G1795, G3381, G3517, G3736;
62.5% (10/16)—G3516, G3739;
56.2% (9/16)—G3380, G3794, G3519; and
50.0% (8/16)—G3518, G3735;

G3517 EDLL domain, SEQ ID NO: 44, the following share identical residues of:
93.8% (15/16)—G3739;
87.5% (14/16)—G3736, G3381;
81.2% (13/16)—G3380, G3794;
75.0% (12/16)—AtERF98, G30, G1791, G1795;
68.7% (11/16)—G3383;
62.5% (10/16)—G3520;
56.2% (9/16)—G3737, G3516;
50.0% (8/16)—G3735, G3515, G3519; and
43.7% (7/16)—G3518;

G3517 EDLL domain, SEQ ID NO: 45, the following share identical residues of:
93.8% (15/16)—G3519;
68.7% (11/16)—AtERF98, G3735;
62.5% (10/16)—G1791, G1795;
56.2% (9/16)—G30, G3515, G3516, G3520, G3737;
50.0% (8/16)—G3383, G3739;
43.7% (7/16)—G3380, G3381, G3517, G3794; and
37.5% (6/16)—G3736;

G3739 EDLL domain, SEQ ID NO: 46, the following share identical residues of:
93.8% (15/16)—G3517;
87.5% (14/16)—G3380, G3794;
81.2% (13/16)—G3381, G3736;
68.7% (11/16)—AtERF98, G30, G1791, G1795;
62.5% (10/16)—G3383, G3737, G3516;
56.2% (9/16)—G3515, G3519, G3520, G3735; and
50.0% (8/16)—G3518;

G3739 EDLL domain, SEQ ID NO: 47, the following share identical residues of:
87.5% (14/16)—G3517;
81.2% (13/16)—G3381, G3739;
75.0% (12/16)—G3380, G3794;
68.7% (11/16)—AtERF98, G30, G1791, G1795, G3383;
62.5% (10/16)—G3520;
50.0% (8/16)—G3515, G3516; G3737;
43.7% (7/16)—G3519, G3735;
37.5% (6/16)—G3518;

G3381 EDLL domain, SEQ ID NO: 48, the following share identical residues of:
  87.5% (14/16)—G3517;
  81.2% (13/16)—G3736, G3739;
  75.0% (12/16)—G3380, G3794;
  68.7% (11/16)—AtERF98, G30, G1791, G1795, G3383;
  56.2% (9/16)—G3516, G3520, G3737;
  50.0% (8/16)—G3515, G3519, G3735; and
  43.7% (7/16)—G3518;
G3737 EDLL domain, SEQ ID NO: 49, the following share identical residues of:
  75.0% (12/16)—G3383, G3515, G3516;
  68.7% (11/16)—AtERF98, G30;
  62.5% (10/16)—G1795, G3519, G3739;
  56.2% (9/16)—G1791, G3380, G3381, G3517, G3518, G3735, G3794; and
  50.0% (8/16)—G3520, G3736;
G3515 EDLL domain, SEQ ID NO: 50, the following share identical residues of:
  87.5% (14/16)—G3516;
  75.0% (12/16)—G3383, G3520, G3737;
  68.7% (11/16)—AtERF98;
  62.5% (10/16)—G1795, G3380, G3519, G3794;
  56.2% (9/16)—G30, G1791, G3518, G3735, G3739; and
  50.0% (8/16)—G3381, G3517, G3736;
G3516 EDLL domain, SEQ ID NO: 51, the following share identical residues of:
  87.5% (14/16)—G3515;
  75.0% (12/16)—G3737;
  68.7% (11/16)—AtERF98, G1795, G3380, G3794;
  62.5% (10/16)—G30, G1791, G3383, G3519, G3520, G3739;
  56.2% (9/16)—G3381, G3517, G3518, G3735; and
  50.0% (8/16)—G3736;
G3380 EDLL domain, SEQ ID NO: 52, the following share identical residues of:
  100% (16/16)—G3794;
  87.5% (14/16)—G3739;
  81.2% (13/16)—G3517;
  75.0% (12/16)—G3381, G3736;
  68.7% (11/16)—G3516;
  62.5% (10/16)—AtERF98, G30, G1791, G1795, G3515, G3520;
  56.2% (9/16)—G3383, G3735, G3737;
  50.0% (8/16)—G3519; and
  43.7% (7/16)—G3518;
G3794 EDLL domain, SEQ ID NO: 53, the following share identical residues of:
  100% (16/16)—G3380;
  87.5% (14/16)—G3739;
  81.2% (13/16)—G3517;
  75.0% (12/16)—G3381, G3736;
  68.7% (11/16)—G3516;
  62.5% (10/16)—AtERF98, G30, G1791, G1795, G3515, G3520;
  56.2% (9/16)—G3383, G3735, G3737;
  50.0% (8/16)—G3519; and
  43.7% (7/16)—G3518;
G3735 EDLL domain, SEQ ID NO: 54, the following share identical residues of:
  75.0% (12/16)—G3519;
  68.7% (11/16)—G3518;
  56.2% (9/16)—AtERF98, G1791, G3380, G3515, G3516, G3520, G3737, G3739, G3794;
  50.0% (8/16)—G30, G1795, G3381, G3383, G3517;
  43.7% (7/16)—G3736.

Since the EDLL motif has many acidic residues, it was predicted by us to have role in transcriptional activation. The present application confirms the transcriptional activation potential and transportability of function of this small peptide experimentally. To demonstrate experimentally the role of conserved EDLL motif, we fused a 24 amino acid peptide sequence comprising the EDLL domain of AtERF98 with a sequence-specific GAL4 DNA binding domain (DBD) from yeast (GAL4 DBD or "GD"). The chimeric protein, (GD-EDLL) when expressed in plant protoplasts, induced the expression of a reporter gene containing GAL4 DBD binding sequences in the promoter (FIG. 2). The GAL4 DBD alone without the EDLL motif (GD) could not induce the expression of the reporter gene significantly (FIG. 2). The activation of the reporter gene by the either one or two copies of the EDLL motif is comparable in magnitude to that obtained with the widely used VP16 activation domain from herpes simplex virus (FIGS. 2, 3). When the hydrophobic leucine residues were changed to valine ("EDLLm"), the activation potential of EDLL motif was significantly compromised (FIG. 2). Similarly, when orthologous EDLL motifs from *Medicago truncatula* (GD:G3735EDLL) and rice (GD:G3737EDLL) were tested, each produced reporter gene levels significantly higher than the GALA DNA binding domain alone (GD) (FIG. 3). Other orthologous EDLL motif sequences from crops such as corn, soybean and wheat will be tested in a similar manner.

We have also shown another example (FIG. 4) where an EDLL domain was fused to NF-YB1 (G481, SEQ ID NO: 73), a protein which lacks a native strong activation domain of its own and which does not bind DNA alone, but rather requires a DNA binding partner for recruitment to the promoter. When the G481:EDLL fusion was co-expressed in protoplasts with a yeast GAL4 DNA binding domain (GD) fused to G483 (SEQ ID NO: 74, the G481:EDLL-GD:G483 dimer induced the activity of reporter gene to a significant degree. Similar results were obtained with another NF-YC protein, G715, SEQ ID NO: 75, and the result was similar to that with G483. These results demonstrated the utility of the EDLL domain in activating transcription by way of a CCAAT element binding factor, which comprises a transcription regulatory polypeptide unrelated to the sequence from which the EDLL domain was derived (AtERF98). This also indicated that the EDLL motif can function in larger complexes, and can confer transcriptional activation function to a plant transcription factor lacking activation capacity. It is also active even if the protein is not binding DNA directly (G481:EDLL alone can not bind DNA; data not shown) but is recruited to the DNA via interaction with another DNA binding protein (GD:G483 or GD:715).

Orthologs and Paralogs

Homologous sequences as described above, such as sequences that are homologous to AtERF98 (SEQ ID NO: 2), or the EDLL domain of AtERF98 (SEQ ID NO: 37), can include orthologous or paralogous sequences (for example, SEQ ID NOs: 1-36, or EDLL domains 37-54). Several different methods are known by those of skill in the art for identifying and defining these functionally homologous sequences. General methods for identifying orthologs and paralogs, including phylogenetic methods, sequence similarity and hybridization methods, are described herein; an ortholog or paralog, including equivalogs, may be identified by one or more of the methods described below.

As described by Eisen (1998) *Genome Res.* 8: 163-167, evolutionary information may be used to predict gene function. It is common for groups of genes that are homologous in sequence to have diverse, although usually related, functions. However, in many cases, the identification of homologs is not sufficient to make specific predictions because not all homologs have the same function. Thus, an initial analysis of functional relatedness based on sequence similarity alone may not provide one with a means to determine where similarity ends and functional relatedness begins. Fortunately, it is well known in the art that protein function can be classified using phylogenetic analysis of gene trees combined with the corresponding species. Functional predictions can be greatly improved by focusing on how the genes became similar in sequence (that is, by evolutionary processes) rather than on the sequence similarity itself (Eisen, supra). In fact, many specific examples exist in which gene function has been shown to correlate well with gene phylogeny (Eisen, supra). Thus, "[t]he first step in making functional predictions is the generation of a phylogenetic tree representing the evolutionary history of the gene of interest and its homologs. Such trees are distinct from clusters and other means of characterizing sequence similarity because they are inferred by techniques that help convert patterns of similarity into evolutionary relationships . . . . After the gene tree is inferred, biologically determined functions of the various homologs are overlaid onto the tree. Finally, the structure of the tree and the relative phylogenetic positions of genes of different functions are used to trace the history of functional changes, which is then used to predict functions of [as yet] uncharacterized genes" (Eisen, supra).

Within a single plant species, gene duplication may cause two copies of a particular gene, giving rise to two or more genes with similar sequence and often similar function known as paralogs. A paralog is therefore a similar gene formed by duplication within the same species. Paralogs typically cluster together or in the same clade (a group of similar genes) when a gene family phylogeny is analyzed using programs such as CLUSTAL (Thompson et al. (1994) *Nucleic Acids Res.* 22: 4673-4680; Higgins et al. (1996) *Methods Enzymol.* 266: 383-402). Groups of similar genes can also be identified with pair-wise BLAST analysis (Feng and Doolittle (1987) *J. Mol. Evol.* 25: 351-360). For example, a clade of very similar MADS domain transcription factors from *Arabidopsis* all share a common function in flowering time (Ratcliffe et al. (2001) *Plant Physiol.* 126: 122-132, and a group of very similar AP2 domain transcription factors from *Arabidopsis* are involved in tolerance of plants to freezing (Gilmour et al. (1998) *Plant J.* 16: 433-442). Analysis of groups of similar genes with similar function that fall within one clade can yield sub-sequences that are particular to the clade. These sub-sequences, known as consensus sequences, can not only be used to define the sequences within each clade, but define the functions of these genes; genes within a clade may contain paralogous sequences, or orthologous sequences that share the same function (see also, for example, Mount (2001), in *Bioinformatics: Sequence and Genome Analysis*, Cold Spring Harbor Laboratory Press, Cold Spring Harbor, N.Y., p. 543)

Transcription factor gene sequences are conserved across diverse eukaryotic species lines (Goodrich et al. (1993) *Cell* 75: 519-530; Lin et al. (1991) *Nature* 353: 569-571; Sadowski et al. (1988) *Nature* 335: 563-564). Plants are no exception to this observation; diverse plant species possess transcription factors that have similar sequences and functions. Speciation, the production of new species from a parental species, gives rise to two or more genes with similar sequence and similar function. These genes, termed orthologs, often have an identical function within their host plants and are often interchangeable between species without losing function. Because plants have common ancestors, many genes in any plant species will have a corresponding orthologous gene in another plant species. Once a phylogenic tree for a gene family of one species has been constructed using a program such as CLUSTAL (Thompson et al., 1994, supra; Higgins et al., 1996, supra) potential orthologous sequences can be placed into the phylogenetic tree and their relationship to genes from the species of interest can be determined. Orthologous sequences can also be identified by a reciprocal BLAST strategy. Once an orthologous sequence has been identified, the function of the ortholog can be deduced from the identified function of the reference sequence.

Thus, the invention provides methods for identifying a sequence similar or paralogous or orthologous or homologous to one or more polynucleotides as noted herein, or one or more target polypeptides encoded by the polynucleotides, or otherwise noted herein and may include linking or associating a given plant phenotype or gene function with a sequence. In the methods, a sequence database is provided (locally or across an internet or intranet) and a query is made against the sequence database using the relevant sequences herein and associated plant phenotypes or gene functions.

In addition, one or more polynucleotide sequences or one or more polypeptides encoded by the polynucleotide sequences may be used to search against a BLOCKS (Bairoch et al. (1997) *Nucleic Acids Res.* 25: 217-221), PFAM, and other databases which contain previously identified and annotated motifs, sequences and gene functions. Methods that search for primary sequence patterns with secondary structure gap penalties (Smith et al. (1992) *Protein Engineering* 5: 35-51) as well as algorithms such as Basic Local Alignment Search Tool (BLAST; Altschul (1990) *J. Mol. Biol.* 215: 403-410, and Altschul (1993) *J. Mol. Evol.* 36: 290-300), BLOCKS (Henikoff and Henikoff (1991) *Nucleic Acids Res.* 19: 6565-6572), Hidden Markov Models (HMM; Eddy (1996) *Curr. Opin. Str. Biol.* 6: 361-365; Sonnhammer et al. (1997) *Proteins* 28: 405-420), and the like, can be used to manipulate and analyze polynucleotide and polypeptide sequences encoded by polynucleotides. These databases, algorithms and other methods are well known in the art and are described in Ausubel et al. (1997) *Short Protocols in Molecular Biology*, John Wiley & Sons, New York, N.Y., unit 7.7, and in Meyers (1995) *Molecular Biology and Biotechnology*, Wiley VCH, New York, N.Y., p 856-853.

Methods using manual alignment of sequences similar or homologous to one or more polynucleotide sequences or one or more polypeptides encoded by the polynucleotide sequences may be used to identify regions of similarity and conserved domains characteristic of a particular transcription factor family. Such manual methods are well-known of those of skill in the art and can include, for example, comparisons of tertiary structure between a polypeptide sequence encoded by a polynucleotide that comprises a known function and a polypeptide sequence encoded by a polynucleotide sequence that has a function not yet determined. Such examples of tertiary structure may comprise predicted alpha helices, beta-sheets, amphipathic helices, leucine zipper motifs, zinc finger motifs, proline-rich regions, cysteine repeat motifs, and the like.

EDLL domains of presently disclosed polypeptides may be cloned using compositions provided by the present invention according to methods well known in the art. cDNAs can be cloned using mRNA from a plant cell or tissue that expresses one of the present sequences. Appropriate mRNA sources may be identified by interrogating Northern blots with probes designed from the present sequences, after which a library is prepared from the mRNA obtained from a positive cell or tissue. Polypeptide-encoding cDNA is then isolated using, for example, PCR, using primers designed from a presently disclosed gene sequence, or by probing with a partial or complete cDNA or with one or more sets of degenerate probes based on the disclosed sequences. The cDNA library may be used to transform plant cells. Expression of the cDNAs of interest is detected using, for example, microarrays, Northern blots, quantitative PCR, or any other technique for monitoring changes in expression. Genomic clones may be isolated using similar techniques to those.

Examples of EDLL domains from polypeptide sequences of *Arabidopsis* and other plant species are listed in Table 1 and in the Sequence Listing as SEQ ID NOs: 37-54. In addition to the sequences in Table 1 and the Sequence Listing, the invention includes, but is not limited to, isolated polypeptide sequences that are phylogenetically and structurally similar to EDLL sequences listed in Table 1, and in the Sequence Listing as SEQ ID NOs: 37-54, and can function in a plant as a transcriptional activation domain, or by activating gene transcription and increasing the expression of a protein in a living organism or in vitro gene or protein expression system. The invention includes, but is not limited to, protein sequences that are found in the Sequence Listing as SEQ ID NOs: 2n, where n=1-18, or structurally similar sequences, when the sequences include an EDLL domain that functions as a transcriptional activation domain.

Sequence Variations

It will readily be appreciated by those of skill in the art, that any of a variety of polynucleotide sequences are capable of encoding the transcription factors and transcription factor homolog polypeptides that function similarly to those provided in the Sequence Listing or Table 1. Due to the degeneracy of the genetic code, many different polynucleotides can encode identical and/or substantially similar polypeptides in addition to those sequences illustrated in the Sequence Listing. Nucleic acids having a sequence that differs from the sequences shown in the Sequence Listing, or complementary sequences, that encode functionally equivalent peptides (that is, peptides having some degree of equivalent or similar biological activity) but differ in sequence from the sequence shown in the sequence listing due to degeneracy in the genetic code, are also within the scope of the invention.

Altered polynucleotide sequences encoding polypeptides include those sequences with deletions, insertions, or substitutions of different nucleotides, resulting in a polynucleotide encoding a polypeptide with at least one functional characteristic of the instant polypeptides. Included within this definition are polymorphisms which may or may not be readily detectable using a particular oligonucleotide probe of the polynucleotide encoding the instant polypeptides, and improper or unexpected hybridization to allelic variants, with a locus other than the normal chromosomal locus for the polynucleotide sequence encoding the instant polypeptides.

Sequence alterations that do not change the amino acid sequence encoded by the polynucleotide are termed "silent" variations. With the exception of the codons ATG and TGG, encoding methionine and tryptophan, respectively, any of the possible codons for the same amino acid can be substituted by a variety of techniques, for example, site-directed mutagenesis, available in the art. Accordingly, any and all such variations of a sequence selected from the above table are a feature of the invention.

In addition to silent variations, other conservative variations that alter one, or a few amino acids in the encoded polypeptide, can be made without altering the function of the polypeptide. For example, substitutions, deletions and insertions introduced into the sequences provided in the Sequence Listing are also envisioned. Such sequence modifications can be engineered into a sequence by site-directed mutagenesis (for example, Olson et al., Smith et al., Zhao et al., and other articles in Wu (ed.) *Meth. Enzymol.* (1993) vol. 217, Academic Press) or the other methods known in the art or noted herein. Amino acid substitutions are typically of single residues; insertions usually will be on the order of about from 1 to 10 amino acid residues; and deletions will range about from 1 to 30 residues. In preferred embodiments, deletions or insertions are made in adjacent pairs, for example, a deletion of two residues or insertion of two residues. Substitutions, deletions, insertions or any combination thereof can be combined to arrive at a sequence. The mutations that are made in the polynucleotide encoding the transcription factor should not place the sequence out of reading frame and should not create complementary regions that could produce secondary mRNA structure. Preferably, the polypeptide encoded by the DNA performs the desired function.

Conservative substitutions are those in which at least one residue in the amino acid sequence has been removed and a different residue inserted in its place. Such substitutions generally are made in accordance with the Table 2 when it is desired to maintain the activity of the protein. Table 2 shows amino acids which can be substituted for an amino acid in a protein and which are typically regarded as conservative substitutions.

TABLE 2

| Possible conservative amino acid substitutions | |
|---|---|
| Amino Acid Residue | Conservative substitutions |
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

The EDLL domains provided in the Sequence Listing or in Table 1 have a novel activity, being plant transcription activation domains that may be used to activate transcription of heterologous transcription regulatory proteins. Although all conservative amino acid substitutions (for example, one basic amino acid substituted for another basic amino acid) in the EDLL domain will not necessarily result in a protein that has transcriptional activation activity, it is expected that many of these conservative mutations would result in an EDLL domain having transcriptional activation activity. Most mutations, conservative or non-conservative, made to a protein having an EDLL domain, but outside of the EDLL domain and outside of other domains essential for protein activity, will not affect the activity of the EDLL domain to any great extent.

Identifying Polynucleotides or Polypeptides Related to the Disclosed Sequences by Percent Identity With the aid of a computer, one of skill in the art could identify all of the polypeptides, or all of the nucleic acids that encode a polypeptide, with, for example, at least 85% identity to the sequences provided herein and in the Sequence Listing. Electronic analysis of sequences may be conducted with a software program such as the MEGALIGN program (DNASTAR, Inc. Madison, Wis.). The MEGA-LIGN program can create alignments between two or more sequences according to different methods, for example, the clustal method (see, for example, Higgins and Sharp (1988) *Gene* 73: 237-244). The clustal algorithm groups sequences into clusters by examining the distances between all pairs. The clusters are aligned pairwise and then in groups. Other alignment algorithms or programs may be used, including FASTA, BLAST, or ENTREZ, FASTA and BLAST, and which may be used to calculate percent similarity. These are available as a part of the GCG sequence analysis package (University of Wisconsin, Madison, Wis.), and can be used with or without default settings. ENTREZ is available through the National Center for Biotechnology Information. In one embodiment, the percent identity of two sequences can be determined by the GCG program with a gap weight of 1, for example, each amino acid gap is weighted as if it were a single amino acid or nucleotide mismatch between the two sequences (see U.S. Pat. No. 6,262,333).

Software for performing BLAST analyses is publicly available, for example, through the National Center for Biotechnology Information (see internet website at www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul, 1990, supra; Altschul et al., 1993, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, a cutoff of 100, M=5, N=−4, and a comparison of both strands. For amino acid sequences, the BLASTP program uses as defaults a wordlength (W) of 3, an expectation (E) of 10, and the BLOSUM62 scoring matrix (see Henikoff and Henikoff (1989) *Proc. Natl. Acad. Sci. USA* 89: 10915). Unless otherwise indicated for comparisons of predicted polynucleotides, "sequence identity" refers to the % sequence identity generated from a tblastx using the NCBI version of the algorithm at the default settings using gapped alignments with the filter "off" (see, for example, internet website at www.ncbi.nlm.nih.gov/).

Other techniques for alignment are described by Doolittle, ed. (1996) *Methods in Enzymology*, vol. 266: "Computer Methods for Macromolecular Sequence Analysis" Academic Press, Inc., San Diego, Calif., USA. Preferably, an alignment program that permits gaps in the sequence is utilized to align the sequences. The Smith-Waterman is one type of algorithm that permits gaps in sequence alignments (see Shpaer (1997) *Methods Mol. Biol.* 70: 173-187). Also, the GAP program using the Needleman and Wunsch alignment method can be utilized to align sequences. An alternative search strategy uses MPSRCH software, which runs on a MASPAR computer. MPSRCH uses a Smith-Waterman algorithm to score sequences on a massively parallel computer. This approach improves ability to pick up distantly related matches, and is especially tolerant of small gaps and nucleotide sequence errors. Nucleic acid-encoded amino acid sequences can be used to search both protein and DNA databases.

Percent identity can also be determined manually, by comparing the entire length of a sequence of sequence with another in an optimal alignment.

Generally, the percentage similarity between two polypeptide sequences, for example, sequence A and sequence B, is calculated by dividing the length of sequence A, minus the number of gap residues in sequence A, minus the number of gap residues in sequence B, into the sum of the residue matches between sequence A and sequence B, times one hundred. Gaps of low or of no similarity between the two amino acid sequences are not included in determining percentage similarity. Percent identity between polynucleotide sequences can also be counted or calculated by other methods known in the art, for example, the Jotun Hein method (see, for example, Hein (1990) *Methods Enzymol.* 183: 626-645). Identity between sequences can also be determined by other methods known in the art, for example, by varying hybridization conditions (see US Patent Application No. US20010010913).

At the polynucleotide level, the sequences described herein in the Sequence Listing, and the sequences of the invention by virtue of a paralogous or homologous relationship with the sequences described in the Sequence Listing, will typically share at least about 30%, or 40% nucleotide sequence identity, preferably at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% sequence identity to one or more of the listed full-length sequences, or to a region of a listed sequence excluding or outside of the region(s) encoding a known consensus sequence or consensus DNA-binding site, or outside of the region(s) encoding one or all conserved domains. The degeneracy of the genetic code enables major variations in the nucleotide sequence of a polynucleotide while maintaining the amino acid sequence of the encoded protein.

At the polypeptide level, the sequences described herein in the Sequence Listing and Table 1, and the sequences of the invention by virtue of a paralogous or homologous relationship with the sequences described in the Sequence Listing or in Table 1, will typically share at least about 50%, at least about 51%, at least about 52%, at least about 53%, at least about 54%, at least about 55%, at least about 56%, at least about 57%, at least about 58%, at least about 59%, at least about 60%, at least about 61%, at least about 62%, at least about 63%, at least about 64%, at least about 65%, at least about 66%, at least about 67%, at least about 68%, at least about 69%, at least about 70%, at least about 71%, at least about 72%, at least about 73%, at least about 74%, at least about 75%, at least about 76%, at least about 77%, at least about 78%, at least about 79%, at least about 80%, at least about 81%, at least about 82%, at least about 83%, at least about 84%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, at least about 99%, or about 100% amino acid sequence identity or more sequence identity to one or more of the listed full-length sequences, including full-length and EDLL domain sequences, or to a listed sequence but excluding or outside of the known consensus sequence or consensus DNA-binding site.

Identifying Polynucleotides Related to the Disclosed Sequences by Hybridization

Polynucleotides homologous to the sequences illustrated in the Sequence Listing and tables can be identified, for example, by hybridization to each other under stringent or under highly stringent conditions. Single stranded polynucleotides hybridize when they associate based on a variety of well characterized physical-chemical forces, such as hydrogen bonding, solvent exclusion, base stacking and the like. The stringency of a hybridization reflects the degree of sequence identity of the nucleic acids involved, such that the higher the stringency, the more similar are the two polynucleotide strands. Stringency is influenced by a variety of factors, including temperature, salt concentration and composition, organic and non-organic additives, solvents, etc. present in both the hybridization and wash solutions and incubations (and number thereof), as described in more detail in the references cited below (for example, Sambrook et al. (1989) *Molecular Cloning: A Laboratory Manual*, 2nd Ed., Cold Spring Harbor Laboratory, Cold Spring Harbor, N.Y.; Schroeder et al. (2002) *Current Biol.* 12, 1462-1472; Berger and Kimmel (1987), "Guide to Molecular Cloning Techniques", in *Methods in Enzymology*, vol. 152, Academic Press, Inc., San Diego, Calif.; and Anderson and Young (1985) "Quantitative Filter Hybridisation", In: Hames and Higgins, ed., *Nucleic Acid Hybridisation, A Practical Approach.* Oxford, IRL Press, 73-111).

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger (1987) *Methods Enzymol.* 152: 399-407; and Kimmel (1987) *Methods Enzymol.* 152: 507-511). In addition to the nucleotide sequences listed in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

With regard to hybridization, conditions that are highly stringent, and means for achieving them, are well known in the art. See, for example, Sambrook et al., 1989; Berger, 1987, pages 467-469; and Anderson and Young, 1985, all supra.

Stability of DNA duplexes is affected by such factors as base composition, length, and degree of base pair mismatch. Hybridization conditions may be adjusted to allow DNAs of different sequence relatedness to hybridize. The melting temperature ($T_m$) is defined as the temperature when 50% of the duplex molecules have dissociated into their constituent single strands. The melting temperature of a perfectly matched duplex, where the hybridization buffer contains formamide as a denaturing agent, may be estimated by the following equations:

(I) DNA-DNA:

$$T_m(°C.)=81.5+16.6(\log [Na+])+0.41(\% \ G+C)-0.62(\% \ \text{formamide})-500/L$$

(II) DNA-RNA:

$$T_m(°C.)=79.8+18.5(\log [Na+])+0.58(\% \ G+C)+0.12(\% \ G+C)^2-0.5(\% \ \text{formamide})-820/L$$

(III) RNA-RNA:

$$T_m(°C.)=79.8+18.5(\log [Na+])+0.58(\% \ G+C)+0.12(\% \ G+C)^2-0.35(\% \ \text{formamide})-820/L$$

where L is the length of the duplex formed, [Na+] is the molar concentration of the sodium ion in the hybridization or washing solution, and % G+C is the percentage of (guanine+cytosine) bases in the hybrid. For imperfectly matched hybrids, approximately 1° C. is required to reduce the melting temperature for each 1% mismatch.

Hybridization experiments are generally conducted in a buffer of pH between 6.8 to 7.4, although the rate of hybridization is nearly independent of pH at ionic strengths likely to be used in the hybridization buffer (Anderson and Young, 1985, supra). In addition, one or more of the following may be used to reduce non-specific hybridization: sonicated salmon sperm DNA or another non-complementary DNA, bovine serum albumin, sodium pyrophosphate, sodium dodecylsulfate (SDS), polyvinyl-pyrrolidone, ficoll and Denhardt's solution. Dextran sulfate and polyethylene glycol 6000 act to exclude DNA from solution, thus raising the effective probe DNA concentration and the hybridization signal within a given unit of time. In some instances, conditions of even greater stringency may be desirable or required to reduce non-specific and/or background hybridization. These conditions may be created with the use of higher temperature, lower ionic strength and higher concentration of a denaturing agent such as formamide.

Stringency conditions can be adjusted to screen for moderately similar fragments such as homologous sequences from distantly related organisms, or to highly similar fragments such as genes that duplicate functional enzymes from closely related organisms. The stringency can be adjusted either during the hybridization step or in the post-hybridization washes. Salt concentration, formamide concentration, hybridization temperature and probe lengths are variables that can be used to alter stringency (as described by the formula above). As a general guidelines high stringency is typically performed at $T_m-5°$ C. to $T_m-20°$ C., moderate stringency at $T_m-20°$ C. to $T_m-35°$ C. and low stringency at $T_m-35°$ C. to $T_m-50°$ C. for duplex >150 base pairs.

Hybridization may be performed at low to moderate stringency (25-50° C. below $T_m$), followed by post-hybridization washes at increasing stringencies. Maximum rates of hybridization in solution are determined empirically to occur at $T_m$–25° C. for DNA-DNA duplex and $T_m$–15° C. for RNA-DNA duplex. Optionally, the degree of dissociation may be assessed after each wash step to determine the need for subsequent, higher stringency wash steps.

High stringency conditions may be used to select for nucleic acid sequences with high degrees of identity to the disclosed sequences. An example of stringent hybridization conditions obtained in a filter-based method such as a Southern or Northern blot for hybridization of complementary nucleic acids that have more than 100 complementary residues is about 5° C. to 20° C. lower than the thermal melting point ($T_m$) for the specific sequence at a defined ionic strength and pH. Conditions used for hybridization may include about 0.02 M to about 0.15 M sodium chloride, about 0.5% to about 5% casein, about 0.02% SDS or about 0.1% N-laurylsarcosine, about 0.001 M to about 0.03 M sodium citrate, at hybridization temperatures between about 50° C. and about 70° C. More preferably, high stringency conditions are about 0.02 M sodium chloride, about 0.5% casein, about 0.02% SDS, about 0.001 M sodium citrate, at a temperature of about 50° C. Nucleic acid molecules that hybridize under stringent conditions will typically hybridize to a probe based on either the entire DNA molecule or selected portions, for example, to a unique subsequence, of the DNA.

Stringent salt concentration will ordinarily be less than about 750 mM NaCl and 75 mM trisodium citrate. Increasingly stringent conditions may be obtained with less than about 500 mM NaCl and 50 mM trisodium citrate, to even greater stringency with less than about 250 mM NaCl and 25 mM trisodium citrate. Low stringency hybridization can be obtained in the absence of organic solvent, for example, formamide, whereas high stringency hybridization may be obtained in the presence of at least about 35% formamide, and more preferably at least about 50% formamide. Stringent temperature conditions will ordinarily include temperatures of at least about 30° C., more preferably of at least about 37° C., and most preferably of at least about 42° C. with formamide present. Varying additional parameters, such as hybridization time, the concentration of detergent, for example, sodium dodecyl sulfate (SDS) and ionic strength, are well known to those skilled in the art. Various levels of stringency are accomplished by combining these various conditions as needed.

The washing steps that follow hybridization may also vary in stringency; the post-hybridization wash steps primarily determine hybridization specificity, with the most critical factors being temperature and the ionic strength of the final wash solution. Wash stringency can be increased by decreasing salt concentration or by increasing temperature. Stringent salt concentration for the wash steps will preferably be less than about 30 mM NaCl and 3 mM trisodium citrate, and most preferably less than about 15 mM NaCl and 1.5 mM trisodium citrate.

Thus, hybridization and wash conditions that may be used to bind and remove polynucleotides with less than the desired homology to the nucleic acid sequences or their complements that encode the present polypeptides include, for example:

6×SSC and 1% SDS at 65° C.;
50% formamide, 4×SSC at 42° C.; or
0.5×SSC to 2.0×SSC, 0.1% SDS at 50° C. to 65° C.;

with a first wash step of, for example, 10 minutes at about 42° C. with about 20% (v/v) formamide in 0.1×SSC, and with, for example, a subsequent wash step with 0.2×SSC and 0.1% SDS at 65° C. for 10, 20 or 30 minutes. An example of an amino acid sequence of the invention would include one encoded by a polynucleotide selected from the group consisting of SEQ ID NO: 57-63 (nucleic acid sequence fragments encoding various EDLL domain that have been or can be used for cloning) and 76-93 (nucleic acid sequence fragments that encode various EDLL domains, and which can be incorporated into nucleic acid constructs for cloning purposes).

Useful variations on these conditions will be readily apparent to those skilled in the art.

A person of skill in the art would not expect substantial variation among polynucleotide species encompassed within the scope of the present invention because the highly stringent conditions set forth in the above formulae yield structurally similar polynucleotides.

If desired, one may employ wash steps of even greater stringency, including about 0.2×SSC, 0.1% SDS at 65° C. and washing twice, each wash step being about 30 minutes, or about 0.1×SSC, 0.1% SDS at 65° C. and washing twice for 30 minutes. The temperature for the wash solutions will ordinarily be at least about 25° C., and for greater stringency at least about 42° C. Hybridization stringency may be increased further by using the same conditions as in the hybridization steps, with the wash temperature raised about 3° C. to about 5° C., and stringency may be increased even further by using the same conditions except the wash temperature is raised about 6° C. to about 9° C. For identification of less closely related homologs, wash steps may be performed at a lower temperature, for example, 50° C.

An example of a low stringency wash step employs a solution and conditions of at least 25° C. in 30 mM NaCl, 3 mM trisodium citrate, and 0.1% SDS over 30 minutes. Greater stringency may be obtained at 42° C. in 15 mM NaCl, with 1.5 mM trisodium citrate, and 0.1% SDS over 30 minutes. Even higher stringency wash conditions are obtained at 65° C.-68° C. in a solution of 15 mM NaCl, 1.5 mM trisodium citrate, and 0.1% SDS. Wash procedures will generally employ at least two final wash steps. Additional variations on these conditions will be readily apparent to those skilled in the art (see, for example, US Patent Application No. US20010010913).

Stringency conditions can be selected such that an oligonucleotide that is perfectly complementary to the coding oligonucleotide hybridizes to the coding oligonucleotide with at least about a 5-10× higher signal to noise ratio than the ratio for hybridization of the perfectly complementary oligonucleotide to a nucleic acid encoding a polypeptide known as of the filing date of the application. It may be desirable to select conditions for a particular assay such that a higher signal to noise ratio, that is, about 15× or more, is obtained. Accordingly, a subject nucleic acid will hybridize to a unique coding oligonucleotide with at least a 2× or greater signal to noise ratio as compared to hybridization of the coding oligonucleotide to a nucleic acid encoding known polypeptide. The particular signal will depend on the label used in the relevant assay, for example, a fluorescent label, a colorimetric label, a radioactive label, or the like. Labeled hybridization or PCR probes for detecting related polynucleotide sequences may be produced by oligolabeling, nick translation, end-labeling, or PCR amplification using a labeled nucleotide.

Encompassed by the invention are polynucleotide sequences that are capable of hybridizing to the claimed polynucleotide sequences, including any of the polynucleotides within the Sequence Listing, and fragments thereof under various conditions of stringency (see, for example, Wahl and Berger, 1987, pages 399-407; and Kimmel, 1987). In addition to the nucleotide sequences in the Sequence Listing, full length cDNA, orthologs, and paralogs of the present nucleotide sequences may be identified and isolated using well-known methods. The cDNA libraries, orthologs, and paralogs of the present nucleotide sequences may be screened using hybridization methods to determine their utility as hybridization target or amplification probes.

EXAMPLES

It is to be understood that this invention is not limited to the particular devices, machines, materials and methods described. Although particular embodiments are described, equivalent embodiments may be used to practice the invention.

The invention, now being generally described, will be more readily understood by reference to the following examples, which are included merely for purposes of illustration of certain aspects and embodiments of the present invention and are not intended to limit the invention. It will be recognized by one of skill in the art that a polypeptide that is associated with a particular first trait may also be associated with at least one other, unrelated and inherent second trait which was not predicted by the first trait.

Example I: Identification of the EDLL Domain in Diverse Plant Species

Initial examination of the AtERF98 transcription factor sequence revealed the presence of a putative activation domain based on the presence of a high proportion of acidic and polar amino acids residue interspersed around hydrophobic leucines in a short stretch of the sequence near its c-terminus.

Of particular interest to us was whether this domain might exist, and function in a similar manner, in the form of homologs in plant species other than *Arabidopsis*. Homologous putative activation domains from *Arabidopsis* and other plant species were next identified using database sequence search tools, such as the Basic Local Alignment Search Tool (BLAST) (Altschul et al. (1990) supra; and Altschul et al. (1997) *Nucleic Acid Res.* 25: 3389-3402). tblastx sequence analysis programs were employed using the BLOSUM-62 scoring matrix (Henikoff and Henikoff (1992) *Proc. Natl. Acad. Sci. USA* 89: 10915-10919). The NCBI GenBank database was filtered for sequences by selecting all entries in the NCBI GenBank database associated with NCBI taxonomic ID 33090 (Viridiplantae; all plants). These sequences were compared to the AtERF98 EDLL domain sequence using the Washington University TBLASTX algorithm at the default settings using gapped alignments with the filter "off". Individual comparisons were ordered by probability score (P-value), where the score reflected the probability that a particular alignment occurred by chance. In addition to P-values, comparisons were also scored by percentage identity. Percentage identity reflects the degree to which two segments of DNA or protein are identical over a particular length. Paralogous or orthologous EDLL domain sequences were readily identified. Examples of sequences so identified are presented in Table 1.

Candidate paralogous and orthologous sequences were identified from proprietary unigene sets of plant gene sequences in *Zea mays, Glycine max, Oryza sativa, Triticum aestivum*, and *Medicago truncatula* based on significant homology to the AtERF98 EDLL domain sequence. These candidate EDLL motifs were reciprocally compared to the AtERF98 EDLL domain using a similar BLAST analysis. If the candidate EDLL domain showed maximal similarity to the eliciting EDLL domain, then it was considered to be an ortholog or paralog. Identified *Arabidopsis* and non-*Arabidopsis* sequences that were shown in this manner to be orthologous to the *Arabidopsis* sequences are provided in Table 1.

It is expected that the same methods may be applied to identify other useful and valuable EDLL domain sequences, and the EDLL domain sequences may be derived from a diverse range of species.

The percent sequence identity among the identified EDLL domain sequences examined thus far can be as low as 37.5% (6 of 16 residues identical), as indicated in Table 1 and the subsequent text provided above. Each of these sequences was discovered to have several highly conserved residues, as shown in FIG. 1. These include, in order from N- to C termini, the four residues of glutamic acid, aspartic acid, leucine and leucine residues as indicated in the consensus sequence SEQ ID NO: 55: $EX_4DX_3LX_3L$, where X can be any amino acid. This peptide was thus designated as the "EDLL domain" (sometimes referred to as the "EDLL motif"), based on these four conserved residues. In addition to the glutamic acid, aspartic acid, leucine and leucine residues, several other positions in this domain were recognized as highly conserved, exemplified by the consensus sequence E-L/F-$X_2$-L/F-D-D/N-$X_2$-L-$X_2$-L/M-L (SEQ ID NO: 56), or the consensus sequence E-F/L-X-X-L/F-D-D/N-X-V/L/I-L-X-X-L/M-L (SEQ ID NO: 94), or the consensus sequence E-F/L-E/V-Y/C/F-L/F-D-D/N-X-V/L-L-E/Q/D-E/D/S-L/M-L (SEQ ID NO: 95), where X is any amino acid and a "slash" indicates the possibility of alternative residues on either side of the slash (or slashes) at a given position. For example, L/F refers to a leucine or phenylalanine residue, D/N refers to a aspartic acid or asparagine residue, L/M refers to a leucine or methionine residue, and C/F/Y refers to a cysteine residue, a phenylalanine residue, or a tyrosine residue at the indicated position.

Example II: Transformation Methods

Transformation of *Arabidopsis* with a nucleic acid constructs, such as a construct encoding an EDLL domain, is performed by an *Agrobacterium*-mediated protocol based on the method of Bechtold and Pelletier (1998) *Methods Mol. Biol.* 82: 259-266. Unless otherwise specified, all experimental work is done using the Columbia ecotype.

Plant Preparation.

*Arabidopsis* seeds are sown on mesh covered pots. The seedlings are thinned so that 6-10 evenly spaced plants remain on each pot 10 days after planting. The primary bolts are cut off a week before transformation to break apical dominance and encourage auxiliary shoots to form. Transformation is typically performed at 4-5 weeks after sowing.

Bacterial Culture Preparation.

*Agrobacterium* stocks are inoculated from single colony plates or from glycerol stocks and grown with the appropriate antibiotics and grown until saturation. On the morning of transformation, the saturated cultures are centrifuged and bacterial pellets are re-suspended in Infiltration Media (0.5×

MS, 1× B5 Vitamins, 5% sucrose, 1 mg/ml benzylaminopurine riboside, 200 µl/L Silwet L77) until an A600 reading of 0.8 is reached.

Transformation and Seed Harvest.

The *Agrobacterium* solution is poured into dipping containers. All flower buds and rosette leaves of the plants are immersed in this solution for 30 seconds. The plants are laid on their side and wrapped to keep the humidity high. The plants are kept this way overnight at 22° C. and then the pots are turned upright, unwrapped, and moved to the growth racks.

The plants are maintained on a growth rack under 24-hour light until seeds are ready to be harvested. Seeds are harvested when 80% of the siliques of the transformed plants are ripe (approximately 5 weeks after the initial transformation). This transformed seed is deemed T0 seed, since it is obtained from the T0 generation, and is later plated on selection plates (typically either kanamycin or sulfonamide, depending on the selectable marker gene included in the transformation construct). Resistant plants that are identified on such selection plates comprise the T1 generation.

Example III: Protoplast-Based Transcriptional Activation Assays

Carrot (*Daucus carota*) protoplasts were isolated from suspension cultures and transfected essentially by the method of Liu (1994) *Plant Cell* 6: 645-657. Briefly, plant protoplasts were prepared from a carrot suspension culture maintained at log phase in "carrot suspension medium" (CSM). A fresh culture was prepared by inoculating 50 ml fresh CSM media with 5 mL of 7-day old suspension cell culture and grown 5 days at room temperature. The suspension cells were collected by centrifugation (1000 rpm, 3 min) and resuspended in an equal volume of Driselase solution (Sigma-Aldrich). Driselase, a mixture of fungal enzymes, hydrolyzes cellulose (to glucose) and all the major matrix polysaccharides (to monosaccharides and/or characteristic disaccharides). The suspension culture was poured into 15 mm Petri dishes and incubated 3 h at room temperature. The protoplasts were filtered through a nylon membrane and washed twice with a W5 solution. Each time the protoplasts were pelleted by centrifugation (100 rpm, 3 min) and resuspended by gentle inversion. The final solution was then incubated on ice for 30 min. Prior to transformation, the protoplast cells were pelleted and resuspended in MC solution to a final concentration of $2\times10^6$ cells/ml, usually 25-30 ml. Approximately $5\times10^5$ cells (300 µl of the suspension) were transformed by adding 10 µg of high quality plasmid DNA and an equal volume of 40% PEG, swirled gently and incubated at room temperature for 20 min. The solution was then diluted to 5 ml using CSM media and incubated an additional 16-18 h to allow for protein expression. The protoplasts were pelleted by centrifugation (1000 rpm, 3 min), the cells disrupted in lysis buffer and the sample assayed for GUS activity by the method of Liu et al, 1995, supra. At least three replicate transfections were performed for each set of constructs analyzed.

Sequences to be analyzed for transcriptional activation potential were fused to a sequence-specific GAL4 DNA binding domain (GAL4 DBD or GD in the text) from yeast. The GAL4 DNA binding domain lacks any activation sequence; hence alone it can not activate the transcription of any gene. This construct was co-transfected with a reporter construct containing GAL4 binding sequences (UAS) in the promoter, fused to the reporter gene β-glucuronidase (GUS). In an alternate approach, sequences to be analyzed for activation ability were fused to another transcription factor protein, and the GAL4 DBD was fused to a second protein that interacts with the first protein, so that transcriptional activation occurs upon the interaction of the two proteins.

Example IV: Analysis of the EDLL Domain as a Transcription Activator

To analyze the function of the EDLL motif, a 24 amino acid peptide comprising the EDLL motif from AtERF98 (G1792) was fused with the GAL4 DNA binding domain (GAL4 DBD or GD in the text) from yeast. The GAL4 DBD:EDLL fusion protein (GD:EDLL in the text) was co-transfected into plant protoplasts along with a reporter gene (in this case β-glucuronidase, GUS) containing GAL4 binding sequences (UAS) in the promoter (FIG. 2). The chimeric protein, ("GD-EDLL" in this figure), when expressed in plant protoplasts, induced GUS expression to approximately the same extent as a fusion of the GAL4 DBD with the well-characterized VP16 activation domain (GD-VP16), whereas the GAL4 DBD alone (GD) which lacks any activation sequences could not induce GUS expression. When the conserved hydrophobic leucine residues were changed to valine ("EDLLm"), the activation potential of EDLL motif was significantly compromised. Two copies of the EDLL motif were also shown to be effective in transcription activation (FIG. 3; "GD:EDLL(2x)")

Results presented in FIG. 4 demonstrated the utility of the EDLL domain in activating transcription by way of a transcription regulatory polypeptide (G481, an NF-Y or CCAAT-binding transcription factor) unrelated to the sequence from which the EDLL domain was derived (AtERF98, an AP2 family transcription factor. These results demonstrated that the EDLL motif can confer transcriptional activation function to a plant transcription factor or other sequence of interest lacking activation capacity. Furthermore, the EDLL motif is also active even if the protein is not binding DNA directly (G481: EDLL alone can not bind DNA; data not shown) but is recruited to the DNA via interaction with another DNA binding protein (for example, GD:G483 or GD:G715), demonstrating that it can function in larger transcriptional complexes.

Results presented in FIG. 5 demonstrated that the EDLL motif can function to convert a transcriptional repressor into a transcriptional activator. G400, SEQ ID NO: 116, is a homeodomain-leucine zipper (HD-Zip) transcription factor that contains a repression domain termed an EAR domain (Ciarbelli et al. (2008) *Plant Mol Biol.* 68: 465-478). This protein binds to the promoter of another HD-Zip gene (prG398; SEQ ID NO: 99), but does not activate transcription (Myc:G400; encoded by SEQ ID NO: 128) relative to a non-specific control construct (CAT). Addition of the EDLL domain to this transcription factor (G400:EDLL:Myc; encoded by SEQ ID NO: 130) produced significant activation of prG398:GUS fusion construct, even though the native repression domain was still present. Addition of the EDLL domain to a variant of G400 with the EAR domain mutated (G400EAR:EDLL:Myc; encoded by SEQ ID NO: 98) produced even greater activation of the reporter fusion.

The EDLL motif was fused to various transcription factors and transformed into *Arabidopsis* plants. For example, the AP2 transcription factor G28, which when overexpressed produces plants that are smaller in size, darker green, later flowering and more disease resistant than comparable control plants, was fused to the EDLL domain (SEQ ID NO: 100) and transformed into *Arabidopsis* plants under the control of the constitutive 35S promoter (SEQ ID NO:

115) and the pathogen-inducible promoter prAT1G35230 (SEQ ID NO: 114). Plants from a T1 population of 35S::G28:EDLL (SEQ ID NO: 100) plants were generally smaller and darker green than those in a comparable T1 population of 35S::G28 plants, indicating that the EDLL fusion has greater potency than G28 alone. An enhanced dark green phenotype, as exhibited by the 35S::G28:EDLL lines could be indicative of enhanced photosynthetic potential, which could lead to enhanced yield. These plants as well as plants expressing G28:EDLL under prAT1G35230 will be assayed for disease resistance, and we anticipate that the G28:EDLL fusions will produce stronger disease resistance than the unmodified G28 transcription factor. Similarly, a number of transcription factors that provide abiotic stress tolerance (e.g. drought tolerance) when overexpressed have been modified by addition of the EDLL domain and transformed into *Arabidopsis* under the constitutive 35S promoter, the abiotic stress inducible RD29a promoter (SEQ ID NO: 111), or the drought inducible prAt5G43840 (SEQ ID NO: 112) and prAT5G52300 (SEQ ID NO: 113) promoters. These include the NF-YB transcription factors G481 (SEQ ID NO: 73, encoded by the G481:EDLL:cMyc fusion SEQ ID NO: 96) and G482 (SEQ ID NO: 131, encoded by the G482:EDLL fusion SEQ ID NO: 109), the WRKY transcription factor G1274 (SEQ ID NO: 132, encoded by the 35S::G1274:EDLL fusion SEQ ID NO: 101), the RAV transcription factor G867 (SEQ ID NO: 133, encoded by the prAt5G43840::G867:EDLL fusion SEQ ID NO: 102), the MADS transcription factor G1760 (SEQ ID NO: 134, encoded by the prAt5G43840::G1760:EDLL fusion SEQ ID NO: 104), the AP2 transcription factors G913 (SEQ ID NO: 135) and G912 (SEQ ID NO: 136), and the bHLH transcription factor G2932 (SEQ ID NO: 137). In addition, we fused the EDLL domain to two transcription factors that interact with the NF-YB transcription factor G481 and which could potentially be recruited to the NF-Y complex: the NF-YA transcription factor G926 (SEQ ID NO: 138) and the NF-YC transcription factor G715 (SEQ ID NO: 139). We anticipate that these transcription factors with the addition of the EDLL domain will produce more potent stress tolerance or confer a greater enhancement of yield potential than the comparable unmodified transcription factors.

The EDLL motif will be assayed as a fusion to other DNA binding proteins (transcription factors and co-regulators in plants). These EDLL chimeric fusion proteins will be transformed into *Arabidopsis* and other crop plants. Various promoters such as constitutive promoters (for example, Cauliflower Mosaic Virus 35S, rice actin) tissue-specific promoters, and the native promoters of the transcription factors to be tested will be used for the expression of chimeric proteins. It is expected that these chimeric proteins will confer various beneficial agronomic traits, including, for example, increased yield, improved water deficit tolerance, enhanced tolerance to hyperosmotic stress, enhanced tolerance to low or high temperatures, increased photosynthetic efficiency, increased disease resistance, earlier or delayed flowering time, and/or enhanced quantity or quality of proteins in seeds and tubers, relative to a control plant or relative to a plant comparably transformed with the DNA binding protein without the EDLL chimeric fusion.

Example V: Analysis of EDLL Domains from Diverse Plant Species

Peptides comprising EDLL motifs from soy, *Medicago*, rice, and maize, as well as the EDLL motif from an *Arabidopsis* paralog of AtERF98 (G30), were synthesized and cloned in frame with the yeast GAL4DNA binding domain (GD). The activation function of these sequences was analyzed as described for the AtERF98 EDLL domain in Example III, and all of these sequences produced transcriptional activation of the reporter gene (FIG. 6).

Thus, the EDLL motif is conserved in diverse plant genera including eudicots and monocots. The number of sequences described herein, for example, in Table 1 or the sequence listing, represent a practical sampling of a considerable number of sequence species. Between the eudicots soy, alfalfa, and *Arabidopsis*, and the monocots rice, wheat, and maize, are a very large number of plant species and their related sequences. There are about 199,350 eudicot plant species (Thorne (2002) *Taxon* 51: 511-512) that can produce G1792 clade member proteins evolutionarily more closely related to SEQ ID NO: 37 than to EDLL domains from the rice or maize orthologs. As shown below, EDLL domains from both monocot and dicot species have retained function as well as structure. These functionally-related sequences indicate that a considerable majority, if not all or almost all, of the plant species between *Arabidopsis* and monocot species will have conserved their EDLL domain sequences and associated function. Many orthologous monocot-derived sequences (there are about 59,300 monocot species; Thorne (2002) supra) should also retain similar functions; it seems unlikely that rice, wheat and maize are the only monocot plants to have retained orthologous EDLL domains after 130 to 240 million years of evolution (the generally accepted span from the monocot-eudicot divergence). Thus, a very large number of functional EDLL domain sequences can be readily found in plant species that lie in intermediate positions on the evolutionary tree.

The EDLL motif will be isolated from other crop orthologs such as wheat using similar approaches. These motifs from various crop orthologs will be analyzed using approaches described in Example III. We are also intending to isolate EDLL motifs by using genome sequencing, cDNA and genomic library screening or by RT-PCR using degenerate oligos from varieties such as *Sorghum, Miscanthus* and others plants where sequence information is not available. The motifs from these species will be analyzed similarly for their activation potential. Additionally, artificial EDLL motifs may be designed and created by synthesis and cloned in frame with yeast GAL4DNA binding domain (GD) and analyzed similarly for their activation potential.

Example VI: Activation of Various Transcription Regulatory Polypeptides with the EDLL Domain In addition to the transcription factors described above that were modified by addition of an EDLL domain, it can be anticipated that other transcription factors or other polypeptides of interest could be similarly modified. Appendix A provides further examples of *A. thaliana* transcription factor and other protein sequences that can be modified by fusion to one or more of the EDLL domains found in Table 1, or in variants thereof, as provided herein or manufactured using methods known in the art. Homologs of these transcription factor and other sequences may also be so modified. In this regard, "homolog" is defined as a gene encoding a particular protein sequence from a eukaryotic organism including *Arabidopsis thaliana* (in the case or paralogs) or other than *A. thaliana* (in the case or orthologs): (a) that when compared to the set of protein sequences encoded by the *A. thaliana* genome, has a similarity equal to or better than the "Minimum Similarity Requirement" (defined below); and (b) that is more similar to a gene in Appendix A than it is to any other protein sequence encoded by the *A. thaliana* genome. Similarity may be measured using the BLASTP algorithm available from the National Center for Biotechnology Information with, for example, the default parameters of the software program. The "Minimum Similarity Requirement" for a match may be defined as a high-scoring segment pair (HSP(s)) of bit score fifty (50) or better.

Example VII: Practical Benefits of Using the EDLL Domain for Enhancing Transcription The EDLL domain is a new transcriptional activation domain identified from a plant protein. It is highly active when fused with different class of DBD proteins from plants and yeast and has activation potential comparable to widely used VP16 activation domain, derived from Herpes simplex. The domain has many practical benefits. Some of these are described below:

1. Small size Unlike other known activation domains such as VP16 and GAL4, EDLL is relatively small in size and fusing of a peptide this small to any protein has a lower chance of altering the native conformation of a fusion protein. Further deletion analysis to determine the minimum region required for transcriptional activation is in progress.
2. Plant-derived. The EDLL domain is the first strong transcriptional activation domain from a plant species to be well-characterized. Transcription factors containing this domain are also present in many other plant species including useful crop varieties like rice, maize, soybean and alfalfa. The EDLL domain from these crops, or from other plant species, can be fused with transcription factors isolated from same species, or other plant species, and can be used for enhanced induction of any target genes in those crop varieties. This approach affords enhanced activation of TF targets while avoiding contamination of the crop genome with expressed genetic materials derived from outside of the plant kingdom.
3. Strong activation potential. Based on our experimental analyses described above, the EDLL motif has activation potential at least similar to, if not higher than most characterized activation domains in the literature, for example, VP16.
4. Optimization of activity. The strength of the EDLL domain activation potential may be fine-tuned by modifying one or more amino acid residues in the domain, for example, through the use of site-specific mutagenesis. In this manner, the ability of a specific transcription factor to activate transcription of its target genes can be adjusted to a greater or lesser extent with the use of a native or modified EDLL domain.
5. Broad activity. The EDLL motif is active on proteins isolated from both plants and yeast, and it is also active when targeted to the promoter of the desired gene by a protein with a DNA binding motif or through a protein-protein interaction motif. These properties of the EDLL motif make it a useful tool for targeted induction of desired genes in plants, and also it can be used for making research tools for protein-DNA and protein-protein interactions in bacteria, yeast, plants and animals.
6. Suppression of repression. The EDLL motif will be used to convert a repressor protein to an activator: We have shown experimentally (see, for example, the description of FIG. 4, above) that the NF-YB protein G481, which alone has no transcriptional activation capacity, can be converted into an activator by fusing it to an EDLL motif. Overexpression of G481 protein in *Arabidopsis* produces down-regulation of the flowering modulator gene FT, which in turn causes delay in flowering. The G481:EDLL chimeric protein is being expressed in plants and it is anticipated that the chimeric protein which functions as an activator will accelerate flowering. The EDLL motif is also being fused to other subunits of the NF-Y protein complex, and to other transcription factors and co-regulators of various physiological and developmental pathways in plants.
7. Agronomic potential. The EDLL activation domain has a wide range of agronomic potential. The expression of any gene can be regulated by fusing the EDLL motif to a sequence-specific DNA binding protein or various co-regulators capable of binding to the promoter of that target gene. Various developmental, physiological and environmental pathways could be modulated by these means, including, cell division and growth, photosynthesis, shade avoidance, drought and temperature tolerance, and disease resistance, with the goal of enhancing yield in crop varieties. It can also be used for enhancing the accumulation and quality of protein in plants like cassava and other tuber forming varieties routinely being used as major food crops in African countries, or modifying the accumulation of carbohydrates, including starches and sugars, in important food or fuel crops including but not limited to corn, rice, wheat, sorghum, sugar cane, miscane (a sugar cane×*Miscanthus* hybrid cross) and *Miscanthus*. In particular, we expect that the EDLL motif might be used to optimize transcription factors when used in combination with an inducible promoter, such as RD29A which is responsive to drought or cold. For example, certain transcription factors from the AP2 family, such as the CBF group, which confer abiotic stress tolerance when constitutively overexpressed, can also result in stunting; regulation of chimeric fusions of these AP2 family transcription factors with an EDLL motif combined with a tissue specific or inducible promoter provides a means of obtaining an enhanced crop without substantial negative phenotypes.

All publications and patent applications mentioned in this specification are herein incorporated by reference to the same extent as if each individual publication or patent application was specifically and individually indicated to be incorporated by reference.

The present invention is not limited by the specific embodiments described herein. The invention now being fully described, it will be apparent to one of ordinary skill in the art that many changes and modifications can be made thereto without departing from the spirit or scope of the Claims. Modifications that become apparent from the foregoing description and accompanying figures fall within the scope of the following Claims.

APPENDIX A

| AGI Number | TF Family | AGI Number | TF Family | AGI Number | TF Family | AGI Number | TF Family |
|---|---|---|---|---|---|---|---|
| AT5G06250 | ABI3/VP-1 | AT4G17695 | GARP | AT5G13790 | MADS | AT2G44730 | TH |
| AT4G32010 | ABI3/VP-1 | AT5G16560 | GARP | AT1G60920 | MADS | AT1G54060 | TH |

APPENDIX A-continued

| AGI Number | TF Family | AGI Number | TF Family | AGI Number | TF Family | AGI Number | TF Family |
|---|---|---|---|---|---|---|---|
| AT4G21550 | ABI3/VP-1 | AT4G37180 | GARP | AT1G60880 | MADS | AT3G10000 | TH |
| AT2G30470 | ABI3/VP-1 | AT4G16110 | GARP | AT1G59810 | MADS | AT3G24490 | TH |
| AT1G28300 | ABI3/VP-1 | AT2G01060 | GARP | AT1G48150 | MADS | AT1G21200 | TH |
| AT3G11580 | ABI3/VP-1 | AT5G05090 | GARP | AT1G69120 | MADS | AT1G76890 | TH |
| AT2G36080 | ABI3/VP-1 | AT4G31920 | GARP | AT4G18960 | MADS | AT1G33240 | TH |
| AT2G46870 | ABI3/VP-1 | AT1G49560 | GARP | AT4G24540 | MADS | AT1G16070 | TUBBY |
| AT2G33720 | ABI3/VP-1 | AT2G01760 | GARP | AT5G40120 | MADS | AT1G25280 | TUBBY |
| AT3G26790 | ABI3/VP-1 | AT3G24120 | GARP | AT5G62165 | MADS | AT5G18680 | TUBBY |
| AT4G01500 | ABI3/VP-1 | AT4G28610 | GARP | AT5G65330 | MADS | AT1G47270 | TUBBY |
| AT1G01030 | ABI3/VP-1 | AT3G04030 | GARP | AT5G41200 | MADS | AT1G43640 | TUBBY |
| AT3G61970 | ABI3/VP-1 | AT1G68670 | GARP | AT5G40220 | MADS | AT1G61940 | TUBBY |
| AT3G24650 | ABI3/VP-1 | AT1G69580 | GARP | AT5G39810 | MADS | AT1G53320 | TUBBY |
| AT3G19130 | ACBF-like | AT1G49190 | GARP | AT5G39750 | MADS | AT3G06380 | TUBBY |
| AT5G19350 | ACBF-like | AT2G20400 | GARP | AT5G38740 | MADS | AT2G18280 | TUBBY |
| AT1G47500 | ACBF-like | AT1G13300 | GARP | AT5G27580 | MADS | AT2G47900 | TUBBY |
| AT5G54900 | ACBF-like | AT2G02060 | GARP | AT5G27090 | MADS | AT1G76900 | TUBBY |
| AT1G49600 | ACBF-like | AT5G18240 | GARP | AT5G27070 | MADS | AT1G14410 | WHY |
| AT1G11650 | ACBF-like | AT5G29000 | GARP | AT5G27050 | MADS | AT1G71260 | WHY |
| AT1G47490 | ACBF-like | AT4G04580 | GARP | AT5G26950 | MADS | AT2G02740 | WHY |
| AT4G27000 | ACBF-like | AT5G45580 | GARP | AT5G04640 | MADS | AT2G25000 | WRKY |
| AT3G23300 | AKR | AT2G03500 | GARP | AT4G11250 | MADS | AT4G31550 | WRKY |
| AT5G06050 | AKR | AT2G40260 | GARP | AT3G18650 | MADS | AT1G13960 | WRKY |
| AT5G14430 | AKR | AT2G42660 | GARP | AT2G42830 | MADS | AT4G31800 | WRKY |
| AT1G26850 | AKR | AT2G20570 | GARP | AT3G02310 | MADS | AT2G04880 | WRKY |
| AT2G43200 | AKR | AT4G13640 | GARP | AT2G03710 | MADS | AT5G41570 | WRKY |
| AT2G45750 | AKR | AT3G10760 | GARP | AT5G15800 | MADS | AT2G44745 | WRKY |
| AT2G34300 | AKR | AT5G42630 | GARP | AT3G58780 | MADS | AT4G12020 | WRKY |
| AT1G29470 | AKR | AT1G25550 | GARP | AT1G26310 | MADS | AT3G01970 | WRKY |
| AT5G61230 | AKR | AT1G67710 | GARP | AT5G20240 | MADS | AT4G30935 | WRKY |
| AT1G19430 | AKR | AT2G25180 | GARP | AT3G54340 | MADS | AT2G30250 | WRKY |
| AT5G64030 | AKR | AT2G27070 | GARP | AT4G11880 | MADS | AT5G07100 | WRKY |
| AT5G04060 | AKR | AT5G59570 | GARP | AT3G61120 | MADS | AT4G01250 | WRKY |
| AT3G12360 | AKR | AT3G16857 | GARP | AT2G34440 | MADS | AT5G26170 | WRKY |
| AT5G15500 | AKR | AT3G62670 | GARP | AT5G60440 | MADS | AT5G64810 | WRKY |
| AT1G77260 | AKR | AT3G04450 | GARP | AT4G36590 | MADS | AT2G37260 | WRKY |
| AT5G45110 | AKR | AT3G12730 | GARP | AT1G01530 | MADS | AT3G58710 | WRKY |
| AT1G78240 | AKR | AT3G13040 | GARP | AT2G03060 | MADS | AT3G04670 | WRKY |
| AT1G14480 | AKR | AT3G25790 | GARP | AT1G77080 | MADS | AT3G56400 | WRKY |
| AT3G51070 | AKR | AT1G14600 | GARP | AT5G10140 | MADS | AT4G24240 | WRKY |
| AT3G57130 | AKR | AT3G46640 | GARP | AT5G65080 | MADS | AT5G43290 | WRKY |
| AT4G18030 | AKR | AT5G58080 | GARP | AT5G65070 | MADS | AT2G46130 | WRKY |
| AT1G04430 | AKR | AT5G07210 | GARP | AT5G65060 | MADS | AT2G46400 | WRKY |
| AT4G14365 | AKR | AT5G49240 | GARP | AT1G77950 | MADS | AT4G26640 | WRKY |
| AT5G66055 | AKR | AT1G32240 | GARP | AT1G77980 | MADS | AT5G49520 | WRKY |
| AT2G39750 | AKR | AT5G06800 | GARP | AT1G47760 | MADS | AT5G45260 | WRKY |
| AT1G64280 | AKR | AT3G19070 | GARP | AT3G05860 | MADS | AT4G01720 | WRKY |
| AT2G24600 | AKR | AT2G06020 | GARP | AT1G65360 | MADS | AT2G21900 | WRKY |
| AT5G54700 | AKR | AT4G18020 | GARP | AT1G65330 | MADS | AT4G23810 | WRKY |
| AT5G54710 | AKR | AT2G40970 | GARP | AT5G26870 | MADS | AT4G23550 | WRKY |
| AT2G31820 | AKR | AT4G36620 | GATA/Zn | AT5G27130 | MADS | AT4G26440 | WRKY |
| AT5G50140 | AKR | AT5G47140 | GATA/Zn | AT5G55690 | MADS | AT5G45050 | WRKY |
| AT1G03670 | AKR | AT3G51080 | GATA/Zn | AT5G51870 | MADS | AT5G22570 | WRKY |
| AT4G03440 | AKR | AT2G28340 | GATA/Zn | AT5G51860 | MADS | AT2G23320 | WRKY |
| AT4G03450 | AKR | AT4G32890 | GATA/Zn | AT2G24840 | MADS | AT5G52830 | WRKY |
| AT4G03460 | AKR | AT5G25830 | GATA/Zn | AT5G58890 | MADS | AT2G34830 | WRKY |
| AT5G40160 | AKR | AT5G66320 | GATA/Zn | AT1G29962 | MADS | AT4G39410 | WRKY |
| AT4G00750 | AKR | AT4G26150 | GATA/Zn | AT3G66656 | MADS | AT5G46350 | WRKY |
| AT4G19660 | AKR | AT2G18380 | GATA/Zn | AT1G17310 | MADS | AT2G47260 | WRKY |
| AT1G31850 | AKR | AT3G54810 | GATA/Zn | AT3G30260 | MADS | AT4G18170 | WRKY |
| AT4G19120 | AKR | AT5G56860 | GATA/Zn | AT1G31630 | MADS | AT1G62300 | WRKY |
| AT1G33170 | AKR | AT4G17570 | GATA/Zn | AT1G31640 | MADS | AT5G24110 | WRKY |
| AT4G10440 | AKR | AT5G49300 | GATA/Zn | AT5G06500 | MADS | AT4G11070 | WRKY |
| AT2G03480 | AKR | AT3G21175 | GATA/Zn | AT1G22130 | MADS | AT4G22070 | WRKY |
| AT4G00740 | AKR | AT3G50870 | GATA/Zn | AT1G54760 | MADS | AT1G55600 | WRKY |
| AT2G41370 | AKR | AT3G06740 | GATA/Zn | AT1G60040 | MADS | AT1G30650 | WRKY |
| AT4G26120 | AKR | AT4G24470 | GATA/Zn | AT2G22540 | MADS | AT2G30590 | WRKY |
| AT2G40280 | AKR | AT1G08000 | GATA/Zn | AT5G65050 | MADS | AT3G01080 | WRKY |
| AT2G03430 | AKR | AT3G16870 | GATA/Zn | AT2G26880 | MADS | AT1G64000 | WRKY |
| AT2G47450 | AKR | AT1G51600 | GATA/Zn | AT5G48670 | MADS | AT1G69810 | WRKY |
| AT4G10720 | AKR | AT1G08010 | GATA/Zn | AT3G24500 | MBFL | AT1G18860 | WRKY |
| AT5G54610 | AKR | AT3G45170 | GATA/Zn | AT3G58680 | MBFL | AT1G68150 | WRKY |
| AT2G01680 | AKR | AT2G45050 | GATA/Zn | AT2G42680 | MBFL | AT1G29280 | WRKY |
| AT5G60070 | AKR | AT4G34680 | GATA/Zn | AT5G66840 | MISC | AT1G69310 | WRKY |
| AT1G05640 | AKR | AT3G24050 | GATA/Zn | AT4G32551 | MISC | AT2G40740 | WRKY |
| AT1G10340 | AKR | AT4G36240 | GATA/Zn | AT2G32700 | MISC | AT5G28650 | WRKY |
| AT4G03470 | AKR | AT3G60530 | GATA/Zn | AT1G43850 | MISC | AT1G66550 | WRKY |
| AT4G03480 | AKR | AT1G14685 | GBP | AT4G25520 | MISC | AT1G66560 | WRKY |
| AT4G03490 | AKR | AT1G68120 | GBP | AT1G48050 | MISC | AT5G01900 | WRKY |

APPENDIX A-continued

| AGI Number | TF Family | AGI Number | TF Family | AGI Number | TF Family | AGI Number | TF Family |
|---|---|---|---|---|---|---|---|
| AT4G03500 | AKR | AT2G01930 | GBP | AT1G73230 | MISC | AT1G29860 | WRKY |
| AT4G05040 | AKR | AT5G42520 | GBP | AT1G17880 | MISC | AT5G15130 | WRKY |
| AT4G14400 | AKR | AT4G38910 | GBP | AT5G53060 | MISC | AT5G13080 | WRKY |
| AT4G14390 | AKR | AT2G21240 | GBP | AT5G23540 | MISC | AT1G66600 | WRKY |
| AT1G34050 | AKR | AT2G35550 | GBP | AT1G71230 | MISC | AT1G80590 | WRKY |
| AT3G54990 | AP2 | AT5G10450 | GF14 | AT4G20880 | MISC | AT3G62340 | WRKY |
| AT1G22190 | AP2 | AT5G16050 | GF14 | AT4G20880 | MISC | AT5G56270 | WRKY |
| AT5G25190 | AP2 | AT2G42590 | GF14 | AT3G43340 | MISC | AT2G24570 | WRKY |
| AT1G15360 | AP2 | AT1G22300 | GF14 | AT4G16420 | MISC | AT1G80840 | WRKY |
| AT1G25560 | AP2 | AT1G78220 | GF14 | AT5G09210 | MISC | AT2G40750 | WRKY |
| AT5G51990 | AP2 | AT1G34760 | GF14 | AT5G41580 | MISC | AT4G04450 | WRKY |
| AT2G39250 | AP2 | AT1G78300 | GF14 | AT1G08910 | MISC | AT2G38470 | WRKY |
| AT5G52020 | AP2 | AT5G38480 | GF14 | AT5G08550 | MISC | AT2G03340 | WRKY |
| AT5G07580 | AP2 | AT1G35160 | GF14 | AT1G22920 | MISC | AT1G23420 | YABBY |
| AT4G18450 | AP2 | AT4G09000 | GF14 | AT5G61850 | MISC | AT4G00180 | YABBY |
| AT2G38340 | AP2 | AT5G65430 | GF14 | AT3G07740 | MISC | AT1G69180 | YABBY |
| AT1G77200 | AP2 | AT3G02520 | GF14 | AT3G25515 | MISC | AT2G26580 | YABBY |
| AT5G53290 | AP2 | AT2G10450 | GF14 | AT5G62090 | MISC | AT2G45190 | YABBY |
| AT5G61600 | AP2 | AT3G52910 | GRF-like | AT3G13000 | NAC | AT1G08465 | YABBY |
| AT5G65130 | AP2 | AT2G06200 | GRF-like | AT1G32770 | NAC | AT2G40110 | YIP |
| AT1G78080 | AP2 | AT4G37740 | GRF-like | AT1G65910 | NAC | AT3G55890 | YIP |
| AT3G15210 | AP2 | AT3G13960 | GRF-like | AT4G35580 | NAC | AT4G27740 | YIP |
| AT2G47520 | AP2 | AT4G24150 | GRF-like | AT2G02450 | NAC | AT4G27745 | YIP |
| AT5G11190 | AP2 | AT2G42040 | GRF-like | AT1G01720 | NAC | AT5G53940 | YIP |
| AT5G18560 | AP2 | AT2G45480 | GRF-like | AT5G08790 | NAC | AT3G11230 | YIP |
| AT5G17430 | AP2 | AT2G22840 | GRF-like | AT3G10490 | NAC | AT3G08990 | YIP |
| AT1G19210 | AP2 | AT5G53660 | GRF-like | AT3G15550 | NAC | AT5G44160 | Z-C2H2 |
| AT5G18450 | AP2 | AT2G36400 | GRF-like | AT3G10480 | NAC | AT5G43170 | Z-C2H2 |
| AT5G10510 | AP2 | AT2G23760 | HB | AT2G24430 | NAC | AT5G04340 | Z-C2H2 |
| AT1G64380 | AP2 | AT5G44180 | HB | AT1G77450 | NAC | AT2G41940 | Z-C2H2 |
| AT2G33710 | AP2 | AT4G32880 | HB | AT3G04060 | NAC | AT5G48890 | Z-C2H2 |
| AT5G19790 | AP2 | AT2G34710 | HB | AT3G29035 | NAC | AT1G24625 | Z-C2H2 |
| AT3G50260 | AP2 | AT1G30490 | HB | AT4G36160 | NAC | AT5G25160 | Z-C2H2 |
| AT5G60120 | AP2 | AT4G17710 | HB | AT5G64060 | NAC | AT5G14010 | Z-C2H2 |
| AT3G23240 | AP2 | AT1G79840 | HB | AT5G63790 | NAC | AT1G80730 | Z-C2H2 |
| AT4G36900 | AP2 | AT4G00730 | HB | AT5G17260 | NAC | AT5G57520 | Z-C2H2 |
| AT3G11020 | AP2 | AT1G05230 | HB | AT1G02230 | NAC | AT1G66140 | Z-C2H2 |
| AT1G33760 | AP2 | AT4G21750 | HB | AT1G02250 | NAC | AT1G10480 | Z-C2H2 |
| AT3G25890 | AP2 | AT5G60690 | HB | AT1G02220 | NAC | AT1G67030 | Z-C2H2 |
| AT1G53170 | AP2 | AT5G65310 | HB | AT5G61430 | NAC | AT4G17810 | Z-C2H2 |
| AT5G57390 | AP2 | AT4G16780 | HB | AT5G24590 | NAC | AT4G27240 | Z-C2H2 |
| AT2G46310 | AP2 | AT5G47370 | HB | AT5G04400 | NAC | AT3G01030 | Z-C2H2 |
| AT2G25820 | AP2 | AT4G17460 | HB | AT1G02210 | NAC | AT3G02790 | Z-C2H2 |
| AT5G47220 | AP2 | AT3G60390 | HB | AT4G28500 | NAC | AT5G52010 | Z-C2H2 |
| AT1G50640 | AP2 | AT2G44910 | HB | AT1G26870 | NAC | AT5G66730 | Z-C2H2 |
| AT5G47230 | AP2 | AT5G06710 | HB | AT3G44290 | NAC | AT1G51220 | Z-C2H2 |
| AT4G06746 | AP2 | AT4G37790 | HB | AT2G18060 | NAC | AT5G60470 | Z-C2H2 |
| AT1G53910 | AP2 | AT2G22800 | HB | AT5G62380 | NAC | AT4G02670 | Z-C2H2 |
| AT1G51190 | AP2 | AT1G20710 | HB | AT1G60350 | NAC | AT5G03150 | Z-C2H2 |
| AT5G25390 | AP2 | AT1G70920 | HB | AT1G60340 | NAC | AT3G23130 | Z-C2H2 |
| AT2G35700 | AP2 | AT1G75430 | HB | AT1G60380 | NAC | AT2G28200 | Z-C2H2 |
| AT2G20880 | AP2 | AT5G46010 | HB | AT1G60300 | NAC | AT4G16610 | Z-C2H2 |
| AT1G36060 | AP2 | AT1G20700 | HB | AT1G60280 | NAC | AT2G37430 | Z-C2H2 |
| AT3G60490 | AP2 | AT1G46480 | HB | AT4G01520 | NAC | AT3G46090 | Z-C2H2 |
| AT3G20310 | AP2 | AT5G53980 | HB | AT4G01540 | NAC | AT5G59820 | Z-C2H2 |
| AT5G67190 | AP2 | AT4G25530 | HB | AT4G01550 | NAC | AT5G67450 | Z-C2H2 |
| AT4G11140 | AP2 | AT4G08150 | HB | AT1G32870 | NAC | AT4G31420 | Z-C2H2 |
| AT5G51190 | AP2 | AT2G17950 | HB | AT1G33060 | NAC | AT1G14580 | Z-C2H2 |
| AT5G67180 | AP2 | AT3G18010 | HB | AT3G15510 | NAC | AT3G19580 | Z-C2H2 |
| AT1G75490 | AP2 | AT5G66700 | HB | AT5G66300 | NAC | AT3G45260 | Z-C2H2 |
| AT5G61890 | AP2 | AT5G59340 | HB | AT2G27300 | NAC | AT5G05120 | Z-C2H2 |
| AT4G37750 | AP2 | AT1G69780 | HB | AT1G56010 | NAC | AT5G43540 | Z-C2H2 |
| AT5G25810 | AP2 | AT1G73360 | HB | AT3G49530 | NAC | AT2G42410 | Z-C2H2 |
| AT2G40350 | AP2 | AT3G03260 | HB | AT1G52880 | NAC | AT2G37740 | Z-C2H2 |
| AT2G40340 | AP2 | AT1G28420 | HB | AT4G27410 | NAC | AT2G26940 | Z-C2H2 |
| AT2G36450 | AP2 | AT1G75410 | HB | AT5G39820 | NAC | AT5G54360 | Z-C2H2 |
| AT2G31230 | AP2 | AT2G28610 | HB | AT5G56620 | NAC | AT5G54340 | Z-C2H2 |
| AT4G34410 | AP2 | AT2G27990 | HB | AT5G64530 | NAC | AT4G04404 | Z-C2H2 |
| AT4G27950 | AP2 | AT2G35940 | HB | AT5G14000 | NAC | AT5G61470 | Z-C2H2 |
| AT2G20350 | AP2 | AT4G04890 | HB | AT1G62700 | NAC | AT1G02040 | Z-C2H2 |
| AT2G22200 | AP2 | AT2G01500 | HB | AT2G43000 | NAC | AT2G17180 | Z-C2H2 |
| AT3G57600 | AP2 | AT5G17810 | HB | AT1G34180 | NAC | AT3G13810 | Z-C2H2 |
| AT1G12980 | AP2 | AT5G45980 | HB | AT1G01010 | NAC | AT2G45120 | Z-C2H2 |
| AT5G43410 | AP2 | AT2G33880 | HB | AT3G18400 | NAC | AT3G20880 | Z-C2H2 |
| AT5G64750 | AP2 | AT4G35550 | HB | AT3G17730 | NAC | AT3G23140 | Z-C2H2 |
| AT3G20840 | AP2 | AT5G46880 | HB | AT3G12910 | NAC | AT2G28710 | Z-C2H2 |
| AT3G23230 | AP2 | AT5G05770 | HB | AT3G04420 | NAC | AT2G01940 | Z-C2H2 |
| AT3G23220 | AP2 | AT1G34650 | HB | AT5G46590 | NAC | AT3G50700 | Z-C2H2 |

APPENDIX A-continued

| AGI Number | TF Family | AGI Number | TF Family | AGI Number | TF Family | AGI Number | TF Family |
|---|---|---|---|---|---|---|---|
| AT4G32800 | AP2 | AT1G23380 | HB | AT1G32510 | NAC | AT3G58070 | Z-C2H2 |
| AT4G28140 | AP2 | AT2G27220 | HB | AT1G34190 | NAC | AT3G53600 | Z-C2H2 |
| AT5G50080 | AP2 | AT2G16400 | HB | AT1G76420 | NAC | AT3G53820 | Z-C2H2 |
| AT5G67010 | AP2 | AT4G34610 | HB | AT3G03200 | NAC | AT1G68130 | Z-C2H2 |
| AT5G67000 | AP2 | AT2G36610 | HB | AT1G79580 | NAC | AT3G10470 | Z-C2H2 |
| AT5G65510 | AP2 | AT1G52150 | HB | AT3G56560 | NAC | AT1G13290 | Z-C2H2 |
| AT3G16770 | AP2 | AT2G18550 | HB | AT3G56530 | NAC | AT1G08290 | Z-C2H2 |
| AT2G41710 | AP2 | AT2G32370 | HB | AT3G56520 | NAC | AT3G09290 | Z-C2H2 |
| AT4G36920 | AP2 | AT2G01430 | HB | AT5G14490 | NAC | AT3G57670 | Z-C2H2 |
| AT1G28360 | AP2 | AT1G26960 | HB | AT3G44350 | NAC | AT3G46070 | Z-C2H2 |
| AT3G25730 | AP2 | AT4G03250 | HB | AT3G61910 | NAC | AT3G60580 | Z-C2H2 |
| AT4G13620 | AP2 | AT5G02030 | HB | AT1G71930 | NAC | AT5G56200 | Z-C2H2 |
| AT1G49120 | AP2 | AT3G01220 | HB | AT3G04070 | NAC | AT3G29340 | Z-C2H2 |
| AT1G79700 | AP2 | AT3G03660 | HB | AT1G28470 | NAC | AT1G26610 | Z-C2H2 |
| AT3G61630 | AP2 | AT1G19700 | HB | AT4G10350 | NAC | AT2G02070 | Z-C2H2 |
| AT1G21910 | AP2 | AT1G62990 | HB | AT3G15170 | NAC | AT2G02080 | Z-C2H2 |
| AT1G72570 | AP2 | AT5G52170 | HB | AT1G33280 | NAC | AT2G23740 | Z-C2H2 |
| AT1G28370 | AP2 | AT1G17920 | HB | AT3G04430 | NAC | AT2G15740 | Z-C2H2 |
| AT1G12890 | AP2 | AT3G11260 | HB | AT3G10500 | NAC | AT2G18490 | Z-C2H2 |
| AT1G63030 | AP2 | AT1G62360 | HB | AT1G03490 | NAC | AT5G10970 | Z-C2H2 |
| AT1G16060 | AP2 | AT1G70510 | HB | AT1G19040 | NAC | AT1G55110 | Z-C2H2 |
| AT1G72360 | AP2 | AT5G11060 | HB | AT1G64105 | NAC | AT5G06070 | Z-C2H2 |
| AT1G71450 | AP2 | AT5G25220 | HB | AT5G50820 | NAC | AT5G03510 | Z-C2H2 |
| AT1G71520 | AP2 | AT4G32040 | HB | AT3G04410 | NAC | AT5G01860 | Z-C2H2 |
| AT2G44940 | AP2 | AT4G32980 | HB | AT5G18300 | NAC | AT5G22890 | Z-C2H2 |
| AT1G77640 | AP2 | AT5G41410 | HB | AT5G18270 | NAC | AT3G46080 | Z-C2H2 |
| AT2G44840 | AP2 | AT4G36870 | HB | AT5G39610 | NAC | AT5G06650 | Z-C2H2 |
| AT1G71130 | AP2 | AT4G29940 | HB | AT2G33480 | NAC | AT4G35610 | Z-C2H2 |
| AT1G44830 | AP2 | AT3G19510 | HB | AT5G07680 | NAC | AT4G26030 | Z-C2H2 |
| AT1G28160 | AP2 | AT1G27050 | HB | AT1G60240 | NAC | AT1G34370 | Z-C2H2 |
| AT1G80580 | AP2 | AT2G46680 | HB | AT5G39690 | NAC | AT1G26590 | Z-C2H2 |
| AT3G16280 | AP2 | AT4G36740 | HB | AT5G41090 | NAC | AT1G03840 | Z-C2H2 |
| AT5G11590 | AP2 | AT5G15150 | HB | AT4G29230 | NAC | AT5G42640 | Z-C2H2 |
| AT5G21960 | AP2 | AT3G01470 | HB | AT3G01600 | NAC | AT5G27880 | Z-C2H2 |
| AT2G23340 | AP2 | AT2G22430 | HB | AT3G55210 | NAC | AT5G22990 | Z-C2H2 |
| AT1G12630 | AP2 | AT5G17320 | HB | AT5G09330 | NAC | AT3G49930 | Z-C2H2 |
| AT1G12610 | AP2 | AT3G61890 | HB | AT1G25580 | NAC | AT1G68360 | Z-C2H2 |
| AT1G06160 | AP2 | AT4G40060 | HB | AT5G22290 | NAC | AT1G25250 | Z-C2H2 |
| AT1G01250 | AP2 | AT3G61150 | HB | AT5G22380 | NAC | AT1G43860 | Z-C2H2 |
| AT5G07310 | AP2 | AT5G03790 | HB | AT4G28530 | NAC | AT2G29660 | Z-C2H2 |
| AT4G16750 | AP2 | AT3G19860 | HLH/MYC | AT2G17040 | NAC | AT1G30970 | Z-C2H2 |
| AT1G25470 | AP2 | AT3G47640 | HLH/MYC | AT4G17980 | NAC | AT5G15480 | Z-C2H2 |
| AT1G51120 | AP2 | AT1G02340 | HLH/MYC | AT5G53950 | NAC | AT5G54630 | Z-C2H2 |
| AT1G50680 | AP2 | AT1G03040 | HLH/MYC | AT1G61110 | NAC | AT5G16470 | Z-C2H2 |
| AT4G17500 | AP2 | AT1G51070 | HLH/MYC | AT1G69490 | NAC | AT2G27100 | Z-C2H2 |
| AT1G24590 | AP2 | AT5G54680 | HLH/MYC | AT5G13180 | NAC | AT4G12240 | Z-C2H2 |
| AT1G22985 | AP2 | AT3G23210 | HLH/MYC | AT1G12260 | NAC | AT4G35700 | Z-C2H2 |
| AT4G39780 | AP2 | AT3G59060 | HLH/MYC | AT5G04410 | NAC | AT1G34790 | Z-C2H2 |
| AT5G61590 | AP2 | AT2G22770 | HLH/MYC | AT1G52890 | NAC | AT3G29340 | Z-C2H2 |
| AT4G25480 | AP2 | AT5G57150 | HLH/MYC | AT1G54330 | NAC | AT4G16845 | Z-C2H2 |
| AT4G25470 | AP2 | AT1G29950 | HLH/MYC | AT2G46770 | NAC | AT5G51230 | Z-C2H2 |
| AT4G25490 | AP2 | AT3G23690 | HLH/MYC | AT5G56780 | OTHER | AT2G35670 | Z-C2H2 |
| AT3G14230 | AP2 | AT1G05805 | HLH/MYC | AT4G26170 | OTHER | AT1G11490 | Z-C2H2 |
| AT4G31060 | AP2 | AT5G43175 | HLH/MYC | AT4G27330 | OTHER | AT1G75710 | Z-C2H2 |
| AT5G05410 | AP2 | AT5G61270 | HLH/MYC | AT5G35770 | OTHER | AT4G35280 | Z-C2H2 |
| AT1G22810 | AP2 | AT3G05800 | HLH/MYC | AT5G21030 | PAZ | AT1G27730 | Z-C2H2 |
| AT4G17490 | AP2 | AT1G27740 | HLH/MYC | AT2G27880 | PAZ | AT1G49900 | Z-C2H2 |
| AT1G04370 | AP2 | AT3G57800 | HLH/MYC | AT1G48410 | PAZ | AT1G02030 | Z-C2H2 |
| AT1G46768 | AP2 | AT3G50330 | HLH/MYC | AT2G27040 | PAZ | AT2G24500 | Z-C2H2 |
| AT5G44210 | AP2 | AT1G69010 | HLH/MYC | AT1G69440 | PAZ | AT2G19810 | Z-C3H |
| AT1G03800 | AP2 | AT1G68920 | HLH/MYC | AT2G32940 | PAZ | AT4G29190 | Z-C3H |
| AT5G13910 | AP2 | AT1G68810 | HLH/MYC | AT5G43810 | PAZ | AT2G40140 | Z-C3H |
| AT2G40220 | AP2 | AT3G06590 | HLH/MYC | AT5G08330 | PCF | AT3G19360 | Z-C3H |
| AT1G43160 | AP2 | AT1G59640 | HLH/MYC | AT1G58100 | PCF | AT3G12130 | Z-C3H |
| AT1G74930 | AP2 | AT3G06120 | HLH/MYC | AT3G47500 | PCF | AT1G68200 | Z-C3H |
| AT1G68550 | AP2 | AT5G65640 | HLH/MYC | AT2G37000 | PCF | AT5G58620 | Z-C3H |
| AT1G13260 | AP2 | AT1G31050 | HLH/MYC | AT5G23280 | PCF | AT1G32360 | Z-C3H |
| AT5G13330 | AP2 | AT5G58010 | HLH/MYC | AT3G27010 | PCF | AT2G35430 | Z-C3H |
| AT4G23750 | AP2 | AT3G19500 | HLH/MYC | AT5G51910 | PCF | AT2G41900 | Z-C3H |
| AT2G28550 | AP2 | AT1G18400 | HLH/MYC | AT5G41030 | PCF | AT5G07500 | Z-C3H |
| AT1G68840 | AP2 | AT5G48560 | HLH/MYC | AT3G45150 | PCF | AT3G55980 | Z-C3H |
| AT3G54320 | AP2 | AT5G08130 | HLH/MYC | AT1G72010 | PCF | AT1G03790 | Z-C3H |
| AT1G30330 | ARF | AT4G37850 | HLH/MYC | AT2G45680 | PCF | AT5G44260 | Z-C3H |
| AT3G61830 | ARF | AT4G05170 | HLH/MYC | AT1G35560 | PCF | AT5G12850 | Z-C3H |
| AT1G34310 | ARF | AT4G29930 | HLH/MYC | AT1G69690 | PCF | AT5G06770 | Z-C3H |
| AT5G20730 | ARF | AT4G28811 | HLH/MYC | AT2G22300 | PCGL | AT2G25900 | Z-C3H |
| AT1G19220 | ARF | AT2G40200 | HLH/MYC | AT5G64220 | PCGL | AT4G22140 | Z-C4HC3 |
| AT1G59750 | ARF | AT1G30670 | HLH/MYC | AT4G16150 | PCGL | AT4G04260 | Z-C4HC3 |

APPENDIX A-continued

| AGI Number | TF Family | AGI Number | TF Family | AGI Number | TF Family | AGI Number | TF Family |
|---|---|---|---|---|---|---|---|
| AT5G37020 | ARF | AT2G43140 | HLH/MYC | AT5G09410 | PCGL | AT5G26210 | Z-C4HC3 |
| AT2G46530 | ARF | AT3G25710 | HLH/MYC | AT1G67310 | PCGL | AT5G05610 | Z-C4HC3 |
| AT1G77850 | ARF | AT3G17100 | HLH/MYC | AT3G16940 | PCGL | AT3G42790 | Z-C4HC3 |
| AT4G30080 | ARF | AT3G20640 | HLH/MYC | AT2G23380 | PCOMB | AT3G11200 | Z-C4HC3 |
| AT1G34390 | ARF | AT4G29100 | HLH/MYC | AT1G02580 | PCOMB | AT1G14510 | Z-C4HC3 |
| AT1G35240 | ARF | AT1G27660 | HLH/MYC | AT4G02020 | PCOMB | AT5G20510 | Z-C4HC3 |
| AT1G34410 | ARF | AT1G05710 | HLH/MYC | AT1G79020 | PCOMB | AT2G02470 | Z-C4HC3 |
| AT1G35520 | ARF | AT2G31730 | HLH/MYC | AT1G16690 | PCOMB | AT4G39100 | Z-C4HC3 |
| AT1G35540 | ARF | AT2G20100 | HLH/MYC | AT3G20740 | PCOMB | AT4G36020 | Z-CLDSH |
| AT2G28350 | ARF | AT1G61660 | HLH/MYC | AT1G31040 | PLATZ | AT4G38680 | Z-CLDSH |
| AT1G43950 | ARF | AT5G51790 | HLH/MYC | AT4G17900 | PLATZ | AT2G17870 | Z-CLDSH |
| AT2G33860 | ARF | AT5G51780 | HLH/MYC | AT3G60670 | PLATZ | AT2G21060 | Z-CLDSH |
| AT4G23980 | ARF | AT5G38860 | HLH/MYC | AT5G46710 | PLATZ | AT2G24790 | Z-CO-like |
| AT5G62000 | ARF | AT1G25330 | HLH/MYC | AT1G21000 | PLATZ | AT1G28050 | Z-CO-like |
| AT1G19850 | ARF | AT1G49830 | HLH/MYC | AT1G76590 | PLATZ | AT4G15248 | Z-CO-like |
| AT5G60450 | ARF | AT1G73830 | HLH/MYC | AT1G43000 | PLATZ | AT1G60250 | Z-CO-like |
| AT1G34170 | ARF | AT5G04150 | HLH/MYC | AT2G27930 | PLATZ | AT4G39070 | Z-CO-like |
| AT1G76110 | ARID | AT4G25400 | HLH/MYC | AT2G12646 | PLATZ | AT2G21320 | Z-CO-like |
| AT1G76510 | ARID | AT4G25410 | HLH/MYC | AT2G01818 | PLATZ | AT1G49130 | Z-CO-like |
| AT1G20910 | ARID | AT3G56970 | HLH/MYC | AT1G32700 | PLATZ | AT3G21880 | Z-CO-like |
| AT2G17410 | ARID | AT3G56980 | HLH/MYC | AT1G12860 | PMR | AT3G21150 | Z-CO-like |
| AT1G55650 | ARID | AT1G12540 | HLH/MYC | AT2G43440 | PMR | AT5G15840 | Z-CO-like |
| AT1G04880 | ARID | AT1G71200 | HLH/MYC | AT2G43270 | PMR | AT3G07650 | Z-CO-like |
| AT3G13350 | ARID | AT1G62975 | HLH/MYC | AT2G05600 | PMR | AT3G02380 | Z-CO-like |
| AT1G06280 | AS2/LOB | AT2G41240 | HLH/MYC | AT2G02030 | PMR | AT1G06040 | Z-CO-like |
| AT1G67100 | AS2/LOB | AT5G56960 | HLH/MYC | AT2G43445 | PMR | AT5G15850 | Z-CO-like |
| AT2G31310 | AS2/LOB | AT5G65320 | HLH/MYC | AT2G43260 | PMR | AT2G33500 | Z-CO-like |
| AT2G30340 | AS2/LOB | AT1G10585 | HLH/MYC | AT2G42955 | PMR | AT4G15250 | Z-CO-like |
| AT2G30130 | AS2/LOB | AT4G20970 | HLH/MYC | AT1G13200 | PMR | AT1G05290 | Z-CO-like |
| AT2G28500 | AS2/LOB | AT5G43650 | HLH/MYC | AT1G11270 | PMR | AT2G47890 | Z-CO-like |
| AT2G23660 | AS2/LOB | AT4G30180 | HLH/MYC | AT5G61380 | PRR | AT1G25440 | Z-CO-like |
| AT2G19820 | AS2/LOB | AT2G47270 | HLH/MYC | AT5G24470 | PRR | AT1G68520 | Z-CO-like |
| AT2G19510 | AS2/LOB | AT4G38070 | HLH/MYC | AT2G46790 | PRR | AT4G10240 | Z-CO-like |
| AT1G72980 | AS2/LOB | AT5G37800 | HLH/MYC | AT2G46670 | PRR | AT1G75540 | Z-CO-like |
| AT1G68510 | AS2/LOB | AT5G67110 | HLH/MYC | AT5G02810 | PRR | AT4G27310 | Z-CO-like |
| AT3G58190 | AS2/LOB | AT2G31220 | HLH/MYC | AT5G60100 | PRR | AT5G24930 | Z-CO-like |
| AT3G50510 | AS2/LOB | AT2G31210 | HLH/MYC | AT1G26680 | REM | AT5G48250 | Z-CO-like |
| AT3G49940 | AS2/LOB | AT1G06170 | HLH/MYC | AT1G49480 | REM | AT1G73870 | Z-CO-like |
| AT3G47870 | AS2/LOB | AT1G10610 | HLH/MYC | AT3G53310 | REM | AT3G21890 | Z-CO-like |
| AT3G27940 | AS2/LOB | AT1G49770 | HLH/MYC | AT3G06220 | REM | AT2G31380 | Z-CO-like |
| AT3G27650 | AS2/LOB | AT1G51140 | HLH/MYC | AT3G46770 | REM | AT1G68190 | Z-CO-like |
| AT3G26660 | AS2/LOB | AT1G26260 | HLH/MYC | AT5G09780 | REM | AT4G38960 | Z-CO-like |
| AT3G26620 | AS2/LOB | AT4G28815 | HLH/MYC | AT5G66980 | REM | AT1G78600 | Z-CO-like |
| AT3G13850 | AS2/LOB | AT5G41315 | HLH/MYC | AT5G60140 | REM | AT5G57660 | Z-CO-like |
| AT3G11090 | AS2/LOB | AT4G17880 | HLH/MYC | AT5G60130 | REM | AT5G54470 | Z-CO-like |
| AT3G03760 | AS2/LOB | AT1G32640 | HLH/MYC | AT5G57720 | REM | AT3G50410 | Z-Dof |
| AT3G02550 | AS2/LOB | AT4G00870 | HLH/MYC | AT5G18090 | REM | AT2G34140 | Z-Dof |
| AT2G45420 | AS2/LOB | AT4G00480 | HLH/MYC | AT5G18000 | REM | AT4G00940 | Z-Dof |
| AT2G45410 | AS2/LOB | AT1G01260 | HLH/MYC | AT4G33280 | REM | AT2G28810 | Z-Dof |
| AT2G42440 | AS2/LOB | AT4G00120 | HLH/MYC | AT4G00260 | REM | AT5G60200 | Z-Dof |
| AT2G42430 | AS2/LOB | AT4G00050 | HLH/MYC | AT2G24650 | REM | AT3G52440 | Z-Dof |
| AT2G40470 | AS2/LOB | AT4G36060 | HLH/MYC | AT2G24640 | REM | AT1G07640 | Z-Dof |
| AT5G67420 | AS2/LOB | AT5G23290 | HLH/MYC | AT2G24680 | REM | AT2G37590 | Z-Dof |
| AT5G66870 | AS2/LOB | AT4G36540 | HLH/MYC | AT2G24690 | REM | AT3G55370 | Z-Dof |
| AT5G63090 | AS2/LOB | AT4G14410 | HLH/MYC | AT2G24700 | REM | AT5G60850 | Z-Dof |
| AT5G35900 | AS2/LOB | AT2G42280 | HLH/MYC | AT4G31690 | REM | AT1G69570 | Z-Dof |
| AT5G06080 | AS2/LOB | AT4G02590 | HLH/MYC | AT4G31680 | REM | AT3G21270 | Z-Dof |
| AT4G37540 | AS2/LOB | AT4G36930 | HLH/MYC | AT4G31660 | REM | AT1G51700 | Z-Dof |
| AT4G22700 | AS2/LOB | AT4G30980 | HLH/MYC | AT4G31650 | REM | AT5G62430 | Z-Dof |
| AT4G00220 | AS2/LOB | AT4G16430 | HLH/MYC | AT4G34400 | REM | AT1G47655 | Z-Dof |
| AT4G00210 | AS2/LOB | AT1G63650 | HLH/MYC | AT3G18990 | REM | AT5G66940 | Z-Dof |
| AT1G65620 | AS2/LOB | AT5G53210 | HLH/MYC | AT3G17010 | REM | AT5G65590 | Z-Dof |
| AT1G07900 | AS2/LOB | AT3G61950 | HLH/MYC | AT3G06160 | REM | AT1G26790 | Z-Dof |
| AT1G16530 | AS2/LOB | AT2G46810 | HLH/MYC | AT2G35310 | REM | AT4G21080 | Z-Dof |
| AT1G31320 | AS2/LOB | AT4G01460 | HLH/MYC | AT4G16210 | REM | AT2G28510 | Z-Dof |
| AT1G36000 | AS2/LOB | AT5G46690 | HLH/MYC | AT4G31640 | REM | AT4G38000 | Z-Dof |
| AT2G45430 | AT-Hook | AT1G09530 | HLH/MYC | AT4G31630 | REM | AT2G46590 | Z-Dof |
| AT3G18035 | AT-Hook | AT4G21330 | HLH/MYC | AT4G31615 | REM | AT5G02460 | Z-Dof |
| AT3G60870 | AT-Hook | AT2G41130 | HLH/MYC | AT4G31620 | REM | AT1G21340 | Z-Dof |
| AT5G49700 | AT-Hook | AT5G64340 | HLH/MYC | AT4G31610 | REM | AT3G45610 | Z-Dof |
| AT4G12080 | AT-Hook | AT5G46760 | HLH/MYC | AT2G37120 | S1FA | AT4G21040 | Z-Dof |
| AT3G55560 | AT-Hook | AT2G16910 | HLH/MYC | AT3G09735 | S1FA | AT1G28310 | Z-Dof |
| AT1G76500 | AT-Hook | AT4G09180 | HLH/MYC | AT3G53370 | S1FA | AT4G21030 | Z-Dof |
| AT1G14490 | AT-Hook | AT5G09460 | HLH/MYC | AT5G43270 | SBP | AT4G21050 | Z-Dof |
| AT3G04590 | AT-Hook | AT2G27230 | HLH/MYC | AT2G42200 | SBP | AT1G29160 | Z-Dof |
| AT3G04570 | AT-Hook | AT2G34820 | HLH/MYC | AT3G15270 | SBP | AT5G62940 | Z-Dof |
| AT1G63470 | AT-Hook | AT4G33880 | HLH/MYC | AT2G47070 | SBP | AT5G39660 | Z-Dof |
| AT1G63480 | AT-Hook | AT4G34530 | HLH/MYC | AT5G50670 | SBP | AT3G61850 | Z-Dof |

APPENDIX A-continued

| AGI Number | TF Family | AGI Number | TF Family | AGI Number | TF Family | AGI Number | TF Family |
|---|---|---|---|---|---|---|---|
| AT2G45850 | AT-Hook | AT5G67060 | HLH/MYC | AT1G27370 | SBP | AT4G24060 | Z-Dof |
| AT4G22810 | AT-Hook | AT3G26744 | HLH/MYC | AT1G20980 | SBP | AT1G64620 | Z-Dof |
| AT4G14465 | AT-Hook | AT2G24260 | HLH/MYC | AT1G53160 | SBP | AT3G47500 | Z-Dof |
| AT4G17950 | AT-Hook | AT5G46830 | HLH/MYC | AT1G76580 | SBP | AT1G01780 | Z-LIM |
| AT1G20900 | AT-Hook | AT5G09750 | HLH/MYC | AT3G60030 | SBP | AT1G10200 | Z-LIM |
| AT4G25320 | AT-Hook | AT2G20180 | HLH/MYC | AT5G18830 | SBP | AT2G45800 | Z-LIM |
| AT1G48620 | AT-Hook | AT2G18300 | HLH/MYC | AT3G57920 | SBP | AT3G61230 | Z-LIM |
| AT5G62260 | AT-Hook | AT2G43010 | HLH/MYC | AT1G02065 | SBP | AT2G39900 | Z-LIM |
| AT2G42940 | AT-Hook | AT4G09820 | HLH/MYC | AT1G27360 | SBP | AT3G55770 | Z-LIM |
| AT5G51590 | AT-Hook | AT2G46510 | HLH/MYC | AT2G33810 | SBP | AT1G02170 | Z-LSDlike |
| AT5G46640 | AT-Hook | AT1G12860 | HLH/MYC | AT1G69170 | SBP | AT5G64240 | Z-LSDlike |
| AT4G17800 | AT-Hook | AT2G22760 | HLH/MYC | AT2G29060 | SCR | AT4G25110 | Z-LSDlike |
| AT2G35270 | AT-Hook | AT1G09250 | HLH/MYC | AT1G55580 | SCR | AT4G21610 | Z-LSDlike |
| AT4G35390 | AT-Hook | AT2G14760 | HLH/MYC | AT5G41920 | SCR | AT1G32540 | Z-LSDlike |
| AT4G00200 | AT-Hook | AT1G10120 | HLH/MYC | AT1G07520 | SCR | AT4G20380 | Z-LSDlike |
| AT3G61310 | AT-Hook | AT2G22750 | HLH/MYC | AT2G04890 | SCR | AT2G41590 | Z-Tall-1 |
| AT4G12050 | AT-Hook | AT4G21340 | HLH/MYC | AT4G37650 | SCR | AT2G36930 | Z-ZPF |
| AT1G22310 | AT-Hook | AT4G28790 | HLH/MYC | AT3G46600 | SCR | AT5G22480 | Z-ZPF |
| AT1G14900 | AT-Hook | AT2G46970 | HLH/MYC | AT4G48150 | SCR | AT3G28920 | ZF-HB |
| AT4G22770 | AT-Hook | AT1G22490 | HLH/MYC | AT3G50650 | SCR | AT5G15210 | ZF-HB |
| AT1G48610 | AT-Hook | AT3G24140 | HLH/MYC | AT3G03450 | SCR | AT1G14440 | ZF-HB |
| AT2G33620 | AT-Hook | AT4G28800 | HLH/MYC | AT3G49950 | SCR | AT2G02540 | ZF-HB |
| AT3G50750 | BES | AT2G42300 | HLH/MYC | AT2G45160 | SCR | AT1G69600 | ZF-HB |
| AT4G18890 | BES | AT3G21330 | HLH/MYC | AT1G50600 | SCR | AT5G39760 | ZF-HB |
| AT1G78700 | BES | AT1G06150 | HLH/MYC | AT3G60630 | SCR | AT5G60480 | ZF-HB |
| AT1G19350 | BES | AT1G35460 | HLH/MYC | AT4G08250 | SCR | AT1G14687 | ZF-HB |
| AT1G75080 | BES | AT1G64625 | HLH/MYC | AT3G13840 | SCR | AT5G42780 | ZF-HB |
| AT4G36780 | BES | AT2G31280 | HLH/MYC | AT1G07530 | SCR | AT3G50890 | ZF-HB |
| AT3G12560 | BPF-1 | AT2G28160 | HLH/MYC | AT5G17490 | SCR | AT2G18350 | ZF-HB |
| AT5G59430 | BPF-1 | AT5G62610 | HLH/MYC | AT1G66350 | SCR | AT1G75240 | ZF-HB |
| AT3G53790 | BPF-1 | AT5G01310 | HLH/MYC | AT1G14920 | SCR | AT4G24660 | ZF-HB |
| AT1G07540 | BPF-1 | AT3G07340 | HLH/MYC | AT2G01570 | SCR | AT5G65410 | ZF-HB |
| AT3G46590 | BPF-1 | AT3G56770 | HLH/MYC | AT3G54220 | SCR | AT5G24800 | bZIP |
| AT5G13820 | BPF-1 | AT1G72210 | HLH/MYC | AT4G36710 | SCR | AT5G28770 | bZIP |
| AT5G12840 | CAAT | AT5G10570 | HLH/MYC | AT5G67411 | SCR | AT1G77920 | bZIP |
| AT1G17590 | CAAT | AT4G23800 | HMG | AT4G17230 | SCR | AT5G15830 | bZIP |
| AT2G34720 | CAAT | AT4G35570 | HMG | AT5G66770 | SCR | AT5G34000 | bZIP |
| AT3G05690 | CAAT | AT3G51880 | HMG | AT4G00150 | SCR | AT5G38800 | bZIP |
| AT3G48590 | CAAT | AT5G23420 | HMG | AT2G37650 | SCR | AT5G44080 | bZIP |
| AT1G54830 | CAAT | AT1G20693 | HMG | AT5G52510 | SCR | AT5G06839 | bZIP |
| AT1G72830 | CAAT | AT2G17560 | HMG | AT5G59450 | SCR | AT1G68640 | bZIP |
| AT5G43250 | CAAT | AT3G28730 | HMG | AT1G63100 | SCR | AT2G36270 | bZIP |
| AT2G47810 | CAAT | AT1G20696 | HMG | AT1G21450 | SCR | AT3G62420 | bZIP |
| AT5G63470 | CAAT | AT4G11080 | HMG | AT1G50420 | SCR | AT2G24340 | bZIP |
| AT1G54160 | CAAT | AT2G34450 | HMG | AT5G66350 | SRS | AT1G13600 | bZIP |
| AT2G13570 | CAAT | AT5G16820 | HS | AT3G51060 | SRS | AT5G08139 | bZIP |
| AT5G27910 | CAAT | AT3G02990 | HS | AT5G33210 | SRS | AT3G44460 | bZIP |
| AT5G47670 | CAAT | AT3G51910 | HS | AT2G18120 | SRS | AT3G56660 | bZIP |
| AT5G50480 | CAAT | AT4G17600 | HS | AT1G75520 | SRS | AT2G40950 | bZIP |
| AT5G50470 | CAAT | AT3G22830 | HS | AT1G19790 | SRS | AT2G41070 | bZIP |
| AT5G50490 | CAAT | AT5G43840 | HS | AT4G36260 | SRS | AT3G10800 | bZIP |
| AT5G38140 | CAAT | AT1G32330 | HS | AT2G21400 | SRS | AT2G04038 | bZIP |
| AT2G37060 | CAAT | AT5G03720 | HS | AT5G12330 | SRS | AT3G58120 | bZIP |
| AT3G14020 | CAAT | AT3G63350 | HS | AT3G54430 | SRS | AT2G42380 | bZIP |
| AT5G06510 | CAAT | AT2G41690 | HS | AT4G00390 | STK | AT2G21230 | bZIP |
| AT1G08970 | CAAT | AT2G26150 | HS | AT1G11510 | STK | AT3G30530 | bZIP |
| AT1G09030 | CAAT | AT5G45710 | HS | AT1G61730 | STK | AT1G42990 | bZIP |
| AT4G14540 | CAAT | AT4G13980 | HS | AT4G00250 | STK | AT2G22850 | bZIP |
| AT5G23090 | CAAT | AT4G36990 | HS | AT4G00610 | STK | AT3G54620 | bZIP |
| AT1G56170 | CAAT | AT4G17750 | HS | AT4G01260 | STK | AT1G08320 | bZIP |
| AT5G47640 | CAAT | AT4G18880 | HS | AT3G04930 | STK | AT3G56850 | bZIP |
| AT2G38880 | CAAT | AT4G18870 | HS | AT5G14280 | STK | AT3G19290 | bZIP |
| AT1G21970 | CAAT | AT5G62020 | HS | AT5G28040 | STK | AT2G35530 | bZIP |
| AT3G53340 | CAAT | AT4G11660 | HS | AT4G00270 | STK | AT5G60830 | bZIP |
| AT1G30500 | CAAT | AT5G54070 | HS | AT2G36340 | STK | AT3G51960 | bZIP |
| AT2G27470 | CAAT | AT1G67970 | HS | AT2G01370 | STK | AT1G75390 | bZIP |
| AT3G20910 | CAAT | AT1G77570 | HS | AT2G25650 | STK | AT5G49450 | bZIP |
| AT5G08190 | CAAT | AT1G46264 | HS | AT4G25210 | STK | AT2G16770 | bZIP |
| AT1G07980 | CAAT | AT4G19630 | HS | AT1G66420 | STK | AT3G17609 | bZIP |
| AT3G12480 | CAAT | AT3G24520 | HS | AT1G44810 | STK | AT4G37730 | bZIP |
| AT3G12890 | CCT | AT5G25890 | IAA | AT1G50410 | SWI/SNF | AT4G38900 | bZIP |
| AT2G32310 | CCT | AT3G23030 | IAA | AT5G20420 | SWI/SNF | AT2G40620 | bZIP |
| AT1G07050 | CCT | AT1G80390 | IAA | AT5G19310 | SWI/SNF | AT4G34590 | bZIP |
| AT5G59990 | CCT | AT1G04550 | IAA | AT1G11100 | SWI/SNF | AT1G03970 | bZIP |
| AT4G27900 | CCT | AT2G33310 | IAA | AT1G02670 | SWI/SNF | AT2G46270 | bZIP |
| AT5G53420 | CCT | AT3G15540 | IAA | AT1G05120 | SWI/SNF | AT4G01120 | bZIP |
| AT1G63820 | CCT | AT1G52830 | IAA | AT1G08060 | SWI/SNF | AT4G36730 | bZIP |
| AT5G41380 | CCT | AT2G22670 | IAA | AT5G22750 | SWI/SNF | AT2G31370 | bZIP |

APPENDIX A-continued

| AGI Number | TF Family | AGI Number | TF Family | AGI Number | TF Family | AGI Number | TF Family |
|---|---|---|---|---|---|---|---|
| AT5G14370 | CCT | AT1G15580 | IAA | AT1G08600 | SWI/SNF | AT5G06950 | bZIP |
| AT4G25990 | CCT | AT5G65670 | IAA | AT2G16390 | SWI/SNF | AT3G49760 | bZIP |
| AT1G04500 | CCT | AT3G04730 | IAA | AT2G21450 | SWI/SNF | AT1G68880 | bZIP |
| AT5G57180 | CCT | AT3G23050 | IAA | AT3G24340 | SWI/SNF | AT1G06850 | bZIP |
| AT2G33350 | CCT | AT1G15050 | IAA | AT3G06010 | SWI/SNF | AT2G12900 | bZIP |
| AT4G14770 | CPP | AT4G32280 | IAA | AT1G03750 | SWI/SNF | AT2G12940 | bZIP |
| AT3G04850 | CPP | AT5G57420 | IAA | AT5G66750 | SWI/SNF | AT2G13150 | bZIP |
| AT5G25790 | CPP | AT2G01200 | IAA | AT2G44980 | SWI/SNF | AT1G35490 | bZIP |
| AT4G29000 | CPP | AT2G46990 | IAA | AT2G18760 | SWI/SNF | AT1G49720 | bZIP |
| AT3G22780 | CPP | AT1G51950 | IAA | AT1G48310 | SWI/SNF | AT1G59530 | bZIP |
| AT3G22760 | CPP | AT4G28640 | IAA | AT5G63950 | SWI/SNF | AT1G43700 | bZIP |
| AT3G16160 | CPP | AT4G14560 | IAA | AT3G19210 | SWI/SNF | AT2G21235 | bZIP |
| AT2G20110 | CPP | AT3G16500 | IAA | AT3G54460 | SWI/SNF | AT5G42910 | bZIP |
| AT4G32780 | DBP | AT3G17600 | IAA | AT1G61140 | SWI/SNF | AT1G45249 | bZIP |
| AT4G14740 | DBP | AT4G29080 | IAA | AT3G06400 | SWI/SNF | AT1G32150 | bZIP |
| AT4G17410 | DBP | AT3G62100 | IAA | AT5G18620 | SWI/SNF | AT4G35900 | bZIP |
| AT1G45207 | DBP | AT5G43700 | IAA | AT5G43530 | SWI/SNF | AT4G02640 | bZIP |
| AT2G45820 | DBP | AT1G04250 | IAA | AT2G40770 | SWI/SNF | AT5G11260 | bZIP |
| AT4G36970 | DBP | AT1G04240 | IAA | AT5G22750 | SWI/SNF | AT5G10030 | bZIP |
| AT3G63300 | DBP | AT4G14550 | IAA | AT5G05130 | SWI/SNF | AT5G06960 | bZIP |
| AT3G48940 | DBP | AT1G04100 | IAA | AT3G16600 | SWI/SNF | AT5G65210 | bZIP |
| AT1G30320 | DBP | AT2G34880 | JUMONJI | AT3G12810 | SWI/SNF | AT1G22070 | bZIP |
| AT5G57540 | DBP | AT5G46910 | JUMONJI | AT1G05490 | SWI/SNF | AT2G17770 | bZIP |
| AT5G57770 | DBP | AT3G48430 | JUMONJI | AT4G31900 | SWI/SNF | AT5G04840 | bZIP |
| AT5G43870 | DBP | AT5G04240 | JUMONJI | AT2G13370 | SWI/SNF | AT3G12250 | bZIP |
| AT5G47430 | DBP | AT1G63490 | JUMONJI | AT2G28290 | SWI/SNF | AT4G35040 | bZIP |
| AT2G41870 | DBP | AT2G38950 | JUMONJI | AT5G44800 | SWI/SNF | AT1G06070 | bZIP |
| AT3G61260 | DBP | AT1G08620 | JUMONJI | AT3G54280 | SWI/SNF | AT2G18160 | bZIP |
| AT5G23750 | DBP | AT1G30810 | JUMONJI | AT3G20010 | SWI/SNF | AT3G59580 | bZIP-NIN |
| AT4G17350 | DBP | AT4G20400 | JUMONJI | AT3G42670 | SWI/SNF | AT2G17150 | bZIP-NIN |
| AT2G02170 | DBP | AT5G24890 | KCL | AT2G25170 | SWI/SNF | AT1G64530 | bZIP-NIN |
| AT4G00670 | DBP | AT4G31510 | KCL | AT3G57300 | SWI/SNF | AT2G43500 | bZIP-NIN |
| AT1G67590 | DBP | AT2G24550 | KCL | AT2G02090 | SWI/SNF | AT1G20640 | bZIP-NIN |
| AT4G16670 | DBP | AT1G31140 | MADS | AT2G46020 | SWI/SNF | AT1G18790 | bZIP-NIN |
| AT3G22810 | DBP | AT3G57390 | MADS | AT1G67260 | TEO | AT1G74480 | bZIP-NIN |
| AT2G33700 | DBPP | AT3G57230 | MADS | AT1G30210 | TEO | AT5G66990 | bZIP-NIN |
| AT3G62260 | DBPP | AT4G22950 | MADS | AT4G18390 | TEO | AT5G53040 | bZIP-NIN |
| AT1G48040 | DBPP | AT5G38620 | MADS | AT3G02150 | TEO | AT4G35590 | bZIP-NIN |
| AT3G51470 | DBPP | AT1G46408 | MADS | AT2G31070 | TEO | AT1G76350 | bZIP-NIN |
| AT3G17250 | DBPP | AT1G69540 | MADS | AT3G15030 | TEO | AT4G24020 | bZIP-NIN |
| AT2G25620 | DBPP | AT1G18750 | MADS | AT1G68800 | TEO | AT4G38340 | bZIP-NIN |
| AT3G48160 | E2F | AT1G22590 | MADS | AT5G60970 | TEO | AT4G35270 | bZIP-NIN |
| AT5G14960 | E2F | AT5G27960 | MADS | AT3G18550 | TEO | AT1G09950 | bZIP-ZW2 |
| AT5G02470 | E2F | AT2G28700 | MADS | AT5G08070 | TEO | AT4G18660 | bZIP-ZW2 |
| AT2G36010 | E2F | AT1G28460 | MADS | AT1G53230 | TEO | AT4G18690 | bZIP-ZW2 |
| AT1G47870 | E2F | AT1G28450 | MADS | AT1G13450 | TH | AT1G58330 | bZIP-ZW2 |
| AT5G22220 | E2F | AT2G40210 | MADS | AT1G76880 | TH | AT3G14880 | bZIP-ZW2 |
| AT5G03415 | E2F | AT3G04100 | MADS | AT5G47660 | TH | AT5G45830 | bZIP-ZW2 |
| AT3G01330 | E2F | AT1G72350 | MADS | AT4G17050 | TH | AT4G18680 | bZIP-ZW2 |
| AT2G27050 | EIL | AT5G23260 | MADS | AT3G58630 | TH | AT4G18650 | bZIP-ZW2 |
| AT5G21120 | EIL | AT5G60910 | MADS | AT4G31270 | TH | AT1G77500 | bZIPt2 |
| AT5G10120 | EIL | AT2G45660 | MADS | AT2G33550 | TH | AT3G60320 | bZIPt2 |
| AT3G20770 | EIL | AT5G26650 | MADS | AT2G38250 | TH | AT2G27090 | bZIPt2 |
| AT5G65100 | EIL | AT5G26630 | MADS | AT5G28300 | TH | AT4G39790 | bZIPt2 |
| AT1G73730 | EIL | AT5G26580 | MADS | AT5G03680 | TH | AT1G52320 | bZIPt2 |
| AT1G09060 | ENBP | AT2G26520 | MADS | AT5G63420 | TH | AT1G20550 | bZIPt2 |
| AT1G62310 | ENBP | AT1G65300 | MADS | AT2G35640 | TH | AT2G19090 | bZIPt2 |
| AT4G21430 | ENBP | AT4G37940 | MADS | AT3G25990 | TH | AT4G35240 | bZIPt2 |
| AT4G00990 | ENBP | AT1G71692 | MADS | AT1G31310 | TH | AT2G34670 | bZIPt2 |
| AT1G11950 | ENBP | AT4G09960 | MADS | AT3G10040 | TH | AT3G51290 | bZIPt2 |
| AT3G07610 | ENBP | AT1G24260 | MADS | AT3G24860 | TH | AT2G17110 | bZIPt2 |
| AT4G21670 | FRY | AT5G49490 | MADS | AT5G05550 | TH | AT5G54480 | bZIPt2 |
| AT5G01270 | FRY | AT5G49420 | MADS | AT3G54390 | TH | AT5G25590 | bZIPt2 |
| AT2G38300 | GARP | AT2G45650 | MADS | AT3G11100 | TH | AT1G02110 | bZIPt2 |
| AT5G44190 | GARP | AT2G14210 | MADS | AT3G14180 | TH | AT5G62320 | MYB-(R1)R2R3 |
| AT1G79430 | GARP | AT2G22630 | MADS | AT5G01380 | TH | AT5G11050 | MYB-(R1)R2R3 |
| AT4G01680 | MYB-(R1)R2R3 | AT1G66370 | MYB-(R1)R2R3 | AT5G55020 | MYB-(R1)R2R3 | AT5G02840 | MYB-related |
| AT3G30210 | MYB-(R1)R2R3 | AT1G66380 | MYB-(R1)R2R3 | AT2G26960 | MYB-(R1)R2R3 | AT5G56840 | MYB-related |
| AT4G00540 | MYB-(R1)R2R3 | AT5G67300 | MYB-(R1)R2R3 | AT3G28470 | MYB-(R1)R2R3 | AT1G19000 | MYB-related |
| AT4G38620 | MYB-(R1)R2R3 | AT5G57620 | MYB-(R1)R2R3 | AT4G37780 | MYB-(R1)R2R3 | AT5G23650 | MYB-related |
| AT1G66390 | MYB-(R1)R2R3 | AT5G59780 | MYB-(R1)R2R3 | AT5G52600 | MYB-(R1)R2R3 | AT5G37260 | MYB-related |

APPENDIX A-continued

| AGI Number | TF Family | AGI Number | TF Family | AGI Number | TF Family | AGI Number | TF Family |
|---|---|---|---|---|---|---|---|
| AT5G10280 | MYB-(R1)R2R3 | AT5G40350 | MYB-(R1)R2R3 | AT4G13480 | MYB-(R1)R2R3 | AT5G01200 | MYB-related |
| AT2G37630 | MYB-(R1)R2R3 | AT2G47460 | MYB-(R1)R2R3 | AT5G49620 | MYB-(R1)R2R3 | AT4G01280 | MYB-related |
| AT1G79180 | MYB-(R1)R2R3 | AT4G37260 | MYB-(R1)R2R3 | AT1G56650 | MYB-(R1)R2R3 | AT1G17520 | MYB-related |
| AT1G22640 | MYB-(R1)R2R3 | AT2G47190 | MYB-(R1)R2R3 | AT4G05100 | MYB-(R1)R2R3 | AT1G19510 | MYB-related |
| AT4G32730 | MYB-(R1)R2R3 | AT4G25560 | MYB-(R1)R2R3 | AT1G56160 | MYB-(R1)R2R3 | AT1G75250 | MYB-related |
| AT5G60890 | MYB-(R1)R2R3 | AT2G02820 | MYB-(R1)R2R3 | AT1G26780 | MYB-(R1)R2R3 | AT1G01380 | MYB-related |
| AT5G58850 | MYB-(R1)R2R3 | AT1G63910 | MYB-(R1)R2R3 | AT2G13960 | MYB-(R1)R2R3 | AT1G49950 | MYB-related |
| AT3G08500 | MYB-(R1)R2R3 | AT5G02320 | MYB-(R1)R2R3 | AT3G18100 | MYB-(R1)R2R3 | AT3G49850 | MYB-related |
| AT1G25340 | MYB-(R1)R2R3 | AT3G02940 | MYB-(R1)R2R3 | AT3G13890 | MYB-(R1)R2R3 | AT3G10580 | MYB-related |
| AT1G18710 | MYB-(R1)R2R3 | AT1G74080 | MYB-(R1)R2R3 | AT5G49330 | MYB-(R1)R2R3 | AT4G36570 | MYB-related |
| AT3G62610 | MYB-(R1)R2R3 | AT3G13540 | MYB-(R1)R2R3 | AT3G46130 | MYB-(R1)R2R3 | AT5G08520 | MYB-related |
| AT1G66230 | MYB-(R1)R2R3 | AT5G15310 | MYB-(R1)R2R3 | AT1G43330 | MYB-(R1)R2R3 | AT5G61620 | MYB-related |
| AT5G14750 | MYB-(R1)R2R3 | AT4G09460 | MYB-(R1)R2R3 | AT4G18770 | MYB-(R1)R2R3 | AT5G04760 | MYB-related |
| AT1G34670 | MYB-(R1)R2R3 | AT3G50060 | MYB-(R1)R2R3 | AT4G26930 | MYB-(R1)R2R3 | AT5G17300 | MYB-related |
| AT3G48920 | MYB-(R1)R2R3 | AT5G26660 | MYB-(R1)R2R3 | AT2G25230 | MYB-(R1)R2R3 | AT5G05790 | MYB-related |
| AT1G18570 | MYB-(R1)R2R3 | AT3G27810 | MYB-(R1)R2R3 | AT3G29020 | MYB-(R1)R2R3 | AT5G58900 | MYB-related |
| AT1G09540 | MYB-(R1)R2R3 | AT4G17785 | MYB-(R1)R2R3 | AT4G21440 | MYB-(R1)R2R3 | AT2G38090 | MYB-related |
| AT5G35550 | MYB-(R1)R2R3 | AT3G09230 | MYB-(R1)R2R3 | AT4G34990 | MYB-(R1)R2R3 | AT2G21650 | MYB-related |
| AT5G62470 | MYB-(R1)R2R3 | AT2G39880 | MYB-(R1)R2R3 | AT1G06180 | MYB-(R1)R2R3 | AT4G09450 | MYB-related |
| AT5G16600 | MYB-(R1)R2R3 | AT4G33450 | MYB-(R1)R2R3 | AT5G65230 | MYB-(R1)R2R3 | AT5G53200 | MYB-related |
| AT3G28910 | MYB-(R1)R2R3 | AT3G11440 | MYB-(R1)R2R3 | AT5G17800 | MYB-(R1)R2R3 | AT5G52660 | MYB-related |
| AT3G47600 | MYB-(R1)R2R3 | AT1G68320 | MYB-(R1)R2R3 | AT5G61420 | MYB-(R1)R2R3 | AT4G39250 | MYB-related |
| AT1G18960 | MYB-(R1)R2R3 | AT1G16490 | MYB-(R1)R2R3 | AT5G07690 | MYB-(R1)R2R3 | AT2G46830 | MYB-related |
| AT3G12720 | MYB-(R1)R2R3 | AT3G01530 | MYB-(R1)R2R3 | AT4G12350 | MYB-(R1)R2R3 | AT1G01520 | MYB-related |
| AT2G32460 | MYB-(R1)R2R3 | AT1G73410 | MYB-(R1)R2R3 | AT1G35515 | MYB-(R1)R2R3 | AT2G30420 | MYB-related |
| AT1G74650 | MYB-(R1)R2R3 | AT1G17950 | MYB-(R1)R2R3 | AT1G08810 | MYB-(R1)R2R3 | AT2G46410 | MYB-related |
| AT2G16720 | MYB-(R1)R2R3 | AT1G57560 | MYB-(R1)R2R3 | AT3G24310 | MYB-(R1)R2R3 | AT3G09600 | MYB-related |
| AT1G48000 | MYB-(R1)R2R3 | AT5G12870 | MYB-(R1)R2R3 | AT3G27920 | MYB-(R1)R2R3 | AT1G49010 | MYB-related |
| AT5G11510 | MYB-(R1)R2R3 | AT4G28110 | MYB-(R1)R2R3 | AT3G49690 | MYB-(R1)R2R3 | AT1G18330 | MYB-related |
| AT3G60460 | MYB-(R1)R2R3 | AT5G14340 | MYB-(R1)R2R3 | AT3G23250 | MYB-(R1)R2R3 | AT3G10590 | MYB-related |
| AT3G55730 | MYB-(R1)R2R3 | AT2G36890 | MYB-(R1)R2R3 | AT5G65790 | MYB-(R1)R2R3 | AT1G72740 | MYB-related |
| AT1G14350 | MYB-(R1)R2R3 | AT5G23000 | MYB-(R1)R2R3 | AT4G22680 | MYB-(R1)R2R3 | AT2G30432 | MYB-related |
| AT5G54230 | MYB-(R1)R2R3 | AT5G06100 | MYB-(R1)R2R3 | AT2G23290 | MYB-(R1)R2R3 | AT5G67580 | MYB-related |
| AT5G56110 | MYB-(R1)R2R3 | AT3G53200 | MYB-(R1)R2R3 | AT5G40430 | MYB-(R1)R2R3 | AT1G71030 | MYB-related |
| AT5G07700 | MYB-(R1)R2R3 | AT5G52260 | MYB-(R1)R2R3 | AT5G40330 | MYB-(R1)R2R3 | AT1G74840 | MYB-related |
| AT3G09370 | MYB-(R1)R2R3 | AT3G61250 | MYB-(R1)R2R3 | AT5G39700 | MYB-(R1)R2R3 | AT1G70000 | MYB-related |
| AT3G01140 | MYB-(R1)R2R3 | AT2G31180 | MYB-(R1)R2R3 | AT3G27785 | MYB-(R1)R2R3 | AT1G09770 | MYB-related |
| AT1G74430 | MYB-(R1)R2R3 | AT3G12820 | MYB-(R1)R2R3 | AT5G40360 | MYB-(R1)R2R3 | AT3G16350 | MYB-related |
| AT1G69560 | MYB-(R1)R2R3 | AT5G16770 | MYB-(R1)R2R3 | AT2G18328 | MYB-related | AT4G01060 | MYB-related |

APPENDIX A-continued

| AGI Number | TF Family | AGI Number | TF Family | AGI Number | TF Family | AGI Number | TF Family |
|---|---|---|---|---|---|---|---|
| MYB-AT3G06490 | MYB-(R1)R2R3 | AT2G26950 | (R1)R2R3 | AT5G47390 | MYB-related | AT3G11280 | MYB-related |
| | | | | | | AT1G01060 | MYB-related |

What is claimed is:

1. A chimeric polypeptide consisting of a transactivation domain covalently linked to a heterologous transcription regulatory polypeptide, wherein said transactivation domain consists of SEQ ID NO: 37 or a sequence having at least 25% identity thereto and comprising SEQ ID NO: 55, and wherein said transcription regulatory polypeptide comprises a DNA binding domain.

2. The chimeric polypeptide of claim 1, wherein the transcription regulatory polypeptide is a transcription factor polypeptide.

3. The chimeric polypeptide of claim 1, wherein the transactivation domain consists of SEQ ID NO: 37.

4. A recombinant polynucleotide encoding the chimeric polypeptide according to claim 1.

5. The recombinant polynucleotide of claim 4, wherein said recombinant polynucleotide further comprises an inducible, developmental or tissue-specific promoter.

6. A host plant cell comprising the recombinant polynucleotide of claim 4.

7. The host plant cell of claim 6, wherein the transcription regulatory polypeptide is a transcription factor polypeptide.

8. The host plant cell of claim 6, wherein the transactivation domain consists of SEQ ID NO: 37.

9. The host plant cell of claim 6, wherein the recombinant polynucleotide comprises an inducible, developmental or tissue-specific promoter.

10. A transgenic plant comprising a host plant cell according to claim 6.

11. A method for increasing expression of a target polynucleotide sequence, the method comprising:
   (a) generating a nucleic acid construct encoding a chimeric polypeptide consisting of a transactivation domain covalently linked to a heterologous transcription regulatory polypeptide, wherein said transactivation domain consists of SEQ ID NO: 37 or a sequence having at least 25% identity thereto and comprising SEQ ID NO:55, and, wherein said transcription regulatory polypeptide comprises a DNA binding domain; and
   (b) introducing the nucleic acid construct into a host cell.

12. The method of claim 11, wherein the transcription regulatory polypeptide is a transcription factor polypeptide.

13. The method of claim 11, wherein the nucleic acid construct comprises an inducible, developmental or tissue-specific promoter.

14. The method of claim 11, wherein said transactivation domain consists of an amino acid sequence having at least 70% identity to SEQ ID NO: 37 and comprising SEQ ID NO: 55.

15. The method of claim 14, wherein said transactivation domain consists of an amino acid sequence having at least 80% identity to SEQ ID NO: 37 and comprising SEQ ID NO: 55.

16. The method of claim 15, wherein the said transactivation domain consists of an amino acid sequence having at least 90% identity to SEQ ID NO: 37 and comprising SEQ ID NO: 55.

17. The method of claim 11, wherein said transactivation domain consists of the amino acid sequence of SEQ ID NO: 37.

18. The method of claim 11, wherein the nucleotide sequence encoding said transactivation domain consists of SEQ ID NO: 76.

19. The method of claim 11, wherein the host cell is a plant cell.

20. The method of claim 19, wherein the plant cell is a crop plant cell.

21. The method of claim 20, wherein the crop plant cell is from a rice, maize, soybean, or alfalfa plant.

22. The method of claim 19, further comprising a step of: (c) regenerating a transgenic plant from the host cell.

23. A transgenic plant produced by the method of claim 22.

24. A plant part or seed of the transgenic plant of claim 23, wherein said plant part or seed comprises said nucleic acid construct.

25. The chimeric polypeptide of claim 1, wherein said transactivation domain consists of an amino acid sequence having at least 70% identity to SEQ ID NO: 37 and comprising SEQ ID NO: 55.

26. The chimeric polypeptide of claim 1, wherein said transactivation domain consists of an amino acid sequence having at least 80% identity to SEQ ID NO: 37 and comprising SEQ ID NO: 55.

27. The chimeric polypeptide of claim 1, wherein said transactivation domain consists of an amino acid sequence having at least 90% identity to SEQ ID NO: 37 and comprising SEQ ID NO: 55.

28. The chimeric polypeptide of claim 1, wherein said transactivation domain consists of the amino acid sequence of SEQ ID NO: 37.

29. The chimeric polypeptide of claim 1, wherein the nucleotide sequence encoding said transactivation domain consists of SEQ ID NO: 76.

30. The host plant cell of claim 6, wherein the plant cell is a crop plant cell.

31. The host plant cell of claim 30, wherein the crop plant cell is from a rice, maize, soybean, or alfalfa plant.

* * * * *